(12) United States Patent
Cao et al.

(10) Patent No.: US 9,982,231 B2
(45) Date of Patent: May 29, 2018

(54) METHODS FOR REPROGRAMMING DIFFERENTIATED NON-CARDIAC CELLS INTO CARDIOMYOCYTES

(71) Applicant: The J. David Gladstone Institutes, a testamentary trust established under the Will of J. David Gladstone, San Francisco, CA (US)

(72) Inventors: Nan Cao, San Francisco, CA (US); Sheng Ding, Orinda, CA (US)

(73) Assignee: THE J. DAVID GLADSTONE INSTITUTES, A TESTAMENTARY TRUST ESTABLISHED UNDER THE WILL OF J. DAVID GLADSTONE, San Francisco, CA (US)

( * ) Notice: Subject to any disclaimer, the term of this patent is extended or adjusted under 35 U.S.C. 154(b) by 0 days. days.

(21) Appl. No.: 15/066,312

(22) Filed: Mar. 10, 2016

(65) Prior Publication Data

US 2016/0186141 A1    Jun. 30, 2016

Related U.S. Application Data

(63) Continuation-in-part of application No. PCT/US2014/055083, filed on Sep. 11, 2014.

(60) Provisional application No. 61/876,649, filed on Sep. 11, 2013.

(51) Int. Cl.

| | |
|---|---|
| A61L 27/38 | (2006.01) |
| C12N 5/077 | (2010.01) |
| A61K 45/06 | (2006.01) |
| A61K 31/404 | (2006.01) |
| A61K 31/416 | (2006.01) |
| A61K 31/4409 | (2006.01) |
| A61K 31/4709 | (2006.01) |
| A61K 31/506 | (2006.01) |
| A61K 31/519 | (2006.01) |
| A61K 31/551 | (2006.01) |
| A61K 31/192 | (2006.01) |
| A61K 31/437 | (2006.01) |
| A61K 35/34 | (2015.01) |

(52) U.S. Cl.
CPC .......... *C12N 5/0657* (2013.01); *A61K 31/192* (2013.01); *A61K 31/404* (2013.01); *A61K 31/416* (2013.01); *A61K 31/437* (2013.01); *A61K 31/4409* (2013.01); *A61K 31/4709* (2013.01); *A61K 31/506* (2013.01); *A61K 31/519* (2013.01); *A61K 31/551* (2013.01); *A61K 35/34* (2013.01); *A61K 45/06* (2013.01); *A61L 27/3826* (2013.01); *A61L 27/3895* (2013.01); *A61L 2430/20* (2013.01); *C12N 2501/065* (2013.01); *C12N 2501/11* (2013.01); *C12N 2501/135* (2013.01); *C12N 2501/15* (2013.01); *C12N 2501/155* (2013.01); *C12N 2501/16* (2013.01); *C12N 2501/415* (2013.01); *C12N 2501/603* (2013.01); *C12N 2501/72* (2013.01); *C12N 2501/727* (2013.01); *C12N 2501/998* (2013.01); *C12N 2501/999* (2013.01); *C12N 2506/1307* (2013.01)

(58) Field of Classification Search
None
See application file for complete search history.

(56) References Cited

U.S. PATENT DOCUMENTS

| | | | | |
|---|---|---|---|---|
| 2009/0325288 A1* | 12/2009 | Koshimizu | .......... | C12N 5/0657 435/366 |
| 2015/0297611 A1* | 10/2015 | Dzau | .............. | C12Y 201/01043 514/218 |
| 2016/0251624 A1* | 9/2016 | Wang | .................... | C12N 5/0657 |
| 2017/0002325 A1* | 1/2017 | Palecek | ................ | C12N 5/0657 |

FOREIGN PATENT DOCUMENTS

| | | | |
|---|---|---|---|
| EP | 2014766 A1 | | 1/2009 |
| KR | 2013/085752 | * | 7/2013 |
| KR | 1020130085752 A1 | | 7/2013 |
| WO | WO-2011153236 A1 | | 12/2011 |
| WO | WO-2012135176 A2 | | 10/2012 |
| WO | WO-2012140274 A2 | | 10/2012 |
| WO | WO-2015038704 A1 | | 3/2015 |

OTHER PUBLICATIONS

Cao N. et al. Highly Efficient Induction and Long Term Maintenance of Multipotent Cardiovascular Progenitors from Human Pluripotent Stem Cells Under Defined Conditions. Cell Research 23(9)1119-1132, Jul. 2013.*
Efe J. Conversion of Mouse Fibroblasts Inot Cardiomyocytes Using a Direct Reprogramming Strategy. Nature Cell Biology 13(3)215-222, Mar. 2011.*
"International Application Serial No. PCT/US2014/055083, International Search Report dated Feb. 4, 2015", 8 pgs.
"International Application Serial No. PCT/US2014/055083, Invitation to Pay Additional Fees and Partial Search Report dated Dec. 2, 2014", 8 pgs.
"International Application Serial No. PCT/US2014/055083, Written Opinion dated Feb. 4, 2015", 14 pgs.
Cao, Nan, et al., "Highly efficient induction and long-term maintenance of multipotent cardiovascular progenitors from human pluripotent stem cells under defined conditions", Cell Research, vol. 23, No. 9, (Jul. 30, 2013), 1119-1132.
Lev, Sophie, et al., "Differentiation Pathways in Human Embryonic Stem Cell-Derived Cardiomyocytes", Annals of The New York Academy of Sciences vol. 1047, No. 1, (Jun. 1, 2005), 50-65.
Lian, Xiaojun, et al., "Directed cardiomyocyte differentiation from human pluripotent stem cells by modulating Wnt/β-catenin signaling under fully defined conditions", Nature Protocols, vol. 8, No. 1, (Dec. 20, 2012), 162-175.
Liu, J., et al., "A small-molecule agonist of the Wnt signaling pathway", Angewandte Chemie International Edition, vol. 44, No. 13, (Mar. 18, 2005), 1987-1990.
Tseng, Al-Sun, et al., "The GSK-3 Inhibitor BIO Promotes Proliferation in Mammalian Cardiomyocytes", Chemistry and Biology, Current Biology, vol. 13, No. 9, (Sep. 1, 2006), 957-963.

* cited by examiner

*Primary Examiner* — Ralph J Gitomer
(74) *Attorney, Agent, or Firm* — Convergent Law Group LLP

(57) ABSTRACT

Compositions and methods are described herein for chemically inducing cells to change their differentiation state and become cardiac progenitor cells or cardiomyocytes.

**22 Claims, 25 Drawing Sheets
(11 of 25 Drawing Sheet(s) Filed in Color)**

| N | $V_{max}$ (V.s$^{-1}$) | MDP (mV) | OSP (mV) | APD$_{90}$ (ms) | Ca transient (F/F$_0$) | Ca transient $t_{10-90\%}$ (ms) |
|---|---|---|---|---|---|---|
| 15 | 55.8 ± 10.8 | -76.3 ± 1.1 | +37.9 ± 1.4 | 283.8 ± 32.9 | 3.4 ± 0.4 | 912.9 ± 66.8 |

*Fig. 6C*

| Cell | n | Ventricular (%) | $V_{max}$ (V·s$^{-1}$) | BF (Hz) | APD$_{90}$ (ms) | Amplitude (F/F$_0$) | $T_{10-90\%}$ (ms) | OSP (mV) | MDP (mV) |
|---|---|---|---|---|---|---|---|---|---|
| 9C-AS8351+PBIT | 13 | 100 | 19.0±1.4 | 0.4±0.03 | 501.1±72.2 | 1.6±0.05 | 1496.4±133.2 | 33.5±1.2 | -77.9±0.8 |

Fig. 8C

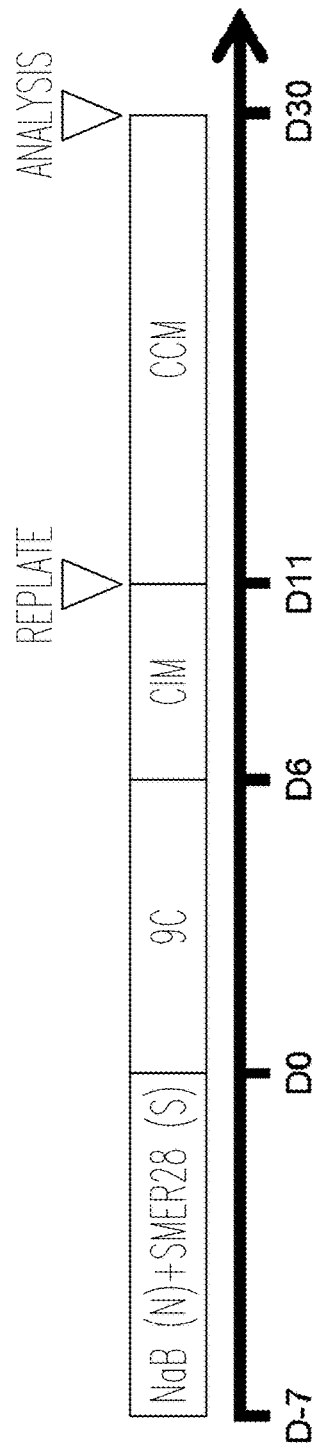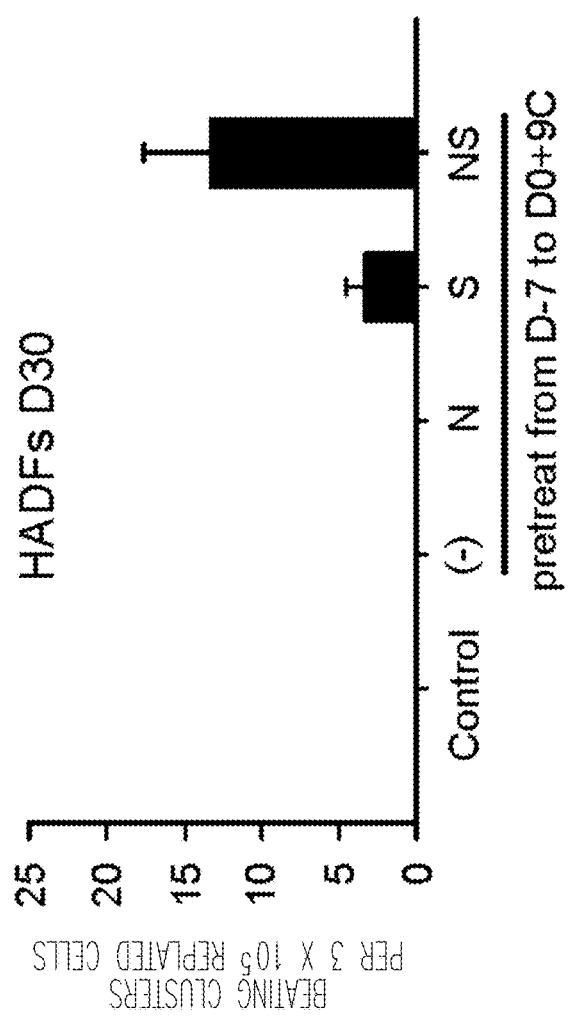
Fig. 9A
Fig. 9B

HADF-CMs

HADF-CMs

| N | BF (Hz) | $V_{max}$ (V·s⁻¹) | MDP (mV) |
|---|---|---|---|
| 10 | 0.8 ± 0.1 | 28.9 ± 4.0 | −72.6 ± 1.1 |

| OSP (mV) | $APD_{90}$ (ms) | Amplitude (F/F₀) | $T_{10-90\%}$ (ms) |
|---|---|---|---|
| 34.5 ± 2.8 | 440.7 ± 52.9 | 1.5 ± 0.1 | 1112.9 ± 180.9 |

Fig. 10E

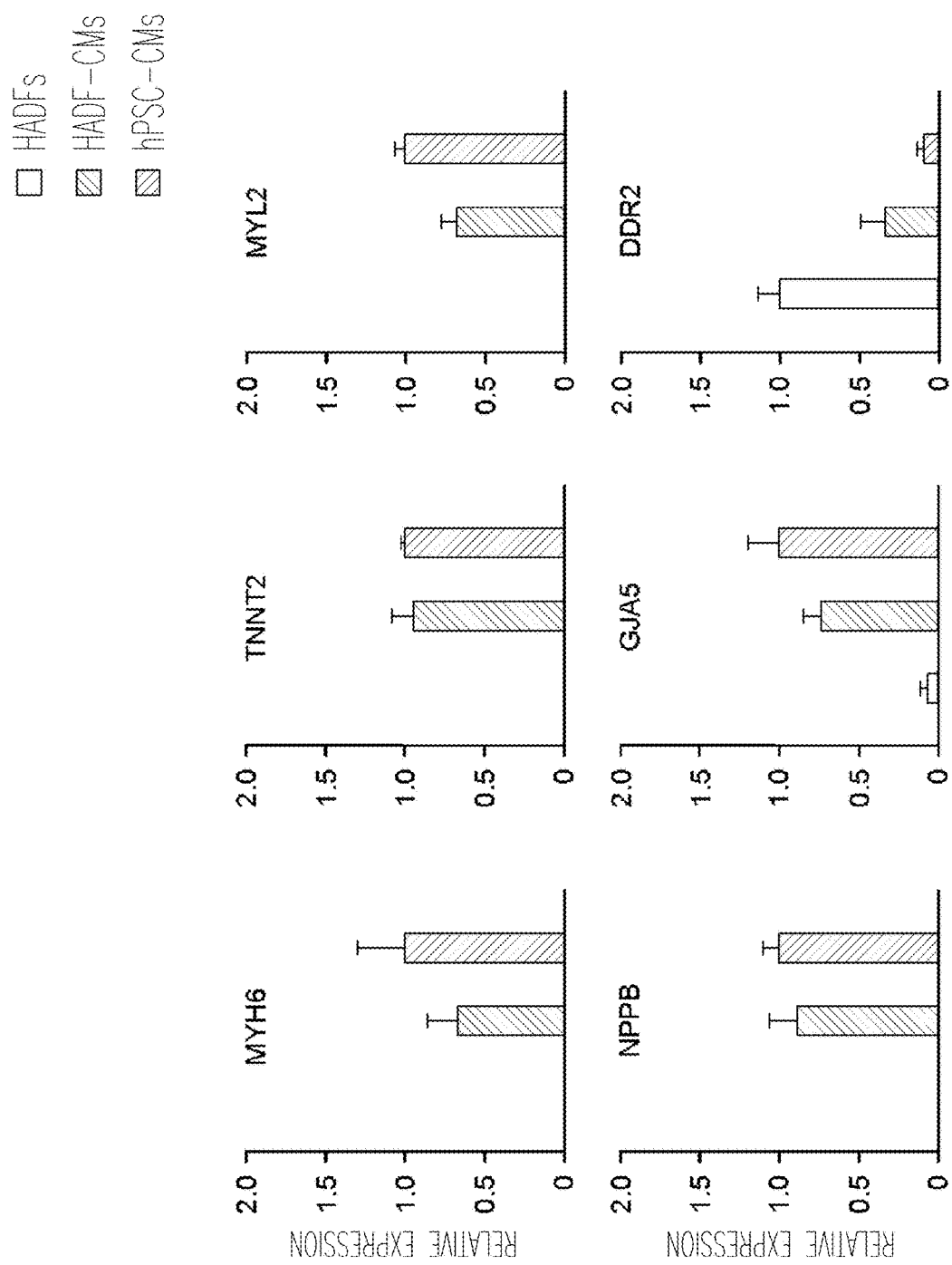
Fig. 10C1

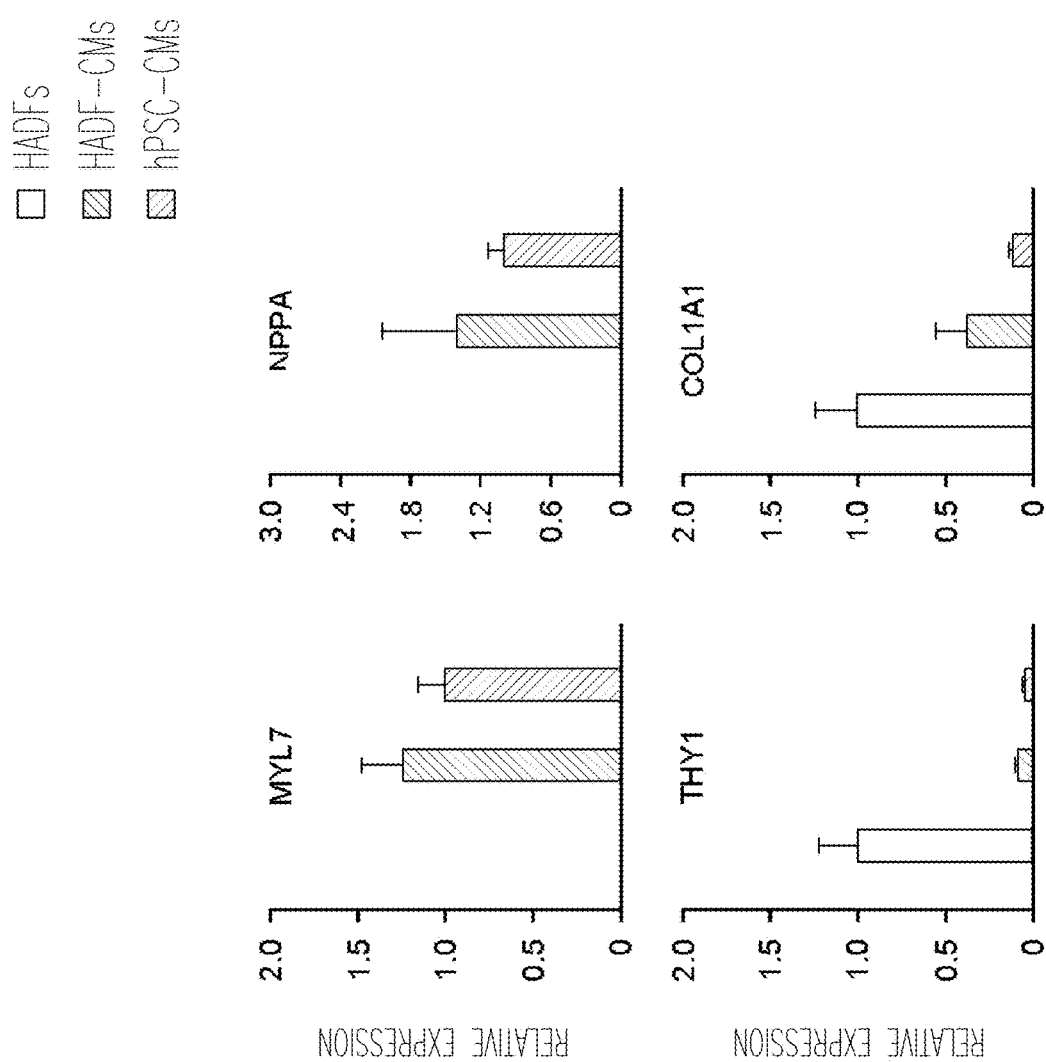

METHODS FOR REPROGRAMMING DIFFERENTIATED NON-CARDIAC CELLS INTO CARDIOMYOCYTES

CROSS REFERENCE TO RELATED APPLICATIONS

This application is a continuation-in-part under 35 U.S.C. § 1.111(a) of PCT application No. PCT/US2014/055083, filed Sep. 11, 2014, which claims the benefit of the priority filing date of U.S. Provisional patent Application Ser. No. 61/876,649, entitled "Small Molecule Cellular Reprogramming to Generate Cardiomyocytes," filed Sep. 11, 2013, the disclosures of which applications are incorporated herein by reference in their entireties.

SEQUENCE LISTING

This document incorporates by reference herein an electronic sequence listing text file, which is filed in electronic format via EFS-Web. The text file is named "1554750.TXT," is 12,288 bytes, and was created on Mar. 9, 2016.

BACKGROUND

The differentiated cell state is often considered stable and resistant to changes in lineage identity. However, differentiated somatic cell types from humans and other organisms have been reprogrammed to the pluripotent state ("pluripotent reprogramming") by forced expression of a set of transcription factors (Takahashi, K. et al. *Induction of pluripotent stem cells from adult human fibroblasts by defined factors*. Cell 131, 861-872 (2007)), somatic cell nuclear transfer (Campbell et al., *Sheep cloned by nuclear transfer from a cultured cell line*. Nature 380: 64-66 (1996); Gurdon et al., *Sexually mature individuals of Xenopus laevis from the transplantation of single somatic nuclei*, Nature 182, 64-65 (1958)) or cell fusion (Cowan et al., *Nuclear reprogramming of somatic cells after fusion with human embryonic stem cells*, Science (New York, N. 7309, 1369-1373 (2005); Tada et al., *Nuclear reprogramming of somatic cells by in vitro hybridization with ES cells*. Curr Biol 11, 1553-1558 (2001)).

Additionally, a few studies have demonstrated that through ectopic expression of selected genes or by cell fusion, an adult cell type can be directly converted to another adult cell type (Cobaleda et al., *Conversion of mature B cells into T cells by dedifferentiation to uncommitted progenitors*, Nature 449, 473-477 (2007); Davis et al., *Expression of a single transfected cDNA converts fibroblasts to myoblasts*, Cell 51, 987-1000 (1987); Feng, et al. *PU. 1 and C/EBPalpha/beta convert fibroblasts into macrophage-like cells*, Proc. Nat. Acad. Sci. USA 105, 6057-6062 (2008); Ieda et al. *Direct reprogramming of fibroblasts into functional cardiomyocytes by defined factors*, Cell 142, 375-386 (2010); Zhou et al., *In vivo reprogramming of adult pancreatic exocrine cells to beta-cells*, Nature 455, 627-632 (2008); and Zhou, Q. & Melton, D. A. *Extreme makeover: converting one cell into another*, Cell Stem Cell 3: 382-388 (2008)). This process is termed trans-differentiation or lineage reprogramming.

However, major challenges remain due to the low efficiency and slow reprogramming process. A more significant challenge is how to accomplish cell reprogramming without the need for genetic changes in the reprogrammed cells, because such genetic changes give rise to concerns about introduced mutations at the insertion site of expression cassettes encoding pluripotency and other factors.

SUMMARY

The compositions and methods described herein can accomplish reprogramming of differentiated, non-cardiac cells to generate cardiac progenitor cells and cardiomyocytes by chemical means and without the need for genetic engineering.

One aspect of the invention is a composition including one or more of the following agents: a WNT agonist, a GSK3 inhibitor, a TGF-beta inhibitor, an inhibitor of extracellular signal-regulated kinase 1 (ERK1), an inhibitor of Ras GTPase-activating protein (Ras-GAP)), an Oct-4 activator, a Rho-associated coiled coil forming protein serine/threonine kinase inhibitor, an iron chelator, a KDM5B inhibitor, a histone methyltransferase inhibitor, a PDGF tyrosine kinase inhibitor, or any combination thereof.

For example, the composition can include one or more of the following agents: CHIR99021(a GSK3 inhibitor), A83-01 (a TGF-beta inhibitor), SC1 (an inhibitor of extracellular signal-regulated kinase 1 (ERK1) and an inhibitor of Ras GTPase-activating protein (Ras-GAP)), OAC2 (an Oct-4 activator), Y27632 (a Rho-associated coiled coil forming protein serine/threonine kinase inhibitor), BIX-01294 (a histone methyltransferase inhibitor), AS8351 or PBIT (iron chelator and/or KDM5B inhibitor), SU16f (a PDGF receptor inhibitor), JNJ-10198409 (a PDGF tyrosine kinase inhibitor, or any combination thereof.

Such compositions can reprogram differentiated cells to the cardiac lineage. For example, the compositions can include at least two of the agents, or at least three of the agents, or at least four of the agents, or at least five of the agents, or at least six of the agents, or at least seven of the agents, or at least eight of the agents.

Other compositions are useful for maturation of cardiac progenitor cells. Another aspect of the invention is a composition that includes a GSK3 inhibitor, and at least two growth factors selected from the group consisting of BMP4, Activin A and VEGF.

Another aspect of the invention is a method of generating a cardiac progenitor cell or a cardiomyocyte. The method involves contacting a selected cell with a composition that includes one or more of the following agents: CHIR99021(a GSK3 inhibitor), A83-01 (a TGF-beta inhibitor), SC1 (an inhibitor of extracellular signal-regulated kinase 1 (ERK1) and an inhibitor of Ras GTPase-activating protein (Ras-GAP)), OAC2 (an Oct-4 activator), Y27632 (a Rho-associated coiled coil forming protein serine/threonine kinase inhibitor). BIX-01294 (a histone methyltransferase inhibitor), AS8351 or PBIT (iron chelator and/or KDM5B inhibitor), SU16f (a PDGF receptor inhibitor), JNJ-10198409 (a PDGF tyrosine kinase inhibitor, or any combination thereof, to thereby generate a cardiac progenitor cell or a cardiomyocyte. The method can further involve contacting the selected cell that has been treated with the reprogramming composition with another composition that includes a GSK3 inhibitor, and at least two growth factors selected from the group consisting of BMP4, Activin A and VEGF. The selected cell is a mixture or population of cells. The selected cell can be a differentiated, non-cardiac cell (or a mixture of differentiated, non-cardiac cells).

Another aspect of the invention is a method of treatment. Such a method can involve administering any of the compositions described herein to a subject. In another embodiment, the treatment method can involve administering one or more cardiac progenitor cells and/or cardiomyocytes to a subject, where the cardiac progenitor cells and/or the cardiomyocytes have been generated by use of the compositions and/or methods described herein. The method can include administration of combinations of the compositions described herein with cardiac progenitor cells and/or the cardiomyocytes generated as described herein.

DESCRIPTION OF THE FIGURES

The patent or application file contains at least one drawing executed in color. Copies of this patent or patent application publication with color drawing(s) will be provided by the Office upon request and payment of the necessary fee.

FIG. 4 shows that several major cardiac markers are expressed in cardiomyocyte cells reprogrammed from the human dermal fibroblast cell line CRL-2097 using the compositions and methods described herein. The cardiac-specific protein markers that were expressed included: α-Actinin, MLC2v, MY20, cMHC, NKX2-5, GATA4, cTNT, cTNI, and MLC2a.

FIG. 6A-6C illustrate the electrophysiological properties of cardiomyocyte cells reprogrammed from human dermal fibroblast cell line CRL-2097. FIG. 6A shows representative action potentials of fibroblasts reprogrammed into contracting cardiomyocytes after 37 days of treatment with the compositions and methods described herein. FIG. 6B shows representative $Ca^{2+}$ transients recorded from a fibroblast-derived contracting cardiomyocyte at day 37 after treatment of cells using the compositions and methods described herein. FIG. 6C summarizes the action potentials and $Ca^{2+}$ transients recorded from cardiomyocytes that were derived from fibroblasts by 32 to 37 days of treatment of the fibroblasts using the compositions and methods described herein.

FIG. 7A illustrates the beating frequency of cardiomyocytes generated as described herein after treatment with a β-adrenergic agonist (isoproterenol) or a muscarinic agonist (carbachol; CCh). FIG. 7B shows spontaneous $Ca^{2+}$ transients recorded from fibroblast-derived cardiomyocytes before or after β-adrenergic stimulation by its agonist, isoproterenol, as well as the muscarinic agonist, Cch. The (i) time period responses were recorded from cardiomyocytes in the absence of β-adrenergic and muscarinic agonists; the (ii) time period responses were recorded from cardiomyocytes in the presence of the β-adrenergic agonist isoproterenol; and the (iii) time period responses were recorded from cardiomyocytes in the presence of muscarinic agonist carbachol (CCh).

FIG. 8A graphically illustrates the knockdown efficiency of the indicated shRNAs in human foreskin fibroblast cells detected by qPCR (n=2). Expression values for each gene were normalized to those measured in control shRNA group. FIG. 8B shows the number of beating clusters per $3 \times 10^6$ cells when knocking down expression of the indicated genes in the absence of AS8351 in the reprogramming culture medium (*P<0.05 vs. control). Data were collected on day 30. FIG. 8C shows the number of beating clusters per $3 \times 10^6$ cells upon incubation of the cells in the KDM5B inhibitor PBIT in the absence of AS8351 in the reprogramming culture medium (n=3). The number of beating clusters was used as a measure of the generation of chemically induced cardiomyocytes (n=3; *P<0.05 vs. DMSO). Data were collected on day 30. FIG. 8D illustrates the reprogramming efficiencies by day 30 of indicated conditions as revealed by FACS analysis of cTNT expression (n=3). FIG. 8E illustrates immunofluorescence staining of cardiomyocyte markers on contracting clusters at day 30 after inducing reprogramming where AS8351 was replaced with 10 μM PBIT. Scale bars, 100 μm. FIG. 8F shows representative traces of synchronized action potentials and $Ca^{2+}$ transients in chemically induced cardiomyocytes generated by replacing AS8351 with 10 μM PBIT. $E_m$, membrane potential. Dotted lines indicate 0 mV. F/F0, fluorescence relative to the baseline. FIG. 8G shows the action potential and $Ca^{2+}$ transient parameters of the chemically induced cardiomyocytes generated as described FIG. 8F.

FIG. 9A-9E illustrates pharmacological conversion of human adult dermal fibroblasts (HADFs) into chemically induced cardiomyocytes. FIG. 9A shows a schematic diagram of the protocol used for chemically inducing cardiomyocyte generation from HADFs. 9C is the reprogramming conditions; CCM. CM-conditioned medium; D, day. FIG. 9B illustrates the effects on beating cluster induction when HADFs were individually or combinatorially treated with sodium butyrate (NaB or N) and/or SMER28 (S) from day −7 to 0 (n=3). FIG. 9C graphically illustrates test protocols for ascertaining optimal treatment durations for a combination of sodium butyrate and SMER28 (NS) (n=3). The duration shown on the x-axis of the left graph is days (e.g., D0=day zero; D-14=day 14 of treatment). FIG. 9D shows representative and summary FACS results of cTNT expression on HADFs after the treatments indicated in FIG. 9A (n=3). FIG. 9E illustrates expression of cardiomyocyte markers on day 30 of chemical induction to generate cardiomyocytes from HADFs, as detected by immunofluorescent staining. Scale bars, 100 μm.

FIG. 10A-10G1-G2 shows results illustrating the characteristics of chemically induced cardiomyocytes (ciCMs) that were converted from HADFs. FIG. 10A illustrates expression of cardiomyocyte markers by ciCMs derived from HADFs (HADF-CMs) at day 30 of treatment, as detected by immunofluorescence staining. Scale bars, 25 μm. FIG. 10E shows Action Potential and $Ca^{2+}$ transient parameters of HADF-CMs, including beating frequency (BF), maximum upstroke velocity (Vmax), maximum diastolic potential (MDP), overshoot potential (OSP), Action Potential duration at 90% repolarization (APD90), Ca2+ transient amplitude (F/F0) and duration from 10-90% of Ca2+ transient peak (T10-90%). FIGS. 10G1 and 10G2 illustrate expression levels of key cardiomyocyte or fibroblast markers as detected by quantitative RT-PCR (n=3).

DETAILED DESCRIPTION

Figure 1:
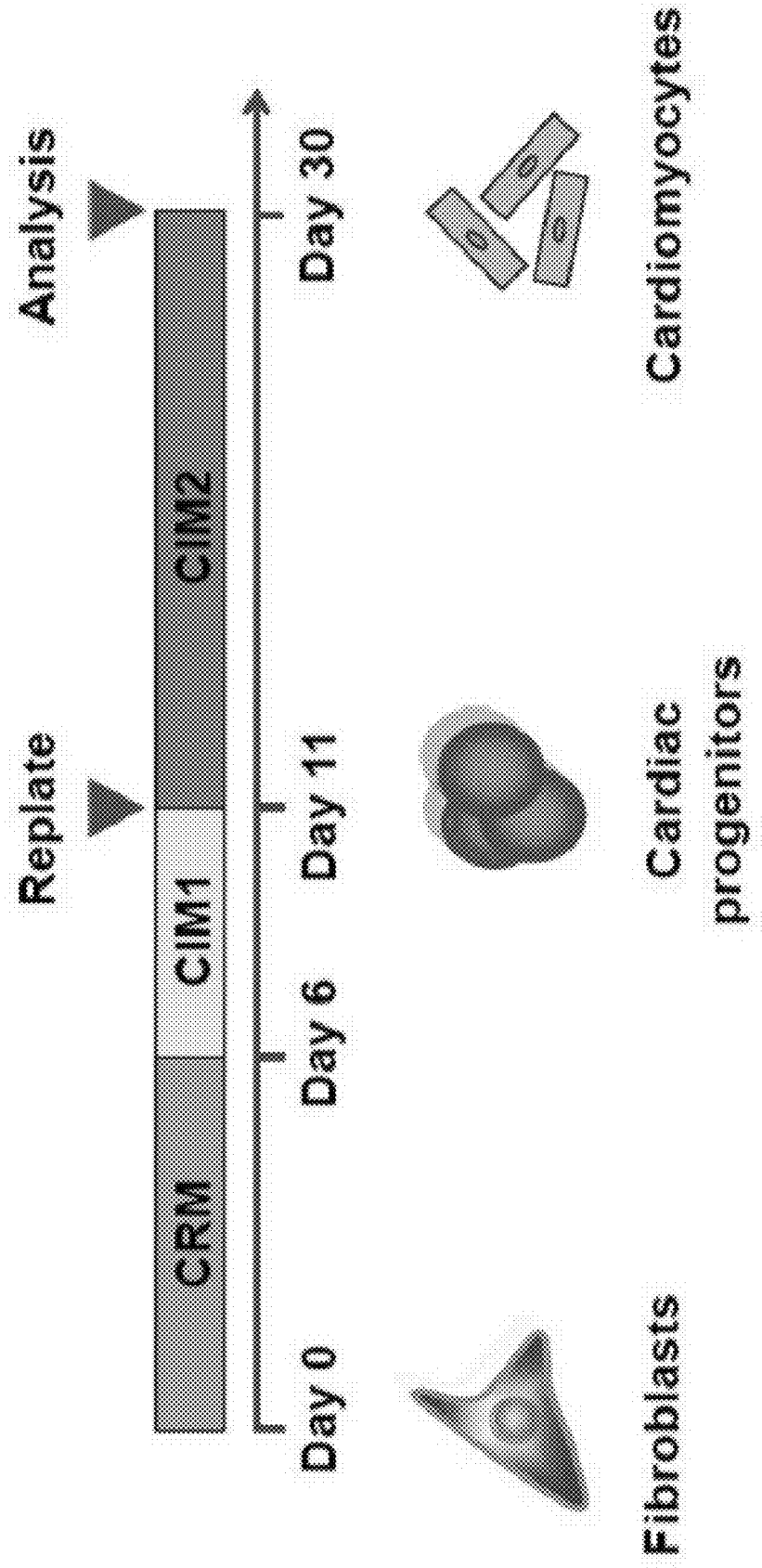
FIG. 1 is a schematic diagram illustrating generation of human cardiomyocytes from starting cells (e.g., fibroblast cells) though treatment with (1) cardiac reprogramming medium (CRM) over 6 days to initiate cell fate conversion followed by (2) exposure to cardiac induction medium 1 (CIM1) for 5 days, and then cardiac induction medium 2 (CIM2) for 30 days or more. The cardiac induction medium used for these experiments contained a combination of nine small-molecule compounds including: CHIR99021, A83-01, SC1, OAC2, Y27632, BIX-01294, AS8351, SU16f, and JNJ-10198409. This cardiac induction composition is also referred to as the 9C composition.

As described herein, differentiated mammalian cells can be reprogrammed to cross lineage boundaries and to directly convert to another cell type, for example a cardiac progenitor cell type or a cardiomyocyte, without genetic manipulation. Instead a differentiated non-cardiac cell can simply be treated with a composition of chemical compounds to change that cell into a cardiac progenitor cell type or a cardiomyocyte.

Heart development is a well-organized process that involves the sequential induction of mesoderm, multipotent cardiac progenitor cells and functional derivatives. Cardiac progenitor cells are already committed and are capable of differentiation into multiple lineages of the heart without teratoma-forming ability, thus they offer an appealing alternative cell source for myocardial regeneration.

Reprogramming

Although one or more recombinantly introduced transcription factors can be used if desired, differentiated mammalian cells can be converted into the cardiac cell lineage without such genetic manipulation. Instead, a composition of chemical compounds can be administered to a subject, or differentiated (e.g., non-cardiac) cells from the subject can be incubated with such a composition to convert the subject's cells to a cardiac progenitor cell type or a cardiomyocyte.

A reprogramming composition can be employed that contains one or more of the following chemical agents: a GSK3 inhibitor, a WNT agonist, a TGF-beta inhibitor, an inhibitor of extracellular signal-regulated kinase 1 (ERK1), an inhibitor of Ras GTPase-activating protein (Ras-GAP), an Oct-4 activator, a Rho-associated coiled coil forming protein serine/threonine kinase inhibitor, an iron chelator and/or KDM5B inhibitor, an inhibitor of G9a histone methyltransferase, an inhibitor of various growth factor receptors such as PDGF receptor beta, a protein kinase receptor inhibitor, an inhibitor of PDGF-BB receptor, and any combination thereof.

These compounds are described in more detail below.

WNT Agonists

Approximately twenty WNT proteins have been identified in mammals. Examples of WNT proteins include WNT1, WNT2, WNT2b/13, WNT3, WNT3a, WNT4, WNT5a, WNT5b, WNT6, WNT7a, WNT7b, WNT7c, WNT8, WNT8a, WNT8b, WNT8c, WNT10a, WNT10b, WNT11, WNT14, WNT15, or WNT16. WNT proteins are secreted, cysteine-rich proteins.

The WNT signaling pathway includes a series of events that occur when a WNT protein binds to a cell-surface receptor of a Frizzled receptor family member. This results in the activation of Dishevelled family proteins which inhibit a complex of proteins that includes axin, GSK-3, and the protein APC that normally degrade intracellular beta-catenin. The resulting enriched nuclear beta-catenin enhances transcription by TCF/LEF family transcription factors. A WNT agonist can therefore include an agent that activates TCF/LEF-mediated transcription in a cell. WNT agonists can be selected from true WNT agonists that bind and activate a Frizzled receptor family member including any and all of the WNT family proteins, an inhibitor of intracellular beta-catenin degradation, activators of TCF/LEF, and inhibitors of GSK-3.

Activation of the WNT pathway leads to inhibition of GSK3, subsequent nuclear accumulation of β-catenin and the expression of target genes. WNT agonists can include WNT-3a, a GSK-inhibitor (such as any of those described herein), WNT 5, WNT-6a, Norrin, and any other WNT family protein.

For example, a WNT agonist can include a secreted glycoprotein including WNT-1/Int-1, WNT-2/Irp (InM-related Protein), WNT-2b/13, WNT-3/Int-4, WNT-3a (R&D Systems), WNT-4, WNT-5a, WNT-5b, WNT-6 (Kirikoshi et al., *Biochem Biophys Res Comm* 283: 798-805 (2001)), WNT-7a (R&D systems), WNT-7b, WNT-8a/8d, WNT-8b, WNT-9a/14, WNT-9b/14b/15, WNT-10a, WNT-10b/12, WntM 1, and WNT-16. An overview of human WNT proteins is provided in "THE WNT FAMILY OF SECRETED PROTEINS", R&D Systems Catalog, 2004. Other WNT agonists include the R-spondin family of secreted proteins, which is implicated in activation and regulation of WNT signaling pathways, and which is comprised of 4 members (R-spondin 1 (NU206, Nuvelo, San Carlos, Calif.), R-spondin 2 (R&D systems), R-spondin 3, and R-spondin-4), and Norrin (also called Nome Disease Protein or NDP) (R&D systems), which is a secreted regulatory protein that functions like a WNT protein in that it binds with high affinity to the Frizzled-4 receptor and induces activation of the WNT signaling pathway (Kestutis Planutis et al., BMC Cell Biol 8-12 (2007)). In some embodiments, one or more WNT agonists can include an R-spondin mimic, for example an agonist of Lgr5 such as an anti-Lgr5 antibody. A small-molecule agonist of the WNT signaling pathway, an aminopyrimidine derivative, was recently identified and is also expressly included as a WNT agonist (Lin et al. *Angew Chem Int Ed Engl* 44, 1987-90 (2005)).

In some embodiments, the WNT agonist is a GSK-inhibitor.

One or more WNT agonists can be included in a composition for treatment of subject. Alternatively, one or more WNT agonists can be included in a cell medium useful for reprogramming a differentiated cell into a cardiac cell type, such as a cardiomyocyte.

The WNT agonists can be employed in the compositions and methods described herein in a variety of amounts and/or concentrations. For example, the WNT agonists can be employed in solution at a concentration of about 0.01 micromolar to about 20 millimolar, or about 0.1 micromolar to about 100 micromolar, or about 1 micromolar to about 50 micromolar. In a dry formulation, the WNT agonists can be present in amounts of about 0.01 mg to about 100 mg, or about 0.05 mg to about 10 mg, or about 0.1 mg to about 1.0 mg.

GSK3 Inhibitors

Glycogen synthase kinase 3 (GSK3) is serine/threonine protein kinase that catalyzes the addition of phosphate molecules on certain serine and threonine amino acid residues in target protein substrates within cells. Phosphorylation of such target protein substrates often results in the modification of their specific activities or function.

As illustrated herein GSK3 inhibitors can facilitate reprogramming of differentiated cells to the cardiac cell lineage. Examples of GSK3 inhibitors that can be employed include one or more of the following compounds;

CHIR99021 (6-(2-(4-(2,4-dichlorophenyl)-5-(4-methyl-1H-imidazol-2-yl)pyrimidin-2-ylamino)ethylamino)nicotinonitrile);
1-azakenpaullone (9-Bromo-7,12-dihydro-pyrido[3',2':2,3] azepino[4,5-b]indol-6(5H)-one), BIO ((2'Z,3'E)-6-Bromoindirubin-3'-oxime);
AR-A014418 (N-(4-Methoxybenzyl)-N'-(5-nitro-1,3-thiazol-2-yl)urea);
Indirubin-3'-monoxime;
5-Iodo-indirubin-3'-monoxime;
kenpaullone (9-Bromo-7,12-dihydroindolo-[3,2-d][1]benzazepin-6(5H)-one);
SB-415286 (3-[(3-Chloro-4-hydroxyphenyl)amino]-4-(2-nitro-phenyl)-1H-pyrrole-2,5-dione);
SB-216763 (3-(2,4-Dichlorophenyl)-4-(1-methyl-1H-indol-3-yl)-1H-pyrrole-2,5-dione);
Maybridge SEW00923SC (2-anilino-5-phenyl-1,3,4-oxadiazole);
(Z)-5-(2,3-Memylenedioxyphenyl)imidazolidine-2,4-dione;
TWS119 (3-(6-(3-aminophenyl)-7H-pyrrolo[2,3-d]pyrimidin-4-yloxy)phenol);
CHIR98014 (N2-(2-(4-(2,4-dichlorophenyl)-5-(1H-imidazol-1-yl)pyrimidin-2-ylamino)ethyl)-5-nitropyridine-2,6-diamine);
SB415286 (3-(3-chloro-4-hydroxyphenylamino)-4-(2-nitrophenyl)-1H-pyrrole-2,5-dione);
Tideglusib (also known as NP031112, or NP-12; 1,2,4-Thiadiazolidine-3,5-dione, 2-(1-naphthalenyl)-4-(phenylmethyl));
LY2090314 (1H-Pyrrole-2,5-dione, 3-imidazo[1,2-a]pyridin-3-yl-4-[1,2,3,4-tetrahydro-2-(1-piperidinylcarbonyl) pyrrolo[3,2,1-jk][1,4]benzodiazepin-7-yl]);
lithium salt (e.g., LiCl); or
any combination thereof.

GSK-inhibitors can also include small-interfering RNAs (siRNA. Cell Signaling), lithium (Sigma), kenpaullone (Biomol International, Leost, Metal (2004) *Eur J Biochem* 267, 5983-5994), 6-Bromoindirubin-30-acetoxime (Meyer, L et al (2003) *Chem Biol* 10, 1255-1266), SB 216763 and SB 415286 (Sigma-Aldrich), and FRAT-family members and FRAT-derived peptides that prevent interaction of GSK-3 with axin. An overview is provided by Meijer et al, (2004) *Trends in Pharmacological Sciences* 25, 471-480, which is hereby incorporated by reference in its entirety. GSK3 inhibitors that can be used in the compositions and methods described herein can also include those disclosed in US 20120329152 by Pera et al., which is specifically incorporated herein in its entirety.

The GSK3 inhibitor can, for example, be CHIR99021, SB216763, TWS119, CHIR98014, Tideglusib, SB415286, LY2090314, or any combination thereof. In some embodiments, the GSK3 inhibitor can be CHIR99021, whose structure is shown below.

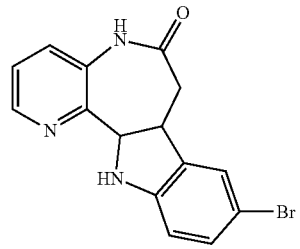 [SMILES: O=C1CC2c3cc(Br)ccc3NC2c2ncccc2N1]

The GSK3 inhibitors can also be in the form of a salt or hydrate of any of the foregoing compounds.

The GSK3 inhibitors can be employed in the compositions and methods described herein in a variety of amounts and/or concentrations. For example, the GSK3 inhibitor can be employed in a solution at a concentration of about 0.01 micromolar to about 20 millimolar, or about 0.1 micromolar to about 100 micromolar, or about 1 micromolar to about 50 micromolar. In a dry formulation, the GSK3 inhibitor can be present in amounts of about 0.01 mg to about 100 mg, or about 0.05 mg to about 10 mg, or about 0.1 mg to about 1.0 mg.

Methods and assays for determining a level of GSK-3 inhibition are available to a skilled person and include, for example, the methods and assays described in Liao et al., *Endocrinology*, 145(6): 2941-2949 (2004); and in U.S. Pat. No. 8,323,919, both of which are specifically incorporated by reference herein in their entireties.

TGF-beta Inhibitors

As illustrated herein use of one or more transforming growth factor-beta (TGF-β) inhibitors can facilitate conversion of differentiated cells into the cardiac cell lineage.

There are about thirty members of the transforming growth factor-beta (TGF-β) superfamily, including Activin, Nodal, and BMPs. These TGF-β family members elicit their responses through a variety of cell surface receptors that activate Smad protein signaling cascades.

A TGF-beta inhibitor can directly or indirectly, negatively regulate TGF-beta signaling. In some embodiments, one or more TGF-beta inhibitors binds to and reduces the activity of one or more serine/threonine protein kinases selected from the group consisting of ALK5, ALK4, TGF-beta receptor kinase 1 and ALK7. ALK4, ALK5 and ALK7 are all closely related receptors of the TGF-beta superfamily. Desirable TGF-beta inhibitors can bind to and reduce the activity of ALK4. ALK5 (TGF-beta receptor kinase 1) and/or ALK7. In another embodiment, the TGF-beta receptor binds to and reduces the activity of a Smad protein, for example R-SMAD or SMAD1-5 (i.e. SMAD 1, SMAD 2, SMAD 3, SMAD 4 or SMAD 5).

Examples of TGF-B inhibitors include, but are not limited to:

3-(6-Methyl-2-pyridinyl)-N-phenyl-4-(4-quinolinyl)-1H-pyrazole-1-carbothioamide (also known as A83-01, and available from Tocris Bioscience), which is a TGFβ kinase/Activin receptor like kinase (ALK5) inhibitor that blocks the phosphorylation of Smad2 and inhibits TGFβ-induced epithelial-to-mesenchymal transition;

4-[4-(1,3-benzodioxol-5-yl)-5-(2-pyridinyl)-1H-imidazol-2-yl]benzamide (also known as SB 431542 and available from Tocris Bioscience; a potent and selective inhibitor of TGF-β type I receptor Activin receptor-like kinase ALK5 (e.g., with $IC_{50}$=94 nM), and its relatives ALK4 and ALK7);

3-(6-Methyl-2-pyridinyl)-N-phenyl-4-(4-quinolinyl)-1H-pyrazole-1-carbothioamide (also known as A83-01 from Tocris Bioscience; a selective inhibitor of TGF-β type I receptor ALK5 kinase, type I Activin/nodal receptor ALK4 and type I nodal receptor ALK7 (IC50 values can be about 12, 45 and 7.5 nM respectively);

2-(3-(6-Methylpyridine-2-yl)-1H-pyrazol-4-yl)-1,5-naphthyridine (also known as SJN 2511 from Tocris Bioscience; selective inhibitor of the TGF-β type I receptor ALK5 (IC50 values can, e.g., be 0.004 and 0.023 μM for ALK5 autophosphorylation and ALK5 binding, respectively);

4-[4-(2,3-Dihydro-1,4-benzodioxin-6-yl)-5-(2-pyridinyl)-1H-imidazol-2-yl]benzamide (also known as D 4476 from Tocris Bioscience; a selective inhibitor of casein kinase 1 (CK1) and TGF-β type-1 receptor (ALK5) that displays greater than 20-fold selectivity over SAPK2/p38);

4-[3-(2-Pyridinyl)-1H-pyrazol-4-yl]-quinoline (also known as LY 364947 from Tocris Bioscience; a selective inhibitor of TGF-β type-I receptor (TGF-β R1, TGFR-I, TβR-1, ALK-5) (IC50 values can, e.g., be 59, 400 and 1400 nM for TGR-β RI, TGF-β RII and MLK-7K respectively);

2-(4-(benzo[d][1,3]dioxol-5-yl)-2-tert-butyl-1H-imidazol-5-yl)-6-methylpyridine (also known as SB505124, and available from Selleckchem.com; a selective inhibitor of ALK4 and ALK5 (e.g., with IC50 of 129 nM and 47 nM, respectively);

6-[2-(1,1-Dimethylethyl)-5-(6-methyl-2-pyridinyl)-1H-imidazol-4-yl]quinoxaline (also known as SB 525334 from Sigma-Aldrich; a selective inhibitor of transforming growth factor-β receptor 1 (ALK5, TGF-βRI), with IC50=14.3 nM, for example);

2-(5-Chloro-2-fluorophenyl)-4-[(4-pyridyl)amino]pteridine (also known as SD 208 from Tocris Bioscience; a potent, orally active ATP-competitive transforming growth factor-β receptor 1 (TGF-βRI) inhibitor, e.g., with IC50=49 nanomolar);

4-(6-(4-(piperazin-1-yl)phenyl)pyrazolo[1,5-a]pyrimidin-3-yl)quinoline (also known as LDN-193189 from Miltenyi Biotec); and any combination thereof.

The inhibitor that directly or indirectly negatively regulates TGF-beta signaling can, for example, be selected from the group consisting of A83-01, SB-431542, A83-01, SJN-2511, LY-36494, SB-505124, SB-525334, and SD-208. In some embodiments, an inhibitor that directly or indirectly negatively regulates TGF-beta signaling can inhibit ALK4, ALK5 and/or ALK7. For example, the inhibitor that directly or indirectly negatively regulates TGF-beta signaling can be A83-01 (structure shown below).

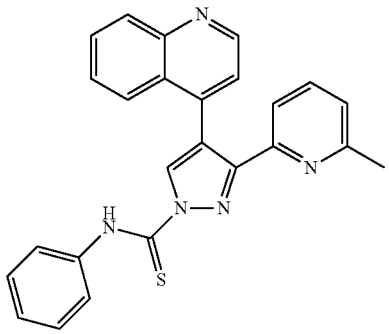 [SMILES: Cc1cccc(-c2nn(C(=S)Nc3ccccc3)cc2-c2ccnc3ccccc23)n1]

The TGF-beta inhibitor can also be in the form of a salt or hydrate of any of the foregoing compounds.

The TGF-beta inhibitor can be employed in the compositions and methods described herein in a variety of amounts and/or concentrations. For example, the TGF-beta inhibitor can be employed in a solution at a concentration of about 0.001 micromolar to about 20 millimolar, or about 0.01 micromolar to about 100 micromolar, or about 0.05 micromolar to about 10 micromolar. In a dry formulation, the TGF-beta inhibitor can be present in amounts of about 0.01 mg to about 200 mg, or about 0.05 mg to about 100 mg, or about 0.1 mg to about 20 mg.

Various methods for determining if a substance is a TGF-beta inhibitor are known. For example, a cellular assay may be used, in which cells are stably transfected with a reporter construct comprising the human PAI-1 promoter or Smad binding sites, driving a luciferase reporter gene. Inhibition of luciferase activity relative to control groups can be used as a measure of compound activity (De Gouville et al., *Br J Pharmacol.* 2005 May; 145(2): 166-177). Another example is the AlphaScreen® phosphosensor assay for measurement of kinase activity (Drew A E et al., Comparison of 2 Cell-Based Phosphoprotein Assays to Support Screening and Development of an ALK Inhibitor, *J Biomol Screen* 16(2) 164-173, 2011).

Inhibitors of Extracellular Signal-regulated Kinase 1 (ERK1)

As illustrated herein use of one or more ERK1 inhibitors can facilitate conversion of differentiated cells into the cardiac cell lineage.

ERK1 is an enzyme, a 44-kDa Ser/Thr kinase, which takes part in the Ras-Raf-ERK signal transduction cascade, and is activated in response to numerous growth factors and cytokines. ERK1 translocates into the nucleus where it phosphorylates various transcription factors. ERK1 is expressed in the highest amounts in the heart, brain and spinal cord of mammals.

Inhibitors of ERK1 include, but are not limited to, the following:

SC1 (also known as Pluripotin; N-(3-(7-(1,3-dimethyl-1H-pyrazol-5-ylamino)-1-methyl-2-oxo-1,2-dihydropyrimido[4,5-d]pyrimidin-3(4H)-yl)-4-methylphenyl)-3-(trifluoromethyl)benzamide, available from Cayman Chemical), and which is an inhibitor of RasGAP and ERK1 with Kd values of 98 and 212 nM, respectively;

Chromone (also known as 4H-1-Benzopyran-4-one, 4H-Chromen-4-one, 1-Benzopyran-4-one, Benzo-gamma-pyrone, Chromen-4-one, 491-38-3, 4H-Benzo(b)pyran-4-one);

PD 98059 (also known as 167869-21-8, PD-98059, PD 98,059, 2-(2-Amino-3-methoxyphenyl)-4H-1-benzopyran-4-one, PD98059, 2-(2-Amino-3-methoxyphenyl)- chromen-4-one), a highly selective inhibitor of MEK1 and MEK2 with IC50 values of 4 μM and 50 μM respectively (Runden E et al, *J Neurosci* 1998, 18(18) 7296-305), and available from Tocris Biosciences;

PD0325901 (also known as 391210-10-9, PD0325901, PD-0325901, S1036_Selleck, PD325901, PD0325901, PD-325901, CHEMBL507361, ZINC03938683; N-[(2R)-2,3-dihydroxypropoxy]-3, 4-difluoro-2-(2-fluoro-4-iodoanilino)benzamide), and available from Pfizer;

Selumetinib (also known as AZD6244, 606143-52-6, AZD-6244, ARRY-142886), a selective MEK inhibitor available from AstraZeneca/Array BioPharma;

ARRY-438162 (also known as 606143-89-9, MEK162, ARRY-162; ARRY-438162; MEK 162; ARRY 162; ARRY 438162, cc-455, MEK 162, MEK-162, ARRY-162, MEK-162, ARRY 438162, 6-(4-bromo-2-fluoroanilino)-7-fluoro-N-(2-hydroxyethoxy)-3-methylbenzimidazole-5-carboxamide) available from Array BioPharma;

PD198306 (also known as 212631-61-3, CTK8E9262, HMS3229H15, HMS3269F09, NCGC00167793-01, LS-191027, BRD-K88677950-001-01-3, N-(cyclopropylmethoxy)-3,4,5-trifluoro-2-(4-iodo-2-methylanilino)benzamide) available from Pfizer;

PD0325901 (also known as 391210-10-9, PD0325901, PD-0325901, S1036_Selleck, PD325901, PD 325901, PD-325901, CHEMBL507361, ZINC03938683; N-[(2R)-2,3-dihydroxypropoxy]-3,4-difluoro-2-(2-fluoro-4-iodoanilino)benzamide) available from Pfizer;

AZD8330 (also known as AZD-8330, ARRY-704, 869357-68-6, AZD8330, ARRY-424704, ARRY-704, AZD-8330, S2134_Selleck, ARRY704, UNII-G4990BOZ66, ARRY424704, BCPP000359, 2-(2-fluoro-4-iodoanilino)-N-(2-hydroxyethoxy)-1,5-dimethyl-6-oxopyridine-3-carboxamide) available from AstraZeneca/Array Biopharma;

PD 184352 (also known as CI-1040, 212631-79-3, PD184352, PD-184352, AG-E-55891, 2-(2-chloro-4-iodoanilino)-N-(cyclopropylmethoxy)-3,4-difluorobenzamide) with a Kd, for example, of about 10 μM, and available from Pfizer;

PD 184161 (also known as 212631-67-9, PD-184161, CTK8E9263, HMS3263A07, UK-287074, PF-1529483, PF-3011370, 5-bromo-2-(2-chloro-4-iodoanilino)-N-(cyclopropylmethoxy)-3,4-difluorobenzamide) available from Pfizer;

SL 327 (also known as SL327, MEK1/2 Inhibitor, SL-327, CHEMBL261237, 305350-87-2, (Z)-3-amino-3-(4-aminophenyl)sulfanyl-2-[2-(trifluoromethyl)phenyl]prop-2-enenitrile) available from Tocris Bioscience;

1,4-Diamino-2,3-dicyano-1,4-bis(2-aminophenylthio)butadiene (DeSilva, D. R., et al., *J. Immunol.* 160(9): 4175 (1998); Duncia, J. V., et al. *Biorg. Med. Chem. Lett.* 8(20): 2839 (1998); Favata, et al. *J. Biol. Chem.* 273(29): 18623 (1998);

U0126 (also known as CHEBI:64208, 109511-58-2, (2Z, 3Z)-2,3-bis[amino-(2-aminophenyl)sulfanylmethylidene]butanedinitrile), see Kohno & Pouyssegur, *Prog. Cell. Cyc. Res.* 5: 219-224 (2003);

GW 5074 (also known as gw5074, Raf1 Kinase Inhibitor 1, InSolution™ Raf1 Kinase Inhibitor I, (3Z)-3-[(3,5-dibromo-4-hydroxyphenyl)-methylidene]-5-iodo-1H-indol-2-one) available from Santa Cruz Biotechnology;

BAY 43-9006 (also known as Sorafenib, Nexavar, 284461-73-0, sorafenibum, Sorafenib [INN], Kinome_766, UNII-9ZOQ3TZI87, AC1L50CF, BAY-43-9006, CHEMBL1336, 4-[4-[[4-chloro-3-(trifluoromethyl)phenyl]carbamoylamino]phenoxy]-N-methylpyridine-2-carboxamide) available from Bayer, Ro 09-2210 with an IC50 of about 50 to 70 nmol/L, see, Williams et al, *Biochemistry* 37(26):9579-85 (1998), available from Roche Products Ltd;

FR 180204 (also known as ERK Inhibitor II, FR180204, FR-180204, 5-(2-phenylpyrazolo[1,5-a]pyridin-3-yl)-2H-pyrazolo[3,4-c]pyridazin-3-amine) see, Ohori et al. *Biochem. Biophys. Res. Comm.* 336: 357-363 (2005);

PKI-ERK-005 (also known as 3-(2-aminoethyl)-5-))4-ethoxyphenyl)methylene)-2,4-thiazolidinedione), see, Chen, *Bioorg. Med. Chem.* 16:6281-6288 (2006), Hancock et al. *J. Med Chem.* 48: 4586-4595 (2005);

CAY10561 (also known as N-[1-(3-chloro-4-fluorophenyl)-2-hydroxyethyl]-4-[4-(3-chlorophenyl)pyrazolidin-3-yl]-1H-pyrrole-2-carboxamide) available from Cayman Chemical (CAS 933786-58-4);

GSK 120212 available from GlaxoSmithKline;

RDEA119 (also known as N-[3,4-difluoro-2-(2-fluoro-4-iodoanilino)-6-methoxyphenyl]-1-[(2S)-2,3-dihydroxypropyl]cyclopropane-1-sulfonamide (Ardea Biosciences), XL518 (also known as GDC 0973, CHEMBL2146883, XL 518, 934660-93-2, GDC0973, Cobimetinib, 4-difluoro-2-(2-fluoro-4-iodoanilino)-phenyl]-[3-hydroxy-3-[(2S)-piperidin-2-yl]azetidin-1-yl]methanone);

ARRY-704 (also known as AZD-8330, 869357-68-6, AZD8330, ARRY-424704, ARRY-704, AZD-8330, S2134_Selleck, ARRY704, UNII-G4990BOZ66, ARRY424704, BCPP000359, 2-(2-fluoro-4-iodoanilino)-N-(2-hydroxyethoxy)-1,5-dimethyl-6-oxopyridine-3-carboxamide) (AstraZeneca); and any combination thereof.

Other ERK inhibitors and their synthesis methods have been described in U.S. Pat. No. 5,525,625, WO 2012160130, WO 98/43960, WO 99/01426, WO 00/41505, WO 00/42002, WO 00/42003, WO 00/41994, WO 00/42022; WO 00/42029, WO 00/68201; WO 01/68619; WO 02/06213; WO 03/077855 and WO 2005/23251.

The ERK1 inhibitor can also be in the form of a salt or hydrate of any of the foregoing compounds. Any of the ERK inhibitors described herein can be used in the compositions and/or methods provided herein.

In some embodiments, the ERK1 inhibitor is SC1 (also known as Pluripotin). Selumetinib (also known as AZD6244), U0126, PD98059, PD0325901, AZD8330, CI-1040, PD318088, or any combination thereof. For example, the ERK1 inhibitor can be SC1 (also known as Pluripotin), whose structure is shown below.

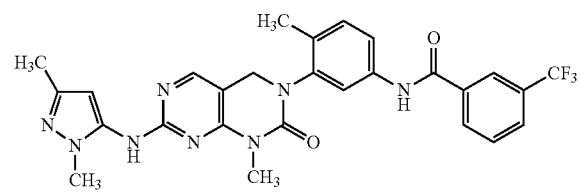 [SMILES: Cc1cc(Nc2ncc3c(n2)N(C)C(=O)N(c2cc(NC(=O)c4cccc(C(F)(F)F)c4)ccc2C)C3)n(C)n1]

The ERK1 inhibitor can be employed in the compositions and methods described herein in a variety of amounts and/or concentrations. For example, the ERK1 inhibitor can be employed in a solution at a concentration of about 0.001 micromolar to about 20 millimolar or about 0.01 micromolar to about 100 micromolar, or about 0.05 micromolar to about 10 micromolar. In a dry formulation, the ERK1 inhibitor can be present in amounts of about 0.01 mg to about 200 mg, or about 0.05 mg to about 100 mg, or about 0.1 mg to about 20 mg.

Inhibitors of Ras GTPase-activating Protein (Ras-GAP)

As illustrated herein use of one or more Ras GTPase-activating protein inhibitors can facilitate conversion of differentiated cells into the cardiac cell lineage.

Ras proteins are membrane-associated molecular switches that bind GTP and GDP and slowly hydrolyze GTP to GDP. This intrinsic GTPase activity of ras is stimulated by a family of proteins collectively known as GTPase-activating proteins. Ras GTPase-activating proteins are quite large (from 765 residues for sar1 to 3079 residues for IRA2) but share only a limited (about 250 residues) region of sequence similarity, referred to as the 'catalytic domain' or rasGAP domain.

Inhibitors of Ras GTPase-activating proteins include, but are not limited to SC1 (also known as Pluripotin; N-(3-(7-(1,3-dimethyl-1H-pyrazol-5-ylamino)-1-methyl-2-oxo-1,2-dihydropyrimido[4,5-d]pyrimidin-3(4H)-yl)-4-methylphenyl)-3-(trifluoromethyl)benzamide, available from Cayman Chemical), and which is an inhibitor of RasGAP and ERK1 with Kd values of 98 and 212 nM, respectively.

Inhibitors of Ras GTPase-activating proteins can also be in the form of a salt or hydrate of any of the foregoing compounds.

Inhibitors of Ras GTPase-activating proteins can be employed in the compositions and methods described herein in a variety of amounts and/or concentrations. For example, the ERK1 inhibitor can be employed at a concentration of about 0.01 micromolar to about 20 millimolar in a solution. In a dry formulation, the ERK1 inhibitor can be present in amounts of about 0.01 mg to about 200 mg, or about 0.05 mg to about 100 mg, or about 0.1 mg to about 20 mg.

Oct-4 Activators

As illustrated herein use of one or more Oct-4 activators can facilitate conversion of differentiated cells into the cardiac cell lineage.

One type of Oct-4 activator that can be used in the methods and compositions described herein is OAC2 (also known as (E)-N'-((2-hydroxynaphthalen-1-yl)methylene) isonicotino-hydrazide, whose structure is shown below.

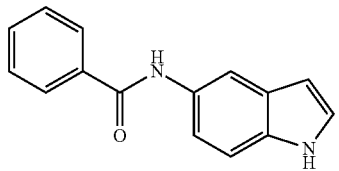 [SMILES: O=C(Nc1ccc2[nH]ccc2c1)c1ccccc1]

OAC2 activates Oct-4 expression through the Oct-4 promoter (see, e.g., Li et al., Proc. Natl. Acad. Sci. USA 109(51): 20853-58 (2012). OAC2 can enhance production of induced pluripotent stem cells from embryonic fibroblasts (id.). The Oct-4 activator(s) can also be in the form of a salt or hydrate of any of the foregoing compounds.

One or more Oct-4 activators can be employed in the compositions and methods described herein in a variety of amounts and/or concentrations. For example, the Oct-4 activators can be employed at a concentration of about 0.01 micromolar to about 20 millimolar in a solution, or about 0.1 micromolar to about 1 millimolar in a solution, or about 1 micromolar to about 20 micromolar in a solution. In a dry formulation, the Oct-4 activator can be present in amounts of about 0.01 mg to about 200 mg, about 0.05 mg to about 100 mg, or about 0.1 mg to about 20 mg.

Rho-associated Coiled-coil Kinase (ROCK) Inhibitors

As illustrated herein use of one or more Rho-associated coiled coil forming protein serine/threonine kinase inhibitors can facilitate conversion of differentiated cells into the cardiac cell lineage.

Rho-associated coiled-coil kinase (ROCK) is an effector molecule of the Rho GTPase signaling pathway and controls physiological processes such as vascular constriction and nerve axon extension (Riento et al. Nat Rev Mol Cell Biol 4:446-456, 2003). A variety of Rho-associated coiled coil forming protein serine/threonine kinase inhibitors can be employed in the compositions and methods described herein including the following:

Y27632 (also known as -27632, Y27632, 146986-50-7, Y-27632 dihydrochloride, Y27, Y-27632, Y27632, Ximelegatran; 4-[(1R)-1-aminoethyl]-N-pyridin-4-ylcyclohexane-1-carboxamide), a selective ROCK1 (p160ROCK) inhibitor with, for example, an IC50 of 140 nM;

4-(2-pyridylcarbamoyl)piperidine
1-benzyloxycarbonyl-4-(4-pyridylcarbamoyl)piperidine
1-benzoyl-4-(4-pyridylcarbamoyl)piperidine
1-propyl-4-(4-pyridylcarbamoyl)piperidine
1-[3-(2-(2-thienylmethyl)phenoxy)-2-hydroxypropyl]-4-(4-pyridylcarbamoyl)piperidine
4-(4-pyridyl carbamoyl)piperidine
1-benzyl-4-(4-pyridylcarbamoyl)-1,2,5,6-tetrahydropyridine
3-(4-pyridylcarbamoyl)piperidine
1-benzyl-3-(4-pyridylcarbamoyl)piperidine
1-(2-(4-benzyloxyphenoxy)ethyl)-4-(N-(2-pyridyl)-N-benzylcarbamoyl) piperidine
1-formyl-4-(4-pyridylcarbamoyl)piperidine
4-(3-pyridylcarbamoyl)piperidine
1-isopropyl-4-(4-pyridylcarbamoyl)piperidine
1-methyl-4-(4-pyridylcarbamoyl)piperidine
1-hexyl-4-(4-pyridylcarbamoyl)piperidine
1-benzyl-4-(4-pyridylcarbamoyl)piperidine
1-(2-phenylethyl)-4-(4-pyridylcarbamoyl)piperidine
1-(2-(4-methoxyphenyl)ethyl)-4-(4-pyridylcarbamoyl)-piperidine
1-(2-(4-methoxyphenyl)ethyl)-4-(2-pyridyl carbamoyl)-piperidine
1-(2-(4-chlorophenyl)ethyl)-4-(4-pyridylcarbamoyl)-piperidine
1-diphenylmethyl-4-(2-pyridylcarbamoyl)piperidine
1-[2-(4-(5-methyl-3-oxo-2,3,4,5-tetrahydropyridazin-6-yl) phenyl)ethyl]-4-(2-pyridylcarbamoyl)piperidine
1-(4-(4,5-dihydro-2-furyl)phenyl)-4-(4-pyridylcarbamoyl) piperadine
1-(2-nitrophenyl)-4-(4-pyridylcarbamoyl)piperidine
1-(2-aminophenyl)-4-(4-pyridylcarbamoyl)piperidine
1-nicotinoyl-4-(4-pyridylcarbamoyl)piperidine
1-isonicotinoyl-4-(4-pyridylcarbamoyl)piperidine
1-(3,4,5-trimethoxybenzoyl)-4-(4-pyridylcarbamoyl)-piperidine
1-acetyl-4-(4-pyridylcarbamoyl)piperidine
1-(3-(4-fluorobenzoyl)propyl)-4-(4-pyridylcarbamoyl)-piperidine
1-(3-(4-fluorobenzoyl)propyl)-4-(2-pyridylcarbamoyl)-piperidine
1-(1-(4-hydroxybenzoyl)ethyl)-4-(2-pyridylcarbamoyl)-piperidine
1-(1-(4-benzyloxybenzoyl)ethyl)-4-(2-pyridylcarbamoyl)-piperidine 1-(2-(4-hydroxyphenoxy)ethyl)-4-(2-pyridylcarbamoyl)-piperidine
1-(4-(4-fluorophenyl)-4-hydroxybutyl)-4-(4-pyridylcarbamoyl)piperidine
1-(1-methyl-2-(4-hydroxyphenyl)-2-hydroxyethyl)-4-(2-pyridylcarbamoyl)piperidine
1-cinnamyl-4-(2-pyridylcarbamoyl)piperidine
1-(2-hydroxy-3-phenoxypropyl)-4-(4-pyridylcarbamoyl)piperidine
1-(2-hydroxy-3-phenoxypropyl)-4-(3-pyridylcarbamoyl)piperidine
1-(2-hydroxy-3-phenoxypropyl)-4-(2-pyridylcarbamoyl)piperidine
1-(2-phenylethyl)-4-[N-(2-pyridyl)-N-(2-(N,N-dimethylamino)ethyl)carbamoyl]piperidine
1-benzyloxycarbonyl-4-(2-pyridylcarbamoyl)piperidine
1-(3-chlorophenyl)carbamoyl-4-(4-pyridylcarbamoyl)-piperidine
4-[N-(2-pyridyl)-N-(2-(N,N-dimethylamino)ethyl)-carbamoyl]piperidine
1-methyl-4-(4-pyridylcarbamoyl)-1,2,5,6-tetrahydropyridine
1-nicotinoyl-3-(4-pyridylcarbamoyl)piperidine
1-[2-(4-fluorobenzoyl)ethyl]-4-(4-pyridylcarbamoyl)-piperidine
1-(6-chloro-2-methylimidazo[1,2-a]pyridine-3-carbonyl)-4-(4-pyridylcarbamoyl)piperidine
1-(4-nitrobenzyl)-4-(4-pyridylcarbamoyl)piperidine
1-hexyl-4-(4-pyridylcarbamoyl)piperidine
1-benzyloxycarbonyl-4-(2-chloro-4-pyridylcarbamoyl)-piperidine
4-(2-chloro-4-pyridylcarbamoyl)piperidine
1-(2-chloronicotinoyl)-4-(4-pyridylcarbamoyl)piperidine
3-(2-chloro-4-pyridylcarbamoyl)piperidine
1-(4-phthalimidobutyl)-4-(4-pyridylcarbamoyl)piperidine
1-(3,5-di-tert-butyl-4-hydroxycinnamoyl)-4-(4-pyridyl carbamoyl)piperidine
1-carbamoylmethyl-4-(4-pyridylcarbamoyl)piperidine
1-benzyloxycarbonyl-4-(5-nitro-2-pyridylcarbamoyl)-piperidine
4-(5-nitro-2-pyridylcarbamoyl)piperidine
trans-4-benzyloxycarboxamidomethyl-1-(4-pyridylcarbamoyl)cyclohexane
trans-4-aminomethyl-1-(4-pyridylcarbamoyl)cyclohexane
trans-4-formamidomethyl-1-(4-pyridylcarbamoyty-cyclohexane
trans-4-dimethylaminomethyl-1-(4-pyridylcarbamoyl)-cyclohexane
N-benzylidene-trans-(4-pyridylcarbamoyl)-cyclohexylmethylamine
trans-4-benzylaminomethyl-1-(4-pyridylcarbamoyl)-cyclohexane
trans-4-isopropylaminomethyl-1-(4-pyridylcarbamoyl)-cyclohexane
trans-4-nicotinoylaminomethyl-1-(4-pyridylcarbamoyl)-cyclohexane
trans-4-cyclohexylaminomethyl-1-(4-pyridylcarbamoyl)-cyclohexane
trans-4-benzyloxycarboxamide-1-(4-pyridylcarbamoyl)-cyclohexane
trans-4-amino-1-(4-pyridylcarbamoyl)cyclohexane
trans-4-(1-aminoethyl)-1-(4-pyridylcarbamoyl)cyclohexane
trans-4-aminomethyl-cis-2-methyl-1-(4-pyridylcarbamoyl)cyclohexane
(+)-trans-4-(1-benzyloxycarboxamidopropyl)-1-cyclohexanecarboxylic acid
(+)-trans-4-(1-benzyloxycarboxamidopropyl)-1-(4-pyridylcarbamoyl)cyclohexane
(−)-trans-4-(1-benzyloxycarboxamidopropyl)-1-(4-pyridylcarbamoyl)cyclohexane
(+)-trans-4-(1-aminopropyl)-1-(4-pyridylcarbamoyl)-cyclohexane
(−)-trans-4-(1-aminopropyl)-1-(4-pyridylcarbamoyl)-cyclohexane
(−)-trans-4-(1-benzyloxycarboxamidoethyl)-1-(4-pyridylcarbamoyl)cyclohexane
(+)-trans-4-(1-benzyloxycarboxamidoethyl)-1-(4-pyridylcarbamoyl)cyclohexane
(+)-trans-4-(1-aminoethyl)-1-(4-pyridylcarbamoyl)-cyclohexane
(−)-trans-4-(1-aminoethyl)-1-(4-pyridylcarbamoyl)-cyclohexane
trans-4-(4-chlorobenzoyl)aminomethyl-1-(4-pyridylcarbamoyl)cyclohexane
trans-4-aminomethyl-1-(2-pyridylcarbamoyl)cyclohexane
trans-4-benzyloxycarboxamidomethyl-1-(2-pyridylcarbamoyl)cyclohexane
trans-4-methylaminomethyl-1-(4-pyridylcarbamoyl)-cyclohexane
trans-4-(N-benzyl-N-methylamino)methyl-1-(4-pyridylcarbamoyl)cyclohexane
trans-4-aminomethyl-1-(3-pyridylcarbamoyl)cyclohexane
trans-4-aminomethyl-1-[(3-hydroxy-2-pyridyl)carbamoyl]-cyclohexane
trans-4-benzyloxycarboxamidomethyl-1-(3-pyridylcarbamoytcyclohexane
trans-4-benzyloxycarboxamidomethyl-1-[(3-benzyloxy-2-pyridyl)carbamoyl]cyclohexane
trans-4-phthalimidomethyl-1-(4-pyridylcarbamoyl)-cyclohexane
trans-4-benzyloxycarboxamidomethyl-1-(3-methyl-4-pyridylcarbamoyl)cyclohexane
trans-4-aminomethyl-1-(3-methyl-4-pyridylcarbamoyl)-cyclohexane
4-(trans-4-benzyloxycarboxamidomethylcyclohexyl-carbonyl)amino-2, 6-dimethylpyridine-N-oxide
4-(trans-4-aminomethylcyclohexylcarbonyl)amino-2,6-dimethylpyridine-N-oxide
trans-4-aminomethyl-1-(2-methyl-4-pyridylcarbamoyl)-cyclohexane
trans-4-(1-benzyloxycarboxamidoethyl)-1-(4-pyridylcarbamoyl)cyclohexane
trans-4-(1-amino-1-methylethyl)-1-(4-pyridylcarbamoyl)-cyclohexane
trans-4-(2-aminoethyl)-1-(4-pyridylcarbamoyl)cyclohexane
trans-4-(2-amino-1-methylethyl)-1-(4-pyridylcarbamoyl)-cyclohexane
trans-4-(1-aminopropyl)-1-(4-pyridylcarbamoyl)-cyclohexane
trans-4-aminomethyl-trans-1-methyl-1-(4-pyridylcarbamoyl)cyclohexane
trans-4-benzylaminomethyl-cis-2-methyl-1-(4-pyridylcarbamoyl)cyclohexane
trans-4-(1-benzyloxycarboxamide-1-methylethyl)-1-(4-pyridylcarbamoyl)cyclohexane
trans-4-benzyloxycarboxamidomethyl-1-(N-methyl-4-pyridylcarbamoyl)cyclohexane
trans-4-(1-acetamide-1-methylethyl)-1-(4-pyridylcarbamoyl)cyclohexane
trans-N-(6-amino-4-pyrimidyl)-4-aminomethylcyclohexanecarboxamide
trans-N-(1H-pyrrolo[2,3-b]pyridin-4-yl)-4-aminomethylcyclohexane-carboxamide (+)-trans-N-(1H-pyrrolo[2,3-b]pyridin-4-yl)-4-(1-amino-ethylcyclo-hexanecarboxamide
trans-N-(1H-pyrrolo[2,3-b]pyridin-4-yl)-4-(1-amino-1-methylethyl)cyclo-hexanecarboxamide
trans-N-(1H-pyrazolo[3,4-b]pyridin-4-yl)-4-aminomethyl-cyclohexane-carboxamide
(+)-trans-N-(1H-pyrazolo[3,4-b]pyridin-4-yl)-4-(1-aminoethyl)cyclo-hexanecarboxamide
trans-N-(1H-pyrazolo[3,4-b]pyridin-4-yl)-4-(1-amino-1-methylethyl)cyclo-hexanecarboxamide
(+)-trans-N-(2-amino-4-pyridyl)-4-(1-aminoethyl)-cyclohexanecarboxamide
trans-N-(1H-pyrazolo[3,4-d]pyrimidin-4-yl)-4-aminomethylcyclohexane-carboxamide
(+)-trans-N-(1H-pyrazolo[3,4-d]pyrimidin-4-yl)-4-(1-aminoethyl)cyclohexane carboxamide
trans-N-(1H-pyrazolo[3,4-d]pyrimidin-4-yl)-4-(1-amino-1-methylethyl)cyclohexane carboxamide
trans-N-(4-pyrimidinyl)-4-aminomethylcyclohexanecarboxamide
trans-N-(3-amino-4-pyridyl)-4-aminomethylcyclohexanecarboxamide
trans-N-(7H-imidazo[4,5-d]pyrimidin-6-yl)-4-aminomethylcyclo-hexanecarboxamide
trans-N-(3H-1,2,3-triazolo[4,5-d]pyrimidin-7-yl)-4-aminomethyl-cyclohexane carboxamide
trans-N-(1-benzyl-1H-pyrazolo[3,4-b]pyridin-4-yl)-4-aminomethylcyclohexane carboxamide trans-N-(1H-5-pyrazolyl)-4-aminomethylcyclo-hexanecarboxamide
trans-N-(1H-pyrazolo[3,4-b]pyridin-4-yl)-4-aminomethyl-cyclo-hexanecarboxamide
trans-N-(4-pyridazinyl)-4-aminomethylcyclohexanecarboxamide
trans-N-(7H-pyrrolo[2,3-d]pyrimidin-4-yl)-4-aminomethyl-cyclo-hexanecarboxamide
trans-N-(2-amino-4-pyridyl)-4-aminomethylcyclohexanecarboxamide
trans-N-(thieno[2,3-d]pyrimidin-4-yl)-4-aminomethylcyclohexanecarboxamide
trans-N-(5-methyl-1,2,4-triazolo[1,5-a]pyrimidin-7-yl)-4-aminomethyl-cyclohexanecarboxamide
trans-N-(3-cyano-5-methylpyrazolo[1,5-a]pyrimidin-7-yl)-4-aminomethyl-cyclohexanecarboxamide
trans-N-(1H-pyrazolo[3,4-b]pyridin-4-yl)-4-(1-amino-1-methylethyl)cyclohexanecarboxamide
trans-N-(2-(1-pyrrolidinyl)-4-pyridyl)-4-aminomethylcyclohexane-carboxamide
trans-N-(2,6-diamino-4-pyrimidyl)-4-aminomethylcyclohexanecarboxamide
(+)-trans-N-(7-methyl-1,8-naphthyridin-4-yl)-4-(1-aminoethyl)cyclohexane-carboxamide
trans-N-(1-benzyloxymethylpyrrolo[2,3-b]pyridin-4-yl)-4-aminomethyl-cyclohexanecarboxamide
(+)-trans-N-(1-methylpyrrolo[2,3-b]pyridin-4-yl)-4-(1-aminoethyl)cyclo-hexanecarboxamide
trans-N-benzyl-N-(2-benzylamino-4-pyridyl)-4-(1-amino-1-methyl ethyl)-cyclohexanecarboxamide
trans-N-(2-azide-4-pyridyl)-4-aminomethylcyclohexanecarboxamide
trans-N-(2,3-dihydro-1H-pyrrolo[2,3-b]pyridin-4-yl)-4-aminomethyl-cyclohexanecarboxamide
trans-N-(2,3-dihydro-1H-pyrrolo[2,3-b]pyridin-4-yl)-4-(1-amino-1-methylethyl)cyclohexanecarboxamide
trans-N-(2-carboxy-4-pyridyl)-4-aminomethylcyclohexanecarboxamide
(R)-(+)-trans-N-(3-bromo-1H-pyrrolo[2,3-b]pyridin-4-yl)-4-aminoethyl)cyclohexanecarboxamide
trans-N-(1H-pyrrolo[2,3-b]pyridin-4-yl)-4-guanidinomethylcyclohexanecarboxamide
trans-N-(1H-pyrazolo[3,4-b]pyridin-4-yl)-4-guanidinomethyl-cyclohexanecarboxamide
trans-N-(4-pyridyl)-4-guanidinomethylcyclohexanecarboxamide
trans-N-(1-methylpyrrolo[2,3-b]pyridin-4-yl)-4-(guanidinomethyl)cyclo-hexanecarboxamide
trans-N-(1H-pyrrolo[2,3-b]pyridin-4-yl) 4-(2-imidazolin-2-yl)aminomethyl-cyclohexanecarboxamide
trans-N-(1-benzyloxymethylpyrrolo[2,3-b]pyridin-4-yl)-4-guanidinomethyl-cyclohexanecarboxamide
trans-N-(2-amino-4-pyridyl)-4-guanidinomethylcyclohexanecarboxamide
trans-N-(1-benzyloxymethyl-1H-pyrrolo[2,3-b]pyridin-4-yl)-4-(2-imidazolin-2-yl)aminomethylcyclohexanecarboxamide
trans-N-(1H-pyrrolo[2,3-b]pyridin-4-yl)-4-(3-benzylguanidinomethyl)cyclo-hexanecarboxamide
trans-N-(1H-pyrrolo[2,3-b]pyridin-4-yl)-4-(3-phenylguanidinomethyl)-cyclohexanecarboxamide
trans-N-(1H-pyrrolo[2,3-b]pyridin-4-yl)-4-(3-propylguanidinomethyl)-cyclohexanecarboxamide
trans-N-(1H-pyrrolo[2,3-b]pyridin-4-yl)-4-(3-octylguanidinomethyl)-cyclohexanecarboxamide
trans-N-(1-benzyloxymethylpyrrolo[2,3-b]pyridin-4-yl)-4-(2-benzyl-3-ethylguanidinomethyl)cyclohexanecarboxamide
trans-N-(1H-pyrrolo[2,3-b]pyridin-4-yl)-4-(imidazol-2-yl)aminomethyl-cyclohexanecarboxamide
trans-N-(1H-pyrrolo[2,3-b]pyridin-4-yl)-4-(thiazol-2-yl)aminomethyl-cyclohexane carboxamide
(R)-(+)-N-(4-pyridyl)-4-(1-aminoethyl)benzamide
N-(4-pyridyl)-4-(1-amino-1-methylethyl)benzamide
N-(4-pyridyl)-4-aminomethyl-2-benzyloxybenzamide
N-(4-pyridyl)-4-aminomethyl-2-ethoxybenzamide
(R)-(−)-N-(4-pyridyl)-4-(1-aminoethyl)-3-nitrobenzamide
(R)-(−)-N-(4-pyridyl)-3-amino-4-(1-aminoethyl)benzamide
(R)-(+)-N-(4-pyridyl)-4-(1-aminoethyl)-3-chlorobenzamide
N-(4-pyridyl)-3-aminomethylbenzamide
(R)-(+)-N-(1H-pyrrolo[2,3-b]pyridin-4-yl)-4-aminoethyl)benzamide
(R)-(+)-N-(1H-pyrazolo[3,4-b]pyridin-4-yl)-4-(1-aminoethyl)benzamide
N-(1H-pyrazolo[3,4-b]pyridin-4-yl)-4-guanidinomethyl-benzamide
N-(4-pyridyl)-4-guanidinomethylbenzamide
(R)-(+)-N-(4-pyridyl)-4-(1-aminoethyl)-3-fluorobenzamide
N-(4-pyridyl)-4-aminomethylbenzamide
N-(4-pyridyl)-4-aminomethyl-2-hydroxy benzamide
N-(4-pyridyl)-4-(2-aminoethyl)benzamide
N-(4-pyridyl)-4-aminomethyl-3-nitrobenzamide
N-(4-pyridyl)-3amino-4-aminomethylbenzamide
(S)-(−)-N-(4-pyridyl)-4-(1-aminoethyl)benzamide
(S)-(−)-N-(4-pyridyl)-2-(1-aminoethyl)benzamide
(R)-(+)-N-(4-pyridyl)-4-(1-aminoethyl)-2-chlorobenzamide
(R)-(+)-N-(1H-pyrrolo[2,3-b]pyridin-4-yl)-4-(1-(3-propylguanidino)ethyl)-benzamide
(R)-(−)-N-(1H-pyrrolo[2,3-b]pyridin-4-yl)-4-(1-aminoethyl)-3-azide-benzamide
(R)-(+)-N-(4-pyridyl)-4-(1-aminoethyl)-2-nitrobenzamide
(R)-(−)-N-(4-pyridyl)-4-(1-aminoethyl)-3-ethoxybenzamide
(R)-(+)-N-(3-iodo-1H-pyrrolo[2,3-b]pyridin-4-yl)-4-(1-aminoethyl)benzamide (R)-(+)-N-(3-iodo-1H-pyrrolo[2,3-b]pyridin-4-yl)-4-(1-aminoethyl)-3-azidebenzamide (R)-(−)-N-(4-pyridyl)-4-(1-aminoethyl)-3-hydroxybenzamide N-(1H-pyrazolo[3,4-b]pyridin-4-yl)-4-guanidinomethyl-3-nitrobenzamide (R)-N-(1H-pyrazolo[3,4-b]pyridin-4-yl)-4-(1-guanidinoethyl)-3-nitro-benzamide (R)-N-(1H-pyrazolo[3,4-b]pyridin-4-yl)-4-(1-aminoethyl)-2-nitrobenzamide N-(1H-pyrazolo[3,4-b]pyridin-4-yl)-4-guanidinobenzamide (R)-N-(1H-pyrazolo[3,4-b]pyridin-4-yl)-4-(1-aminoethyl)-3-nitrobenzamide (R)-N-(1H-pyrazolo[3,4-b]pyridin-4-yl)-4-(1-guanidinoethyl)benzamide N-(1H-pyrazolo[3,4-b]pyridin-4-yl)-4-(1-amino-2-hydroxyethyl)benzamide N-(1H-pyrazolo[3,4-b]pyridin-4-yl)-4-aminomethyl-3-nitrobenzamide N-(1H-pyrrolo[2,3-b]pyridin-4-yl)-4-piperidinecarboxamide N-(1H-pyrazolo[3,4-b]pyridin-4-yl)-4-piperidinecarboxamide N-(1H-pyrazolo[3,4-b]pyridin-4-yl)-1-aminoacetyl-4-piperidine-carboxamide N-(1-methoxymethyl-1H-pyrazolo[3,4-b]pyridin-4-yl)-4-piperidine-carboxamide N-(2,3-dihydro-1H-pyrrolo[2,3-b]pyridin-4-yl)-4-piperidinecarboxamide N-(1H-pyrrolo[2,3-b]pyridin-4-yl)-1-(2-phenylethyl)-4-piperidine-carboxamide N-(1H-pyrrolo[2,3-b]pyridin-4-yl)-1-amidino-4-piperidinecarboxamide N-(1H-pyrrolo[2,3-b]pyridin-4-yl)-1-(3-phenylpropyl)-4-piperidine-carboxamide N-(1H-pyrrolo[2,3-b]pyridin-4-yl)-1-benzyl-4-piperidinecarboxamide N-(1H-pyrazolo[3,4-b]pyridin-4-yl)-1-(2-phenylethyl)-4-piperidine-carboxamide N-(1H-pyrazolo[3,4-b]pyridin-4-yl)-1-(3-phenylpropyl)-4-piperidine-carboxamide;

N-(1H-pyrrolo[2,3-b]pyridin-4-yl)-4-(1-amino-1-methylethyl)benzamide; or any combination thereof.

Inhibitors of Rho-associated coiled coil forming protein serine/threonine kinases are also described by International Patent Application No. PCT/AU2009/001417; International Patent Application No. PCT/GB2007/003636; Ishizaki et al, *Mol Pharmacol* 57:976-983 (2000); Narumiya et al, *Methods Enzymol* 525:273-284 (2000), each of which is specifically incorporated by reference herein in its entirety. Any of the ROCK inhibitors described in these documents can be employed in the compositions and methods described herein.

In some embodiments, the Rho-associated coiled coil forming protein serine/threonine kinase inhibitor can be Y27632.

The ROCK inhibitor can be in the form of a hydrate or salt of any of the foregoing compounds.

The ROCK inhibitor(s) can be employed in the compositions and methods described herein in a variety of amounts and/or concentrations. For example, the ROCK inhibitor(s) can be employed in a solution at a concentration of about 0.001 micromolar to about 50 millimolar, or about 0.01 micromolar to about 10 millimolar, or about 0.1 micromolar to about 0.1 millimolar, or about 0.1 micromolar to about 100 micromolar, or about 1 micromolar to about 50 micromolar. In a dry formulation, the ROCK inhibitor(s) can be present in amounts of about 0.1 mg to about 4 g, or about 0.5 mg to about 3 g, or about 1.0 mg to about 2 g, or about 1.5 mg to about 1 g.

Histone Methyl-transferase Inhibitors

As illustrated herein use of one or more histone methyltransferase inhibitors can facilitate conversion of differentiated cells into the cardiac cell lineage. For example, the histone methyltransferase inhibitor can be a G9a histone methyltransferase inhibitor.

The G9a histone methyltransferase enzymatically methylates histone lysines. The G9a histone methyltransferase is also named euchromatin histone methyltransferase 2 (EHMT2). Histone lysine methylation has important roles in the organization of chromatin domains and the regulation of gene expression.

A variety of G9a histone methyl-transferase inhibitors can be employed. For example, the G9a histone methyl-transferase inhibitor can be any of the following.

Bix-01294 (also known as BIX01294, 935693-62-2; N-(1-benzylpiperidin-4-yl)-6,7-dimethoxy-2-(4-methyl-1,4-diazepan-1-yl)quinazolin-4-amine);

Chaetocin (also known as Chetocin, Chaetocin from *Chaetomium minutum*, 28097-03-2, BRN 5722505, AC1L4PPK, C9492_SIGMA, 'bR,11aS,11'aS)-, MolPort-003-983-881; [10b,10'b(11H,11'H)-Bi-3,11a-epidithio-11aH-pyrazino[1',2':1,5]pyrrolo[2,3-b]indole]-1,1',4,4'-tetrone, 2,2',3,3',5a,5'a,6,6'-octahydro-3,3'-bis(hydroxymethyl)-2,2'-dimethyl-, (3S,3'S,5aR,5'aR,10bR, 10);

3-deazaneplanocin hydrochloride (also known as 2,3-DMMC, or 5R-(4-amino-1H-imidazo[4,5-c]pyridin-1-yl)-3-(hydroxymethyl)-3-cyclopentene-1S,2R-diol, monohydrochloride);

UNC 0224 (also known as CHEMBL576781, CHEBI: 671385, NCGC00185956-01, 1197196-48-7; 7-[3-(dimethylamino)propoxy]-6-methoxy-2-(4-methyl-1,4-diazepan-1-yl)-N-(1-methylpiperidin-4-yl)quinazolin-4-amine);

UNC 0638 (2-cyclohexyl-6-methoxy-4-[(1-propan-2-ylpiperidin-4-yl)methyl]-7-(3-pyrrolidin-1-ylpropoxy)quinazoline)

UNC 0646 (N-(1-cyclohexylpiperidin-4-yl)-2-(4-isopropyl-1,4-diazepan-1-yl)-6-methoxy-7-(3-(piperidin-1-yl)propoxy)quinazolin-4-amine);

BRD4770 (2-(Benzoylamino)-1-(3-phenylpropyl)-1H-benzimidazole-5-carboxylic acid methyl ester) see, also, Yuan et al., *ACS Chem. Biol.* 7(7): 1152-1157 (2012) (incorporated herein by reference in its entirety); and combinations thereof.

G9a histone methyl-transferase inhibitors can be obtained commercially, for example, from Tocris Bioscience (see website at tocris.com/pharmacologicalBrowser. php?ItemId=236264&Type=Inhibitors#.UdYcHeDD85s).

In some embodiments, the G9a histone methyltransferase inhibitor can be Bix-01294, whose structure is shown below.

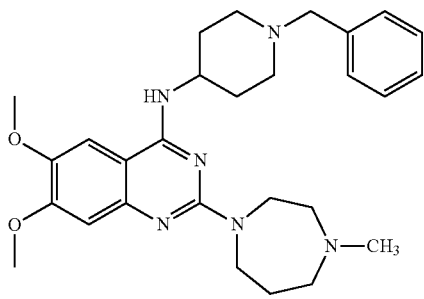 [SMILES: COc1cc2nc(N3CCCN(C)CC3)nc(NC3CCN(Cc4ccccc4)CC3)c2cc1OC]

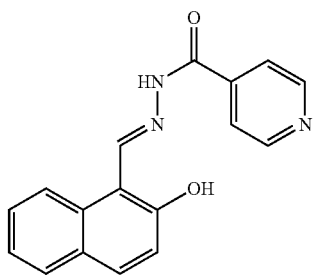

AS8351

The structure of PBIT is as follows:

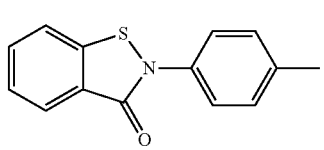

PBIT

The G9a histone methyl-transferase inhibitors can be in the form of a hydrate or salt of any of the foregoing compounds. For example, the Bix-01294 can be in the form of a hydrate or salt, for example, a hydrochloride salt of the hydrate.

G9a histone methyltransferase inhibitors can be used at a variety of concentrations. For example, when used in solution the G9a histone methyltransferase inhibitors can be used at about 0.001 micromolar to about 50 millimolar, or about 0.01 micromolar to about 10 millimolar, or about 0.01 μM to about 10 μM, or about 0.05 μM to about 9 μM, or about 0.1 μM to about 8 μM, or about 0.2 μM to about 7 μM, or about 0.3 μM to about 6 μM, or about 0.3 μM to about 4 μM, or about 0.5 μM to about 2 μM. In a dry formulation, the histone methyltransferase inhibitors can be present in amounts of about 0.1 mg to about 4 g, or about 0.5 mg to about 3 g, or about 1.0 mg to about 2 g, or about 1.5 mg to about 1 g.

Iron Chelator and/or KDM5B Inhibitor

As illustrated herein use of one or more iron chelators and/or KDM5B inhibitors can facilitate conversion of differentiated cells into the cardiac cell lineage.

A variety of iron chelators and/or KDM5B inhibitors can be employed. For example, the iron chelators and/or KDM5B inhibitors can be any of the following.

AS8351 (also known as 2-hydroxy-1-naphthaldehyde-isonicotinoylhydrazone);
PBIT (also known as 2-(4-methylphenyl)-1,2-benzisothiazol-3(2H)-one; 2-(4-methylphenyl)-2,3-dihydrobenzisothiazol-3-one, 2-p-tolyl-1,2-benzisothiazolin-3-one);
Omecamtiv mecarbil (also known as CK-1827452, 873697-71-3, CHEMBL1800955, Omecamtiv mecarbil, CK-1827452, CK-1827452, CK1827452, S2623_Selleck, SureCN400544, UNII-2M 19539ERK; 4-[[2-fluoro-3-[(6-methylpyridin-3-yl)carbamoylamino]phenyl]methyl]piperazine-1-carboxylate), which has the following structure

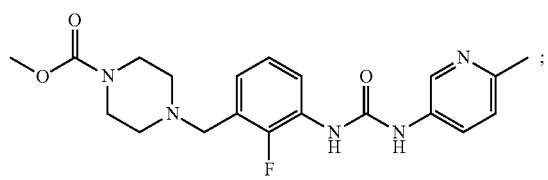

and
any combination thereof.

In some embodiments, the iron chelator and/or KDM5B inhibitor is AS8351 or PBIT. AS8351 has the following structure.

The iron chelator and/or KDM5B inhibitor can be in the form of a hydrate or salt of any of the foregoing compounds.

The iron chelator and/or KDM5B inhibitors can be used at a variety of concentrations. For example, when used in solution the iron chelator and/or KDM5B inhibitors can be used at about 0.001 micromolar to about 50 millimolar, or about 0.01 micromolar to about 10 millimolar, or about 0.01 μM to about 10 μM, or about 0.05 μM to about 9 μM, or about 0.1 μM to about 8 μM, or about 0.2 μM to about 7 μM, or about 0.3 μM to about 6 μM, or about 0.3 μM to about 4 μM, or about 0.5 μM to about 2 μM. In cases where the PBIT is used, the PBIT can be present at about 0.001 micromolar to about 50 millimolar, or about 0.01 micromolar to about 10 millimolar, or about 0.1 μM to about 100 μM, or about 0.5 μM to about 50 μM, or about 1 μM to about 40 μM, or about 2 μM to about 30 μM, or about 3 μM to about 25 μM, or about 4 μM to about 20 μM, or about 5 μM to about 15 μM, or about 10μ. In a dry formulation, the iron chelator and/or KDM5B inhibitor can be present in amounts of about 0.1 mg to about 5 g, or about 0.5 mg to about 4 g, or about 1.0 mg to about 3 g, or about 1.5 mg to about 2 g.

Platelet-Derived Growth Factor (PDGF) Receptor Inhibitors

As illustrated herein use of one or more PDGF receptor inhibitors can facilitate conversion of differentiated cells into the cardiac cell lineage.

A variety of PDGF receptor inhibitors can be employed. For example, the PDGF receptor inhibitors can be any of the following.

SU16f (5-[1,2-Dihydro-2-oxo-6-phenyl-3H-in-dol-3-ylidene)methyl]-2,4-dimethyl-1H-pyrrole-3-pr-opanoic acid), which is a potent and selective platelet-derived growth factor receptor β (PDGFRβ) inhibitor (IC50=10 nM);
AG18 (also known as RG-50810, Tyrphostin A23; [(3,4-Dihydroxyphenyl)methylene]-propenedinitrile), which is an inhibitor of epidermal growth factor receptor (EGFR) and platelet-derived growth factor receptor (PDGFR) kinase (IC50 values are 35 and 25 μM respectively);
DMPQ (5,7-Dimethoxy-3-(4-pyridinyl)quinol-ine dihydrochloride), which is a potent and selective inhibitor of human vascular β-type platelet derived growth factor receptor tyrosine kinase (PDGFRβ) (IC50=80 nM);

PD 166285 (6-(2,6-Dichlorophenyl)-2-[[4-[2-(diethylamino)ethoxy]-phenyl]amino]-8-methylpyrido[2,3-d]pyrimidin-7(8H)-one dihydrochloride), which is a potent inhibitor of the tyrosine kinases c-Src, fibroblast growth factor receptor 1 (FGFR1), and platelet-derived growth factor receptor β (PDGFRβ) (IC50 values are 8.4, 39.3 and 98.3 nM respectively);

SU 6668 (5-[1,2-Dihydro-2-oxo-3H-indol-3-yli-dene)methyl]-2,4-dimethyl-1H-pyrrole-3-propanoic acid), which is an ATP-competitive PDGFR. VEGF and FGFR inhibitor (IC50 values are 0.06, 2.43, 3.04 and >100 μM for PDGFRβ, VEGFR2, FGFR1 and EGFR respectively);

Sunitinib maleate (also known as SU 11248; N-[2-(Diethylamino)ethyl]-5-[(Z)-(5-fluoro-1,2-dihydro-2-oxo-3H-indol-3-ylidine)methy-1]-2,4-dimethyl-1H-pyrrole-3-carboxamide(2S)-2-hydroxybutanedioate salt), which is a potent, ATP-competitive VEGFR, PDGFRβ and KIT inhibitor (Ki values are 2, 9, 17, 8 and 4 nM for VEGFR-1, -2, -3, PDGFRβ and KIT respectively); or combinations thereof.

In some embodiments, the PDGF receptor inhibitor is SU16f, which has the following structure.

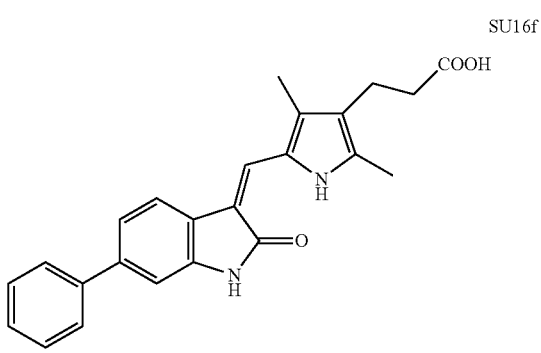 [SMILES: Cc1[nH]c(/C=C2\C(=O)Nc3cc(-c4ccccc4)ccc32)c(C)c1CCC(=O)O]

SU16f

The PDGF receptor inhibitor can be in the form of a hydrate or salt of any of the foregoing compounds.

The PDGF receptor inhibitors can be used at a variety of concentrations. For example, when used in a solution, the PDGF receptor inhibitors can be used at about 0.001 micromolar to about 50 millimolar, or about 0.01 micromolar to about 10 millimolar, or about 0.01 μM to about 10 μM, or about 0.05 μM to about 9 μM, or about 0.1 μM to about 8 μM, or about 0.2 μM to about 7 μM, or about 0.3 μM to about 6 μM, or about 0.3 μM to about 4 μM, or about 0.5 μM to about 2 μM. In a dry formulation, the PDGF inhibitors can be present in amounts of about 0.1 mg to about 4 g, or about 0.5 mg to about 3 g, or about 1.0 mg to about 2 g, or about 1.5 mg to about 1 g.

Platelet-Derived Growth Factor Tyrosine Kinase Inhibitors

As illustrated herein use of one or more PDGF receptor tyrosine kinase inhibitors can facilitate conversion of differentiated cells into the cardiac cell lineage.

A variety of PDGF receptor tyrosine kinase inhibitors can be employed. For example, the PDGF receptor tyrosine kinase inhibitors can be any of the following.

JNJ-10198409 (also known as 3-Fluoro-N-(6,7-dimethoxy-2,4-dihydroindeno[1,2-c]pyrazol-3-yl)phenylamine, N-(3-fluorophenyl)-2,4-dihydro-6,7-dimethoxy-Indeno [1,2-c]pyrazol-3-amine, RWJ 540973), which is a potent ATP-competitive inhibitor of Platelet-Derived Growth Factor receptor tyrosine kinase (PDGF-RTK) with both antiangiogenic and a direct tumor cell antiproliferative activity (IC$_{50}$ values of 4.2 nM for PDGF-β and 45 nM for PDGF-α kinase);

AG-370 (also known as Tyrphostin AG 370, Tyrphostin B7, 2-Amino-4-(1H-indol-5-yl)-1,1,3-tricyanobuta-1,3-diene), which is a member of the tyrphostin family of tyrosine kinase inhibitors; it is a selective inhibitor of the PDGF receptor kinase (IC$_{50}$=20 μM) vs. the EGF receptor kinase (IC$_{50}$=820 μM);

AG-1296 (also known as Tyrphostin AG 1296, 6,7-Dimethoxy-3-phenylquinoxaline), which is a potent inhibitor of PDGF receptor tyrosine kinase (IC$_{50}$=1 μM);

Imatinib mesylate (also known as STI-571, CGP-57148B);

3-(4-Isopropylbenzylidenyl)indolin-2-one, a non-selective inhibitor of receptor tyrosine kinases that can inhibit PDGFR as well as other receptors;

PKC-412 (also known as 4'-N-Benzoyl-staurosporine, Midostaurin, CGP 41251), an inhibitor of a variety of serine/threonine and tyrosine kinases including PDGFR;

RG-13022 (3,4-Dimethoxy-α-(3-pyridyl)-(Z)-cinnamonitrile), a long-acting inhibitor of PDGF receptor tyrosine kinases;

SU 11652 (5-[5-Fluoro-2-oxo-1,2-dihydroindol-(3Z)-ylidenemethyl]-2,4-dimethyl-1H-pyrrole-3-carboxylic acid (2-diethylaminoethyl)amide), which is a potent, ATP-competitive and cell permeable inhibitor of tyrosine kinases (VEGF-R2 IC$_{50}$=27 nM, PDGF-R3 IC$_{50}$=3 nM);

Tyrphostin 9 (also known as RG-50872, Malonaben, SF 6847), which is a selective inhibitor of the PDGF receptor tyrosine kinase (IC$_{50}$=1.2 μM);

Tyrphostin 46, which inhibits PDGF receptor kinase (IC$_{50}$=50 μM);

Tyrphostin AG 1295 (6,7-Dimethyl-2-phenylquinoxaline), which is a selective inhibitor of tyrosine kinase in platelet-derived growth factor (PDGF) receptor; or combinations thereof.

In some embodiments, the PDGF receptor tyrosine kinase inhibitor is JNJ-10198409, which has the following structure.

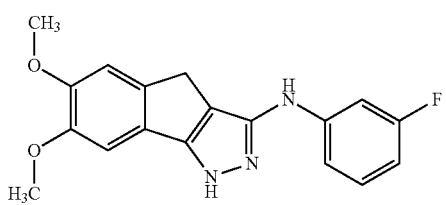 [SMILES: COc1cc2c(cc1OC)-c1[nH]nc(Nc3cccc(F)c3)c1C2]

The PDGF receptor tyrosine kinase inhibitor can be in the form of a hydrate or salt of any of the foregoing compounds.

The PDGF receptor tyrosine kinase inhibitors can be used at a variety of concentrations. For example, when used in a solution the PDGF receptor tyrosine kinase inhibitors can be used at about 0.001 micromolar to about 50 millimolar, or about 0.01 micromolar to about 10 millimolar, or about 0.01 μM to about 10 μM, or about 0.05 μM to about 9 μM, or about 0.1 μM to about 8 μM, or about 0.2 μM to about 7 μM, or about 0.3 μM to about 6 μM, or about 0.3 μM to about 4 μM, or about 0.5 μM to about 2 μM. In a dry formulation, the PDGF receptor tyrosine kinase inhibitors can be present in amounts of about 0.1 mg to about 4 g, or about 0.5 mg to about 3 g, or about 1.0 mg to about 2 g, or about 1.5 mg to about 1 g.

In some embodiments, the reprogramming medium can include CHIR99021 (e.g., at about 10-20 μM), A83-01 (e.g., at about 0.5-1.0 µM), SC1 (e.g., at about 0.5-1.0 µM), OAC (e.g., at about 1-10 µM), Y27632 (e.g., at about 5-10 µM), BIX-01294 (e.g., at about 0.5-2.0 µM), AS8351 (e.g., at about 1.0-3.0 µM), SU16f (e.g., at about 2-5 µM), and JNJ-10198409 (e.g., at about 0.05-0.2 µM). This medium is also referred to as the 9C composition or medium. As described herein PBIT (e.g., at about 10 µM) can be used in place of AS8351.

Cardiac Cell Maturation

After incubation of cells in a reprogramming medium, the cells can be contacted with (e.g., incubated in) a cardiac induction medium to promote maturation of the reprogrammed cells. A first cardiac induction medium (CIM1) can be employed that contains a combination of a glycogen synthase kinase 3 (GSK3) inhibitor, and growth factors such as a bone morphogenic protein, a member of the TGFβ family, vascular endothelial growth factor (VEGF), or any combination thereof.

The glycogen synthase kinase 3 (GSK3) inhibitor employed in the cardiac induction medium can be any GSK3 inhibitor, including any of the GSK3 inhibitors described herein. In some embodiments, the GSK3 inhibitor is CHIR99021.

The growth factors can include BMP4, a TGFβ family member such as Activin A and VEGF.

Bone morphogenetic protein-4 (BMP-4) is a member of the group of bone morphogenic proteins and a ventral mesoderm inducer. BMPs are expressed in adult human bone marrow (BM) and play a role in bone remodeling and growth. BMP-4 can modulate the proliferative and differentiation potential of hematopoietic progenitor cells.

BMP-4 can be included in a defined culture medium at a concentration of about 5-100 ng/mL, about 20-100 ng/mL, about 20-50 ng/mL, about 10-30 ng/mL, about 15-30 ng/mL, about 20-30 ng/mL, or any range derivable therein. In certain embodiments, BMP-4 is included in the defined culture media at a concentration of about 5, 10, 15, 20, 25, 30, 35, 40, 45, or about 50 ng/mL.

Activin A is a member of the TGFβ family first identified in late 1980s as an inducer of follicle-stimulating hormone. Activin A is highly conserved in evolution and throughout the animal kingdom. It regulates a variety of biologic processes including cell proliferation, hematopoiesis, wound healing, and fibrosis. Activin A signals through the Activin type I (Alk2, 4, or 7) and type II (ActRII or ActRIIB) receptors and shares with TGFβ the activation of the Smad cascade. See, Phillips et al., *Cytokine Growth Factor Rev.* 20(2): 153-64 (2009); Werner, *Cytokine Growth Factor Rev.* 17(3): 157-71 (2006).

Activin A can be included in a defined culture medium at a concentration, for example, from about 5 ng/ml to about 200 ng/ml, or from about 10 ng/ml to about 175 ng/ml, or from about 15 ng/ml to about 150 ng/ml, or from about 20 ng/ml to about 150 ng/ml, or from about 25 ng/ml to about 125 ng/ml, or from about 30 ng/ml to about 100 ng/ml, or from about 35 ng/ml to about 80 ng/ml, or from about 40 ng/ml to about 60 ng/ml, or about 50 ng/ml.

Vascular endothelial growth factor (VEGF) is a signaling protein involved in formation of the embryonic circulatory system and angiogenesis. VEGF can stimulate endothelial cell mitogenesis and cell migration.

VEGF can be included in a defined culture medium at a concentration of from about 10-100 ng/mL, about 20-100 ng/mL, about 10-50 ng/mL, about 15-30 ng/mL, about 20-30 ng/mL, about 20-50 ng/mL, or any range derivable therein. In certain embodiments, VEGF is included in the defined culture media at a concentration of about 2.5, 5, 10, 15, 20, 25, 30, 35, 40, 45, or about 50 ng/mL.

After incubation in a first cardiac induction medium (CIM1) that contains a combination of a glycogen synthase kinase 3 (GSK3) inhibitor, and growth factors such as a bone morphogenic protein, a member of the TGFβ family, vascular endothelial growth factor (VEGF), or any combination thereof, the cells can be incubated in a second cardiac induction medium (CIM2).

The second cardiac induction medium (CIM2) is conditioned medium collected from human embryonic stem cell-derived cardiomyocytes. The CIM2 can be conditioned medium collected from either human embryonic stem cell-derived cardiomyocytes or induced pluripotent stem cell-derived cardiomyocytes. Human induced pluripotent stem (iPS) cell-derived cardiomyocytes can be obtained from Cellular Dynamics International (see website at cellulardynamics.com/products/cardiomyocytes.html?gclid=CJ_ise2bsrkCFUSi4AodzkkAtg).

The second cardiac induction medium (CIM2) is collected after incubation of the cell culture medium with such embryonic stem cell-derived cardiomyocytes for at least 1 day, or at least 2 days. Cells are removed from the second cardiac induction medium, for example, by collection of medium through centrifugation, followed by passage of the medium through a 0.45 um filter to eliminate any remaining cells or cell debris before use. The underlying basal medium for the second cardiac induction medium can be any of the media described in this application. For example, the underlying basal medium for the second cardiac induction medium can be RPMI1640 supplemented with 2% B27 (from Life Technologies).

Starting Cells

A starting population of cells can be derived from essentially any source, and can be heterogeneous or homogeneous. In certain embodiments, the cells to be treated as described herein are adult cells, including essentially any accessible adult cell type(s). In other embodiments, the cells used according to the invention are adult stem cells, progenitor cells, or somatic cells. In still other embodiments, the cells treated with any of the compositions and/or methods described herein include any type of cell from a newborn, including, but not limited to newborn cord blood, newborn stem cells, progenitor cells, and tissue-derived cells (e.g., somatic cells). Accordingly, a starting population of cells that is reprogrammed by the compositions and/or methods described herein, can be essentially any live somatic cell type.

As illustrated herein, fibroblasts can be reprogrammed to cross lineage boundaries and to be directly converted to another cell type such as a cardiac progenitor cell or a cardiomyocyte cell type.

Various cell types from all three germ layers have been shown to be suitable for somatic cell reprogramming by genetic manipulation, including, but not limited to liver and stomach (Aoi et al., *Science* 321(5889):699-702 (2008); pancreatic β cells (Stadtfeld et al., *Cell Stem Cell* 2: 230-40 (2008); mature B lymphocytes (Hanna et al., *Cell* 133: 250-264 (2008); human dermal fibroblasts (Takahashi et al., *Cell* 131, 861-72 (2007); Yu et al., *Science* 318(5854) (2007); Lowry et al., *Proc Natl Acad Sci USA* 105, 2883-2888 (2008); Aasen et al., *Nat Biotechnol* 26(11): 1276-84 (2008); meningiocytes (Qin et al., *J Biol Chem* 283(48): 33730-5 (2008); neural stem cells (DiSteffano et al., *Stem Cells Devel.* 18(5): (2009); and neural progenitor cells (Eminli et al., *Stem Cells* 26(10): 2467-74 (2008). Any such cells can be reprogrammed and/or programmed by use of the compositions and methods described herein.

The cells can be autologous or allogeneic cells (relative to a subject to be treated or who may receive the cells).

Reprogramming Methods

Starting cells are treated for a time and under conditions sufficient to convert the starting cells across lineage and/or differentiation boundaries to form cardiac progenitor cells and/or cardiomyocytes.

Cells can be incubated with a reprogramming composition that contains one or more GSK3 inhibitors/WNT agonists, TGF-beta inhibitors, inhibitors of extracellular signal-regulated kinase 1 (ERK1), inhibitors of Ras GTPase-activating protein (Ras-GAP)), Oct-4 activators, p160ROCK inhibitors (where p160ROCK is a rho-associated protein kinase), iron chelator and/or KDM5B inhibitor, inhibitors of G9a histone methyltransferase, inhibitors of various growth factor receptors such as PDGF receptor beta, protein kinase receptor inhibitors, inhibitors of PDGF-BB receptor, and any combination thereof. The composition can contain at least two of the agents, or at least three of the agents, or at least four of the agents, or at least five of the agents, or at least six of the agents, or at least seven of the agents, or at least eight of the agents.

After incubation in a reprogramming medium, the cells can then incubated in the first and/or second cardiac induction media.

The base media employed to which the reprogramming agents or induction agents are added can be a convenient cell culture medium.

The term "cell culture medium" (also referred to herein as a "culture medium" or "medium") as referred to herein is a medium for culturing cells containing nutrients that maintain cell viability and support proliferation. The cell culture medium can contain any of the following in an appropriate combination: salt(s), buffer(s), amino acids, glucose or other sugar(s), antibiotics, serum or serum replacement, and other components such as peptide growth factors, etc. Cell culture media ordinarily used for particular cell types are available to those skilled in the art.

Examples cell culture media that can be employed include mTESR-1® medium (StemCell Technologies, Inc., Vancouver, Calif.), or Essential 8® medium (Life Technologies, Inc.) on a Matrigel substrate (BD Biosciences, NJ) or on a Corning® Synthemax surface, or in Johansson and Wiles CDM supplemented with insulin, transferrin, lipids and polyvinyl alcohol (PVA) as substitute for Bovine Serum Albumin (BSA). Examples of commercially available media also include, but are not limited to, Dulbecco's Modified Eagle's Medium (DMEM), Minimal Essential Medium (MEM), Basal Medium Eagle (BME), RPMI 1640, Ham's F-10, Ham's F-12, a-Minimal Essential Medium (aMEM), Glasgow's Minimal Essential Medium (G-MEM), Iscove's Modified Dulbecco's Medium, or a general purpose media modified for use with pluripotent cells, such as X-VIVO (Lonza) or a hematopoietic base media.

The starting cells can be dispersed in a cell culture medium that contains the reprogramming composition at a density that permits cell expansion. For example, about 1 to $10^{10}$ cells can be contacted with the reprogramming composition in a selected cell culture medium, especially when the cells are maintained at a cell density of about 1 to about $10^8$ cells per milliliter, or at a density of about 100 to about $10^7$ cells per milliliter, or at a density of about 1000 to about $10^6$ cells per milliliter.

The time for conversion of starting cells into cardiac progenitor and cardiomyocyte cells can vary. For example, the starting cells can be incubated with the reprogramming composition until cardiac or cardiomyocyte cell markers are expressed. Such cardiac or cardiomyocyte cell markers can include any of the following markers: α-Actinin, MLC2v, MY20, cMHC, NKX2-5, MEF2c, GATA4, ISL1, cTNT, cTNI, MLC2a and any combination thereof.

Incubation can proceed in any of the compositions described herein, for example, until early stage cardiac progenitor markers are expressed by the starting cells. Such early stage cardiac progenitor markers include GATA4, ISL1 or a combination thereof. The early stage cardiac progenitor markers such as GATA4 and/or ISL1 can be expressed by about 6 days, or by about 8 days, or by about 9 days, or by about 10 days, or by about 11 days, or by about 12 days of incubation of cells using the compositions and methods described herein.

Further incubation of the cells can be performed until expression of late stage cardiac progenitor markers such as NKX2-5, MEF2c or a combination thereof occurs. The late stage cardiac progenitor marker such as NKX2-5 and/or MEF2c can be expressed by about 14 days, or by about 15 days, or by about 16 days, or by about 17, or by about 18 days of incubation of cells using the compositions and methods described herein.

In some embodiments, the starting cells can be incubated with the reprogramming medium under cell culture conditions for about 1 day to about 15 days, or about 2 days to about 12 days, or about 3 days to about 10 days, or about 4 days to about 8 days, or about 5 days to about 7 days, or about 6 days.

After incubation in the reprogramming medium, maturation of the cardiac phenotype can be induced by incubation of the cells in a first cardiac induction medium (e.g., CIM1) for about 1 day to about 20 days, or about 2 days to about 14 days, or about 3 days to about 8 days, or about 4 days to about 6 days, or about 5 days.

After incubation in such a first cardiac induction medium (e.g., CIM1), the cells can be replated into a second cardiac induction medium (e.g., CIM2), and incubated for about 1 day to about 40 days, or about 3 days to about 36 days, or about 5 days to about 33 days, or about 7 days to about 30 days, or about 10 days to about 27 days, or about 15 days to about 25 days, or about 20 to about 22 days.

Cardiomyocytes exhibit some cardiac-specific electrophysiological properties. One electrical/physiological characteristic is an action potential, which is a short-lasting event in which the difference of potential between the interior and the exterior of each cardiac cell rises and falls following a consistent trajectory. Another electrophysiological characteristic of cardiomyocytes is the cyclic variations in the cytosolic-free $Ca^{2+}$ concentration, named as $Ca^{2+}$ transients, which are employed in the regulation of the contraction and relaxation of cardiomyocytes. These characteristics can be detected and evaluated to assess whether a population of cells has been reprogrammed into cardiomyocytes.

Such methods can therefore be used to generate a population of cardiac progenitor cells or cardiomyocytes that can be transplanted into a subject or used for experimentation.

In some embodiments, a reprogrammed population of cells (at various stages of reprogramming) can be frozen at liquid nitrogen temperatures, stored for periods of time, and then thawed for use at a later date. If frozen, a population of reprogrammed cells can be stored in a 10% DMSO, 50% FCS, within 40% RPMI 1640 medium. Once thawed, the cells can be expanded by culturing the cells in an appropriate medium that can contain selected growth factors, vitamins, feeder cells, and other components selected by a person of skill in the art.

Treatment

The reprogrammed cells and compositions of compounds (with or without reprogrammed cells) that are described herein can also be employed in a method of treating a subject with a cardiac disease or condition.

Examples of diseases and conditions that can be treated using the reprogrammed cells and/or compositions (containing any of the compounds described herein with or without reprogrammed cells) include any cardiac pathology or cardiac dysfunction. Diseases and conditions that can be treated include those that occur as a consequence of genetic defect, physical injury, environmental insult or conditioning, bad health, obesity and other disease risks.

The terms "cardiac pathology" or "cardiac dysfunction" are used interchangeably and refer to any impairment in the heart's pumping function. This includes, for example, impairments in contractility, impairments in ability to relax (sometimes referred to as diastolic dysfunction), abnormal or improper functioning of the heart's valves, diseases of the heart muscle (sometimes referred to as cardiomyopathies), diseases such as angina pectoris, myocardial ischemia and/or infarction characterized by inadequate blood supply to the heart muscle, infiltrative diseases such as amyloidosis and hemochromatosis, global or regional hypertrophy (such as may occur in some kinds of cardiomyopathy or systemic hypertension), and abnormal communications between chambers of the heart.

As used herein, the term "cardiomyopathy" refers to any disease or dysfunction of the myocardium (heart muscle) in which the heart is abnormally enlarged, thickened and/or stiffened. As a result, the heart muscle's ability to pump blood is usually weakened. The etiology of the disease or disorder may be, for example, inflammatory, metabolic, toxic, infiltrative, fibroplastic, hematological, genetic, or unknown in origin. There are two general types of cardiomyopathies: ischemic (resulting from a lack of oxygen) and non-ischemic.

Ischemic cardiomyopathy is a chronic disorder caused by coronary artery disease (a disease in which there is atherosclerotic narrowing or occlusion of the coronary arteries on the surface of the heart). Coronary artery disease often leads to episodes of cardiac ischemia, in which the heart muscle is not supplied with enough oxygen-rich blood.

Non-ischemic cardiomyopathy is generally classified into three groups based primarily on clinical and pathological characteristics: dilated cardiomyopathy, hypertrophic cardiomyopathy and restrictive and infiltrative cardiomyopathy.

In another embodiment, the cardiac pathology is a genetic disease such as Duchenne muscular dystrophy and Emery Dreiffuss dilated cardiomyopathy.

For example, the cardiac pathology can be selected from the group consisting of congestive heart failure, myocardial infarction, cardiac ischemia, myocarditis and arrhythmia.

Administration of Reprogrammed Cells

Reprogrammed cells generated as described herein can be employed for tissue reconstitution or regeneration in a human patient or other subjects in need of such treatment. The cells are administered in a manner that permits them to graft or migrate to a diseased or injured tissue site and to reconstitute or regenerate the functionally deficient area. Devices are available that can be adapted for administering cells, for example, to cardiac tissues.

For therapy, reprogrammed cardiac progenitor cells, cardiomyocytes and/or pharmaceutical compositions can be administered locally or systemically. A population of reprogrammed cells can be introduced by injection, catheter, implantable device, or the like. A population of reprogrammed cells can be administered in any physiologically acceptable excipient or carrier that does not adversely affect the cells. For example, the cardiac progenitor cells, cardiomyocytes and/or pharmaceutical compositions can be administered intravenously or through an intracardiac route (e.g., epicardially or intramyocardially). Methods of administering the cardiac progenitor cells, cardiomyocytes and/or pharmaceutical compositions of the invention to subjects, particularly human subjects, include injection or implantation of the cells into target sites in the subjects. The cells of the invention can be inserted into a delivery device which facilitates introduction of the cells after injection or implantation of the device within subjects. Such delivery devices include tubes, e.g., catheters, for injecting cells and fluids into the body of a recipient subject. The tubes can additionally include a needle, e.g., a syringe, through which the cells of the invention can be introduced into the subject at a desired location. The kits described herein can include such devices.

The cardiac progenitor cells and cardiomyocytes can be inserted into such a delivery device, e.g., a syringe, in different forms. A population of reprogrammed cells can be supplied in the form of a pharmaceutical composition. Such a composition can include an isotonic excipient prepared under sufficiently sterile conditions for human administration. For general principles in medicinal formulation, the reader is referred to CELL THERAPY: STEM CELL TRANSPLANTATION, GENE THERAPY, AND CELLULAR IMMUNOTHERAPY, by G. Morstyn & W. Sheridan eds, Cambridge University Press, 1996; and HEMATOPOIETIC STEM CELL THERAPY, E. D. Ball, J. Lister & P. Law, Churchill Livingstone, 2000. The choice of the cellular excipient and any accompanying constituents of the composition that includes a population of reprogrammed cells can be adapted to optimize administration by the route and/or device employed.

As used herein, the term "solution" includes a carrier or diluent in which the cardiomyocytes of the invention remain viable. Carriers and diluents which can be used with this aspect of the invention include saline, aqueous buffer solutions, physiologically acceptable solvents, and/or dispersion media. The use of such carriers and diluents is well known in the art. The solution is preferably sterile and fluid to allow syringability. For transplantation, a solution containing a suspension of cardiomyocytes can be drawn up into a syringe, and the solution containing the cells can be administrated to anesthetized transplantation recipients. Multiple injections may be made using this procedure.

The compositions, cardiac progenitor cells and/or cardiomyocytes can also be embedded in a support matrix. A composition that includes a population of reprogrammed cells can also include or be accompanied by one or more other ingredients that facilitate engraftment or functional mobilization of the reprogrammed cells. Suitable ingredients include matrix proteins that support or promote adhesion of the reprogrammed cells, or complementary cell types, such cardiac pacemaker cells, or cardiac cells at different stages of maturation. In another embodiment, the composition may include physiologically acceptable matrix scaffolds. Such physiologically acceptable matrix scaffolds can be resorbable and/or biodegradable.

The population of reprogrammed cells generated by the methods described herein can include low percentages of non-cardiac cells (e.g., fibroblasts). For example, a population of reprogrammed cells for use in compositions and for administration to subjects can have less than about 90% non-cardiac cells, less than about 85% non-cardiac cells, less than about 80% non-cardiac cells, less than about 75% non-cardiac cells, less than about 70% non-cardiac cells, less than about 65% non-cardiac cells, less than about 60% non-cardiac cells, less than about 55% non-cardiac cells, less than about 50% non-cardiac cells, less than about 45% non-cardiac cells, less than about 40% non-cardiac cells, less than about 35% non-cardiac cells, less than about 30% non-cardiac cells, less than about 25% non-cardiac cells, less than about 20% non-cardiac cells, less than about 15% non-cardiac cells, less than about 12% non-cardiac cells, less than about 10% non-cardiac cells, less than about 8% non-cardiac cells, less than about 6% non-cardiac cells, less than about 5% non-cardiac cells, less than about 4% non-cardiac cells, less than about 3% non-cardiac cells, less than about 2% non-cardiac cells, or less than about 1% non-cardiac cells of the total cells in the cell population.

Many cell types are capable of migrating to an appropriate site for regeneration and differentiation within a subject. To determine the suitability of various therapeutic administration regimens and dosages of cell compositions, the cells can first be tested in a suitable animal model. At one level, cells are assessed for their ability to survive and maintain their phenotype in vive. Cells can also be assessed to ascertain whether they migrate to diseased or injured sites in vivo, or to determine an appropriate dosage such as an appropriate number of cells and/or a frequency of administration of cells. Cell compositions can be administered to immunodeficient animals (such as nude mice, or animals rendered immunodeficient chemically or by irradiation). Tissues can be harvested after a period of regrowth, and assessed as to whether the administered cells or progeny thereof are still present, are alive, and/or have migrated to desired or undesired locations.

Injected cells can be traced by a variety of methods. For example, cells containing or expressing a detectable label (such as green fluorescent protein, or beta-galactosidase) can readily be detected. The cells can be pre-labeled, for example, with BrdU or [$^3$H]-thymidine, or by introduction of an expression cassette that can express green fluorescent protein, or beta-galactosidase. Alternatively, the reprogrammed cells can be detected by their expression of a cell marker that is not expressed by the animal employed for testing (for example, a human-specific antigen). The presence and phenotype of the administered population of reprogrammed cells can be assessed by fluorescence microscopy (e.g., for green fluorescent protein, or beta-galactosidase), by immunohistochemistry (e.g., using an antibody against a human antigen), by ELISA (using an antibody against a human antigen), or by RT-PCR analysis using primers and hybridization conditions that cause amplification to be specific for human polynucleotides.

The dose and the number of administrations can therefore be optimized by those skilled in the art.

Pharmaceutical Compositions

The invention also relates to reprogramming compositions containing one or more of the following chemical agents: a GSK3 inhibitor, a WNT agonist, a TGF-beta inhibitor, an inhibitor of extracellular signal-regulated kinase 1 (ERK1), an inhibitor of Ras GTPase-activating protein (Ras-GAP), an Oct-4 activator, a p160ROCK inhibitor (where p160ROCK is a rho-associated protein kinase), an iron chelator and/or KDM5B inhibitor, an inhibitor of G9a histone methyltransferase, an inhibitor of various growth factor receptors such as PDGF receptor beta, a protein kinase receptor inhibitor, an inhibitor of PDGF-BB receptor, and any combination thereof. For example, the composition can contain at least two of the agents, or at least three of the agents, or at least four of the agents, or at least five of the agents, or at least six of the agents, or at least seven of the agents, or at least eight of the agents, or at least nine of the agents. The compositions can also contain reprogrammed cells.

For example, such a reprogramming composition (9C) can include CHIR99021, A83-01, SC1, OAC, Y27632, BIX-01294, AS8351, SU16f, and JNJ-10198409. As described herein PBIT can be employed instead of AS8351.

The invention also relates to separate cardiac induction compositions containing one or more of the following chemical agents: a glycogen synthase kinase 3 (GSK3) inhibitor, and growth factors such as a bone morphogenic protein, a member of the TGFβ family, vascular endothelial growth factor (VEGF), or any combination thereof.

The compositions of the invention can be pharmaceutical compositions. In some embodiments, the compositions can include a pharmaceutically acceptable carrier. By "pharmaceutically acceptable" it is meant a carrier, diluent, excipient, and/or salt that is compatible with the other ingredients of the formulation, and not deleterious to the recipient thereof.

The compositions can contain any of the agent(s) or compound(s) described herein in an amount sufficient to reprogram a cell into a cardiac cell type. For example, the compositions can contain any of the agent(s) or compound(s) described herein in an amount sufficient to induce a cell to express cardiac or cardiomyocyte cell markers. Such cardiac or cardiomyocyte cell markers can include any of the following markers: α-Actinin, MLC2v, MY20, cMHC, NKX2-5, MEF2c, GATA4, ISL1, cTNT, cTNI, MLC2a and any combination thereof. Incubation can proceed in any of the compositions described herein, for example, until early stage cardiac progenitor markers are expressed by the starting cells. Such early stage cardiac progenitor markers include GATA4. ISL1 or a combination thereof. The early stage cardiac progenitor markers such as GATA4 and/or ISL1 can be expressed by about 6 days, or by about 8 days, or by about 9 days, or by about 10 days, or by about 11 days, or by about 12 days of incubation of cells using the compositions and methods described herein.

In some embodiments, the therapeutic compositions are administered in a "therapeutically effective amount." Such a therapeutically effective amount is an amount sufficient to obtain the desired physiological effect, e.g., treatment of a condition, disorder, disease and the like or reduction in symptoms of the condition, disorder, disease and the like. For example, the therapeutic agents can be administered to treat any of the conditions, disorders, or diseases described herein. Examples include congestive heart failure, myocardial infarction, cardiac ischemia myocarditis, arrhythmia or any combination thereof.

To achieve the desired effect(s), the composition can be formulated in single or divided dosages. For example, a GSK3 inhibitor, a WNT agonist, a TGF-beta inhibitor, an inhibitor of extracellular signal-regulated kinase 1 (ERK1), an inhibitor of Ras GTPase-activating protein (Ras-GAP), an Oct-4 activator, a p160ROCK inhibitor (where p160ROCK is a rho-associated protein kinase), an iron chelator and/or KDM5B inhibitor, an inhibitor of G9a histone methyltransferase, an inhibitor of various growth factor receptors such as PDGF receptor beta, a protein kinase receptor inhibitor, an inhibitor of PDGF-BB receptor, and/or a growth factor (e.g., any of the CIM1 growth factors) can present in the composition in amounts specified above or in dosages of at least about 0.01 mg/kg to about 500 to 750 mg/kg, of at least about 0.01 mg/kg to about 300 to 500 mg/kg, at least about 0.1 mg/kg to about 100 to 300 mg/kg or at least about 1 mg/kg to about 50 to 100 mg/kg of body weight, although other dosages may provide beneficial results. The amount administered will vary depending on various factors including, but not limited to the combination of compounds chosen for administration, the disease, the weight, the physical condition, the health, the age of the mammal, as well as other physiological factors. Such factors can be readily determined by the clinician employing animal models or other test systems that are available in the art.

For example, a reprogramming composition can include CHIR99021 (e.g., at about 10-20 µM). A83-01 (e.g., at about 0.5-1.0 µM), SC1 (e.g., at about 0.5-1.0 µM), OAC (e.g., at about 1-10 µM), Y27632 (e.g., at about 5-10 µM), BIX-01294 (e.g., at about 0.5-2.0 µM), AS8351 (e.g., at about 1.0-3.0 µM), SU16f (e.g., at about 2-5 µM), and JNJ-10198409 (e.g., at about 0.05-0.2 µM). As described herein PBIT (e.g., at about 10 µM).

Reprogrammed cells can be included in the compositions in varying amounts depending upon the disease or injury to be treated. For example, the compositions can be prepared in liquid form for local or systemic administration containing about $10^3$ to about $10^{12}$ reprogrammed cells, or about $10^4$ to about $10^{10}$ reprogrammed cells, or about $10^5$ to about $10^8$ reprogrammed cells. One or more of the following types of compounds can also be present in the composition with the cells: a GSK3 inhibitor, a WNT agonist, a TGF-beta inhibitor, an inhibitor of extracellular signal-regulated kinase 1 (ERK1), an inhibitor of Ras GTPase-activating protein (Ras-GAP), an Oct-4 activator, a p160ROCK inhibitor (where p160ROCK is a rho-associated protein kinase), an iron chelator and/or KDM5B inhibitor, an inhibitor of G9a histone methyltransferase, an inhibitor of various growth factor receptors such as PDGF receptor beta, a protein kinase receptor inhibitor, an inhibitor of PDGF-BB receptor, and/or one or more growth factors (e.g., any of the CIM1 growth factors).

Administration of the composition may be in a single dose, in multiple doses, in a continuous or intermittent manner, depending, for example, upon the recipient's physiological condition, whether the purpose of the administration is for response to traumatic injury or for more sustained therapeutic purposes, and other factors known to skilled practitioners. Similarly, cell(s) can be contacted with the composition in a continuous manner, or intermittently, depending upon the need for reprogrammed cells, the manufacturing schedule, the convenience of workers, and/or the selected recipient's physiological condition. The administration or contacting of the cells with compositions of the invention may be essentially continuous over a preselected period of time or may be in a series of spaced doses. Both local and systemic administration to recipients and/or subjects is contemplated.

To prepare the composition, the compounds are synthesized and/or the cells are generated, and the components are purified as necessary or desired. The compounds, cells, and/or other agents can be suspended in a pharmaceutically acceptable carrier. If the composition contains only compounds, without cells, the composition can be lyophilized. These compounds and cells can be adjusted to an appropriate concentration, and optionally combined with other agents. The absolute weight of a given compound and/or other agent included in a unit dose can vary widely. For example, about 0.01 to about 2 g, or about 0.1 to about 500 mg, of at least one compound can be administered. Alternatively, the unit dosage can vary from about 0.01 g to about 50 g, from about 0.01 g to about 35 g, from about 0.1 g to about 25 g, from about 0.5 g to about 12 g, from about 0.5 g to about 8 g, from about 0.5 g to about 4 g, or from about 0.5 g to about 2 g.

Daily doses of the compounds can vary as well. Such daily doses can range, for example, from about 0.1 g/day to about 50 g/day, from about 0.1 g/day to about 25 g/day, from about 0.1 g/day to about 12 g/day, from about 0.5 g/day to about 8 g/day, from about 0.5 g/day to about 4 g/day, and from about 0.5 g/day to about 2 g/day.

It will be appreciated that the amount of compounds and cells for use in treatment will vary not only with the particular carrier selected but also with the route of administration, the nature of the condition being treated and the age and condition of the patient. Ultimately, the attendant health care provider may determine proper dosage. A pharmaceutical composition may be formulated with the appropriate ratio of each compound in a single unit dosage form for administration with or without cells. Cells can be separately provided and either mixed with a liquid solution of the compound composition, or administered separately.

The compounds can also be formulated for sustained release (for example, using microencapsulation, see WO 94/07529, and U.S. Pat. No. 4,962,091). The formulations may, where appropriate, be conveniently presented in discrete unit dosage forms and may be prepared by any of the methods well known to the pharmaceutical arts. Such methods may include the step of mixing the therapeutic agent with liquid carriers, solid matrices, semi-solid carriers, finely divided solid carriers or combinations thereof, and then, if necessary, introducing or shaping the product into the desired delivery system.

One or more suitable unit dosage forms containing the compounds and/or the reprogrammed cells can be administered by a variety of routes including parenteral (including subcutaneous, intravenous, intramuscular and intraperitoneal), intracranial, intraspinal, oral, rectal, dermal, transdermal, intrathoracic, intrapulmonary and intranasal (respiratory) routes.

The compositions of the invention may be prepared in many forms that include aqueous solutions, suspensions, tablets, hard or soft gelatin capsules, and liposomes and other slow-release formulations, such as shaped polymeric gels. However, administration of cells often involves parenteral or local administration in an aqueous solution. Similarly, compositions containing cells and/or compounds can be administered in a device, scaffold, or as a sustained release formulation.

Thus while compositions containing only compounds can be administered in an oral dosage form, compositions containing cells are administered locally or systemically as non-oral formulations. When compositions contain only compounds, those compositions can be formulated as oral dosage forms so that the compounds are released into the stomach for quick absorption or in the intestine after passing through the stomach. Different types of formulating procedures are described in U.S. Pat. No. 6,306,434 and in the references contained therein. Alternatively, the compositions can be administered locally, for example, at the site of cardiac injury or disease, and/or at the site of natural cardiomyocyte generation.

Liquid pharmaceutical compositions may be in the form of, for example, aqueous or oily suspensions, solutions, emulsions, syrups or elixirs, dry powders for constitution with water or other suitable vehicles before use. Such liquid pharmaceutical compositions may contain conventional additives such as suspending agents, emulsifying agents, non-aqueous vehicles (which may include edible oils), or preservatives.

Compounds and/or cells can be formulated for parenteral administration (e.g., by injection, for example, bolus injection or continuous infusion) and may be presented in unit dosage form in ampoules, prefilled syringes, small volume infusion containers or multi-dose containers with an added preservative. The pharmaceutical compositions can take the form of suspensions, solutions, or emulsions in oily or aqueous vehicles, and can contain formulatory agents such as suspending, stabilizing and/or dispersing agents. Suitable carriers include saline solution, phosphate buffered saline, and other materials commonly used in the art.

The compositions can also contain other ingredients such as agents useful for treatment of cardiac diseases, conditions and injuries, such as, for example, an anticoagulant (e.g., dalteparin (fragmin), danaparoid (organan), enoxaparin (lovenox), heparin, tinzaparin (innohep), and/or warfarin (coumadin)), an antiplatelet agent (e.g., aspirin, ticlopidine, clopidogrel, or dipyridamole), an angiotensin-converting enzyme inhibitor (e.g., Benazepril (Lotensin), Captopril (Capoten), Enalapril (Vasotec), Fosinopril (Monopril), Lisinopril (Prinivil, Zestril), Moexipril (Univasc), Perindopril (Aceon), Quinapril (Accupril), Ramipril (Altace), and/or Trandolapril (Mavik)), angiotensin II receptor blockers (e.g., Candesartan (Atacand), Eprosartan (Teveten), Irbesartan (Avapro), Losartan (Cozaar), Telmisartan (Micardis), and/or Valsartan (Diovan)), a beta blocker (e.g., Acebutolol (Sectral), Atenolol (Tenormin), Betaxolol (Kerlone), Bisoprolol/hydrochlorothiazide (Ziac), Bisoprolol (Zebeta), Carteolol (Cartrol), Metoprolol (Lopressor, Toprol XL), Nadolol (Corgard), Propranolol (Inderal), Sotalol (Betapace), and/or Timolol (Blocadren)), Calcium Channel Blockers (e.g., Amlodipine (Norvasc, Lotrel), Bepridil (Vascor), Diltiazem (Cardizem, Tiazac), Felodipine (Plendil), Nifedipine (Adalat, Procardia), Nimodipine (Nimotop), Nisoldipine (Sular), Verapamil (Calan, Isoptin, Verelan), diuretics (e.g, Amiloride (Midamor), Bumetanide (Bumex), Chlorothiazide (Diuril), Chlorthalidone (Hygroton), Furosemide (Lasix), Hydro-chlorothiazide (Esidrix, Hydrodiuril), Indapamide (Lozol) and/or Spironolactone (Aldactone)), vasodilators (e.g., Isosorbide dinitrate (Isordil), Nesiritide (Natrecor), Hydralazine (Apresoline), Nitrates and/or Minoxidil), statins, nicotinic acid, gemfibrozil, clofibrate, Digoxin, Digitoxin, and/or Lanoxin.

Additional agents can also be included such as antibacterial agents, antimicrobial agents, anti-viral agents, biological response modifiers, growth factors, immune modulators, monoclonal antibodies and/or preservatives. The compositions of the invention may also be used in conjunction with other forms of therapy.

Supplementary factors can be included in the compositions and/or in a cell culture media containing any of the cells, compositions, compounds or agents described herein. Examples of such supplementary factors include bone morphogenic protein (BMP)-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, brain derived neurotrophic factor, ciliary neurotrophic factor, cytokine-induced neutrophil chemotactic factor 1, cytokine-induced neutrophil chemotactic factor 2α, cytokine-induced neutrophil chemotactic factor 2β, β endothelial cell growth factor, endothelin 1, epidermal growth factor, epithelial-derived neutrophil attractant, fibroblast growth factor (FGF) 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor (acidic), fibroblast growth factor (basic), growth related protein, growth related protein α, growth related protein β, growth related protein γ, heparin binding epidermal growth factor, hepatocyte growth factor, insulin-like growth factor I, insulin-like growth factor II, insulin-like growth factor binding protein, keratinocyte growth factor, leukemia inhibitory factor, neurotrophin-3, neurotrophin-4, placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, pre-B cell growth stimulating factor, stem cell factor, transforming growth factor a, transforming growth factor β, transforming growth factor β1, transforming growth factor β1.2, transforming growth factor β2, transforming growth factor β3, latent transforming growth factor β1, transforming growth factor β binding protein I, transforming growth factor β binding protein II, transforming growth factor β binding protein III, and vascular endothelial growth factor.

Exemplary cytokines can be included such as interleukin (IL)-1, IL-2, IL-3, IL-4, IL-5, IL-6, IL-7, IL-8, IL-9, IL-10, IL-11, IL-12, IL-13, IL-14, IL-15, IL-16, IL-17, IL-18, interferon (IFN), IFN-γ, tumor necrosis factor (TNF), TNF1, TNF2, TNF-α, macrophage colony stimulating factor (M-CSF), granulocyte-monocyte colony stimulating factor (GM-CSF), granulocyte colony stimulating factor (G-CSF), megakaryocyte colony stimulating factor (Meg-CSF)-thrombopoietin, stem cell factor, and erythropoietin. Chemokines can also be included such as IP-10 and Stromal Cell-Derived Factor 1α.

Exemplary hormones contemplated for inclusion in the compositions and/or cell culture media described herein can include, but are not limited to, steroid hormones and peptide hormones, such as insulin, somatostatin, growth hormone, hydrocortisone, dexamethasone, 3,3',5-Triiodo-L-thyronine, and L-Thyroxine.

Kits

A variety of kits are described herein that include any of the compositions, compounds and/or agents described herein. The compounds and/or agents described herein can be packaged separately into discrete vials, bottles or other containers. Alternatively, any of the compounds and/or agents described herein can be packaged together as a single composition, or as two or more compositions that can be used together or separately. The compounds and/or agents described herein can be packaged in appropriate ratios and/or amounts to facilitate conversion of selected cells across differentiation boundaries to form cardiac progenitor cells and/or cardiomyocytes.

A kit is described herein for culture of cells in vitro that can include any of the compositions, compounds and/or agents described herein, as well as instructions for using those compositions, compounds and/or agents. Some kits can include a cell culture or cell media that includes any of the compositions, compounds and/or agents described herein. The kits can include one or more sterile cell collection devices such as a swab, skin scrapping device, a needle, a syringe, and/or a scalpel. The kits can also include antibodies for detection of cardiac progenitor and/or cardiomyocyte cell markers such as antibodies against any of the following markers: α-Actinin, MLC2v, MY20, cMHC, NKX2-5, GATA4, ISL1, NKX2-5, MEF2c, cTNT, cTNI, MLC2a, and any combination thereof. The antibodies can be labeled so that a detectable signal can be observed when the antibodies form a complex with the cardiac progenitor cell and/or cardiomyocytes cell marker(s).

The instructions can include guidance for culturing cells for a time and under conditions sufficient to convert a selected cell (e.g., a starting cell) across differentiation boundaries and into the cardiac lineage. For example, the instructions can describe amounts of the compositions, compounds and/or agents described herein to add to cell culture media, times sufficient to convert cells to the cardiac lineage, maintenance of appropriate cell densities for optimal conversion, and the like. For example, the instructions can describe procedures for rehydration or dilution of the compositions, compounds and/or agents described herein. When a kit provides a cell culture medium containing some of the compositions, compounds and/or agents described herein, the instructions can describe how to add other compounds and/agents. The instructions can also describe how to convert the selected cells to cardiac progenitor cells or to cardiomyocytes.

The instructions can also describe procedures for detecting cardiac progenitor and/or cardiomyocyte cell markers by use of antibodies against those markers so that the extent of conversion and/or differentiation can be assessed.

Another kit is also described herein that includes any of the compositions, compounds and/or agents described herein for therapeutic treatment of a subject. The kit can include any of the compositions, compounds and/or agents described herein, as well as instructions for administering those compositions, compounds and/or agents. Such instructions can provide the information described throughout this application.

The kit can also include cells. For example, the kit can include chemically induced cardiac progenitor cells and/or cardiomyocytes that have been treated by the compositions and/or methods described herein and that are ready for administration.

The cells, compositions and/or compounds can be provided within any of the kits in the form of a delivery device. Alternatively a delivery device can be separately included in the kit(s), and the instructions can describe how to assemble the delivery device prior to administration to a subject. The delivery device can provide a scaffold for cell growth and/or a matrix for controlled release of any of the compositions, compounds or agents described herein.

Any of the kits can also include syringes, catheters, scalpels, sterile containers for sample or cell collection, diluents, pharmaceutically acceptable carriers, and the like.

The kits can provide other factors such as any of the supplementary factors or drugs described herein for the compositions in the preceding section.

Definitions

Cardiomyocytes or cardiac myocytes are the muscle cells that make up the cardiac muscle. Each myocardial cell contains myofibrils, which are long chains of sarcomeres, the contractile units of muscle cells. Cardiomyocytes show striations similar to those on skeletal muscle cells, but unlike multinucleated skeletal cells, they contain only one nucleus. Cardiomyocytes have a high mitochondrial density, which allows them to produce ATP quickly, making them highly resistant to fatigue. Mature cardiomyocytes can express one or more of the following cardiac markers: α-Actinin, MLC2v, MY20, cMHC, NKX2-5, GATA4, cTNT, cTNI, MEF2c, MLC2a, or any combination thereof. In some embodiments, the mature cardiomyocytes express NKX2-5, MEF2c or a combination thereof. Cardiac progenitor cells express early stage cardiac progenitor markers such as GATA4, ISL1 or a combination thereof.

As used herein, the term "functional cardiomyocyte" refers to a differentiated cardiomyocyte that is able to send or receive electrical signals. In some embodiments, a cardiomyocyte is said to be a functional cardiomyocyte if it exhibits electrophysiological properties such as action potentials and/or $Ca^{2+}$ transients.

As used herein, a "differentiated non-cardiac cell" can refer to a cell that is not able to differentiate into all cell types of an adult organism (i.e., is not a pluripotent cell), and which is of a cellular lineage other than a cardiac lineage (e.g., fibroblast, a cell of endodermal, mesodermal, epithelial, neuronal, connective, lymphocyte, or other tissue type lineage). Differentiated cells include, but are not limited to, multipotent cells, oligopotent cells, unipotent cells, progenitor cells, and terminally differentiated cells. In particular embodiments, a less potent cell is considered "differentiated" in reference to a more potent cell.

As used herein, a cell that differentiates into a mesodermal, ectodermal or endodermal lineage defines a cell that becomes committed to a specific mesodermal, ectodermal or endodermal lineage, respectively. Examples of cells that differentiate into a mesodermal lineage or give rise to specific mesodermal cells include, but are not limited to, cells that are adipogenic, chondrogenic, cardiogenic, dermatogenic, hematopoietic, hemangiogenic, myogenic, nephrogenic, urogenitogenic, osteogenic, pericardiogenic, or stromal. Examples of cells that differentiate into ectodermal lineage include, but are not limited to epidermal cells, neurogenic cells, and neurogliagenic cells. Examples of cells that differentiate into endodermal lineage include, but are not limited to pleurigenic cells, and hepatogenic cells, that give rise to the lining of the intestine, and cells that give rise to pancreogenic and splanchogenic cells.

A "somatic cell" is a cell forming the body of an organism. Somatic cells include cells making up organs, skin, blood, bones and connective tissue in an organism, but not germ cells.

Cells can be from, e.g., human or non-human mammals. Exemplary non-human mammals include, but are not limited to, mice, rats, cats, dogs, rabbits, guinea pigs, hamsters, sheep, pigs, horses, bovines, and non-human primates. In some embodiments, a cell is from an adult human or non-human mammal. In some embodiments, a cell is from a neonatal human, an adult human, or non-human mammal.

As used herein, the term "totipotent" means the ability of a cell to form all cell lineages of an organism. For example, in mammals, only the zygote and the first cleavage stage blastomeres are totipotent.

As used herein, the term "pluripotent" means the ability of a cell to form all lineages of the body or soma (i.e., the embryo proper). For example, embryonic stem cells are a type of pluripotent stem cells that are able to form cells from each of the three germs layers, the ectoderm, the mesoderm, and the endoderm.

As used herein, the term "multipotent" refers to the ability of an adult stem cell to form multiple cell types of one lineage. For example, hematopoietic stem cells are capable of forming all cells of the blood cell lineage, e.g., lymphoid and myeloid cells.

As used herein, the term "oligopotent" refers to the ability of an adult stem cell to differentiate into only a few different cell types. For example, lymphoid or myeloid stem cells are capable of forming cells of either the lymphoid or myeloid lineages, respectively.

As used herein, the term "unipotent" means the ability of a cell to form a single cell type. For example, spermatogonial stem cells are only capable of forming sperm cells.

As used herein, the term "direct reprogramming" or "transdifferentiation" refers to the generation of a cell of a certain lineage (e.g., a cardiac cell) from a different type of cell (e.g., a fibroblast cell) without an intermediate process of de-differentiating the cell into a cell exhibiting pluripotent stem cell characteristics.

As used herein, the terms "subject" or "patient" refers to any animal, such as a domesticated animal, a zoo animal, or a human. The "subject" or "patient" can be a mammal like a dog, cat, bird, livestock, or a human. Specific examples of "subjects" and "patients" include, but are not limited to, individuals with a cardiac disease or disorder, and individuals with cardiac disorder-related characteristics or symptoms.

The following non-limiting Examples illustrate some of the experimental work involved in developing the invention.

EXAMPLE 1

Materials and Methods

This Example describes some of the materials and methods used in the development of the invention. For example, compositions that can be employed to generate human cardiomyocytes from fibroblast cells are described herein. Briefly stated, the fibroblasts were incubated with a cardiac reprogramming medium (CRM) for six days to initiate the cell fate conversion, and then the cells were incubated in a cardiac induction medium 1 (CIM1) for 5 days, followed by cardiac induction medium 2 (CIM2) to direct cardiogenesis. FIG. 1 illustrates the treatment regimen.

The cardiac reprogramming medium (CRM) contained nine of the following chemical agents: a GSK3 inhibitor, a WNT agonist, a TGF-beta inhibitor, an inhibitor of extracellular signal-regulated kinase 1 (ERK1), an inhibitor of Ras GTPase-activating protein (Ras-GAP), an Oct-4 activator, a p160ROCK inhibitor (where p160ROCK is a rho-associated protein kinase), an iron chelator and/or KDM5B inhibitor, an inhibitor of G9a histone methyltransferase, an inhibitor of various growth factor receptors such as PDGF receptor beta, a protein kinase receptor inhibitor, an inhibitor of PDGF-BB receptor, and any combination thereof.

More specifically the CRM contained a combination of nine small-molecule compounds including: CHIR99021, A83-01, SC1, OAC2, Y27632, BIX-01294, AS8351, SU16f, and JNJ-10198409. Detailed information about the compounds used is summarized in Table 1.

TABLE 1

Cardiac Reprogramming Medium Components

| Full Name | Target | Concentration (µM) | Molecular Weight |
|---|---|---|---|
| CHIR99021 | GSK3 Inhibition | 10-20 | 465.34 |
| A83-01 | TGFβ inhibition | 0.5-1 | 421.52 |
| SC1 | Dual inhibition of ERK1 and Ras-GAP | 0.5-1 | 550.54 |
| OAC2 | Activator of OCT4 | 1-10 | 236.30 |
| Y27632 | Inhibition of Rho-associated coiled coil forming protein serine/threonine kinase | 5-10 | 320.26 |
| BIX-01294 | Histone methyl transferase inhibition | 0.5-2 | 600.02 |
| AS8351 | Iron chelator and/or KDM5B inhibitor | 1-3 | 291.30 |
| SU16f | Platelet-derived growth factor receptor inhibition | 2-5 | 386.44 |
| JNJ-10198409 | platelet-derived growth factor tyrosine kinase inhibition | 0.05-0.2 | 325.34 |

The cardiac induction medium 1 (CIM1) contained a combination of the GSK inhibitor CHIR99021 and three growth factors including BMP4, Activin A and VEGF. The cardiac induction medium 2 (CIM2) is conditioned medium collected from human embryonic stem cell-derived cardiomyocytes or from induced pluripotent stem cell-derived cardiomyocytes.

EXAMPLE 2

Cardiac Reprogramming Medium Generates Cardiac Progenitor Cells and Cardiomyocytes This Example illustrates that cardiac progenitor cells are readily generated using the compositions and methods described herein.

Naïve human fibroblast CRL-2097 cells were treated with cardiac reprogramming medium for 6 days followed by treatment with cardiac induction medium 1 for 5 days and then cardiac induction medium 2 for 7 days. A portion of the cell population was fixed with 4% paraformaldehyde and analyzed by immunostaining for the expression of early stage cardiac progenitor markers including GATA4 and ISL1 at day 12, as well as late stage cardiac progenitor marker NKX2-5 and MEF2c at day 18.

Figure 2:
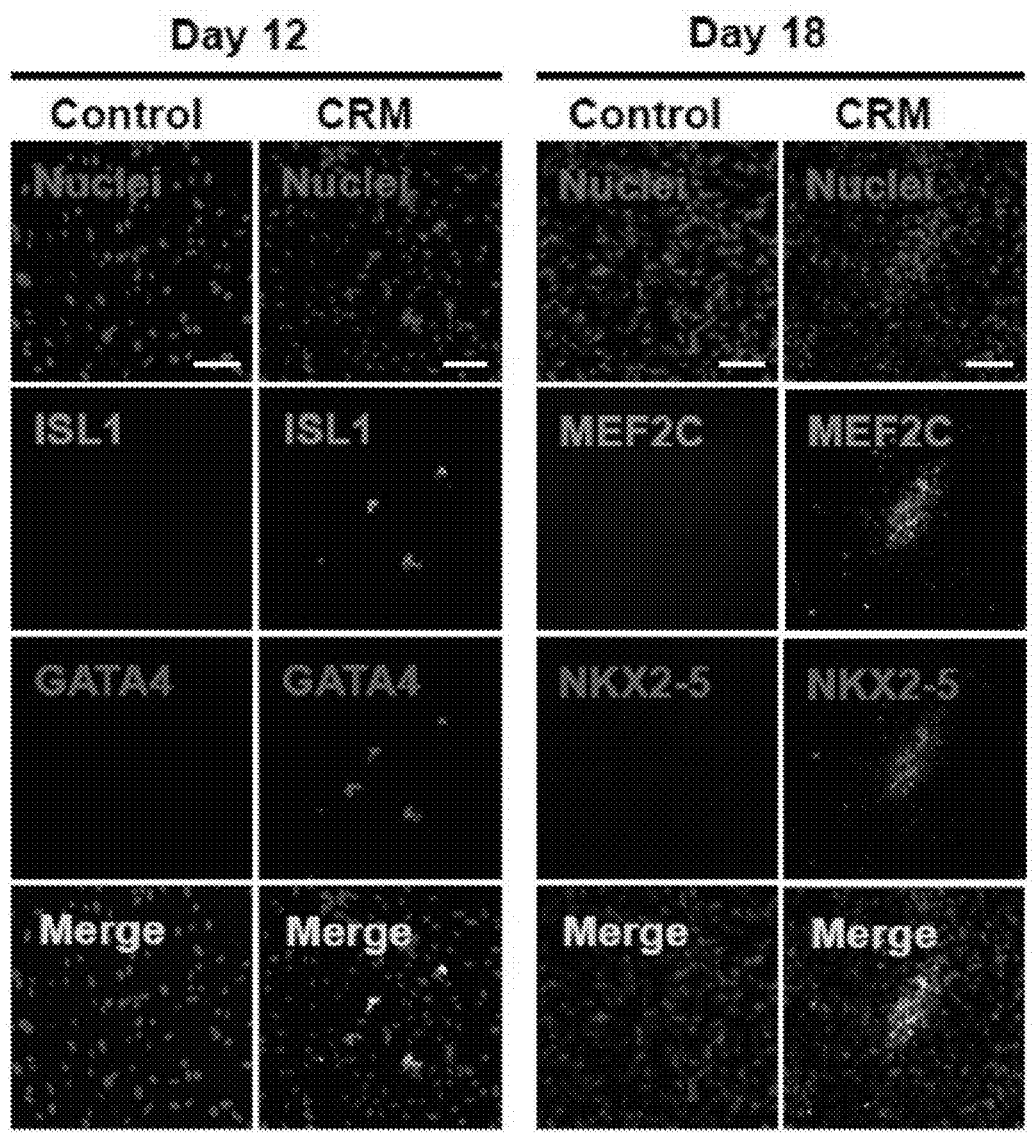
FIG. 2 illustrates that a cardiac progenitor cell population is present after reprogramming of the human dermal fibroblast cell line CRL-2097 using the compositions and methods described herein. As shown, the cells expressed early stage cardiac progenitor markers including GATA4 and ISL1 by day 12 of treatment. Cardiomyocyte-like cells that express the late stage cardiac progenitor markers NKX2-5 and MEF2c were generated after eighteen days of incubation with the cardiac reprogramming medium and the cardiac induction media.

FIG. 2 illustrates that cardiac progenitor cells form after twelve days of incubation of the human dermal fibroblast cell line CRL-2097 in the reprogramming medium. As shown, the cells expressed early stage cardiac progenitor markers including GATA4 and ISL1 by day 12. Also as shown in FIG. 2, cardiomyocyte-like cells are generated after eighteen days of incubation with the cardiac reprogramming medium and the cardiac induction media. As illustrated in FIG. 2, the cells express the late stage cardiac progenitor markers NKX2-5 and MEF2c by day 18.

EXAMPLE 3

Conversion Efficiency of Cardiac Reprogramming

This Example illustrates the efficiency of reprogramming fibroblasts into cardiac progenitor cells using the compositions and methods described herein.

Naïve human fibroblast CRL-2097 cells were treated with cardiac reprogramming medium for 6 days followed by treatment with cardiac induction medium 1 for 5 days and then cardiac induction medium 2 for 19 days as shown in FIG. 1. Cardiac troponin T (cTnT) was used as a typical protein marker of the cardiomyocytes cell type.

Figure 3:
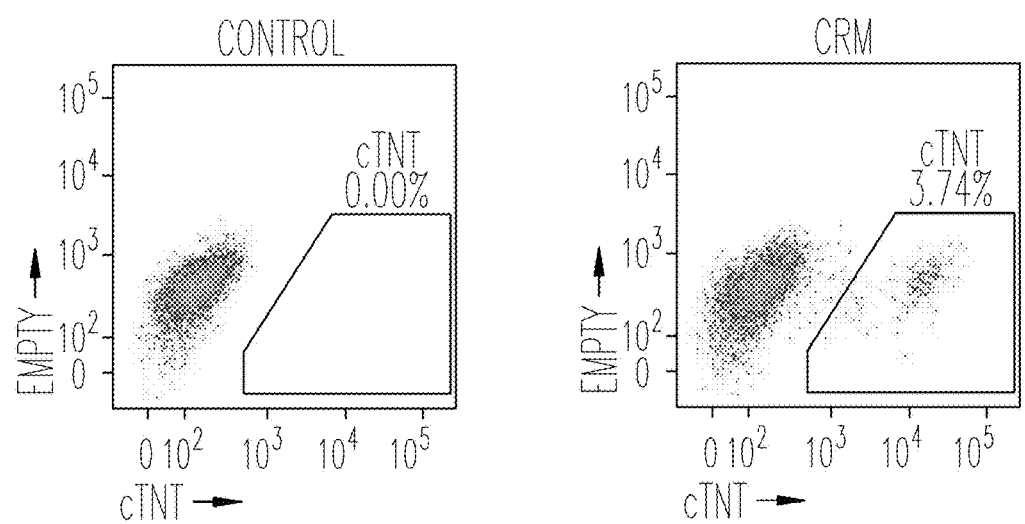
FIG. 3 illustrates the conversion efficiency of reprogramming human dermal fibroblast CRL-2097 cells into cardiomyocyte cells using the compositions and methods described herein. No control-treated cells expressed the cardiac-specific marker cTNT, but almost 4% of cells subjected to reprogramming expressed cTNT.

FIG. 3 depicts the percentage of cardiac troponin T (cTnT) positive cells after thirty (30) days of culture as assessed by flow cytometry. As shown, at least 3% of cTNT-cells were present in the population after use of the compositions and methods described herein.

EXAMPLE 4

Expression of Cardiac Markers by Reprogrammed Cells

This Example illustrates that cells treated with the compositions and methods described herein express cardiac cell markers such as α-Actinin, MLC2v, MY20, cMHC, NKX2-5, GATA4, cTNT, cTNI, and MLC2a.

Naïve human fibroblast CRL-2097 cells were treated with cardiac reprogramming medium for 6 days followed by treatment with cardiac induction medium 1 for 5 days and then cardiac induction medium 2 for 19 days. After such treatment for thirty days (day 30), the cell population was fixed with 4% paraformaldehyde and analyzed by immunostaining for the expression of a panel of cardiac-specific protein markers including: α-Actinin, MLC2v, MY20, cMHC, NKX2-5, GATA4, cTNT, cTNI, and MLC2a.

Figure 4:
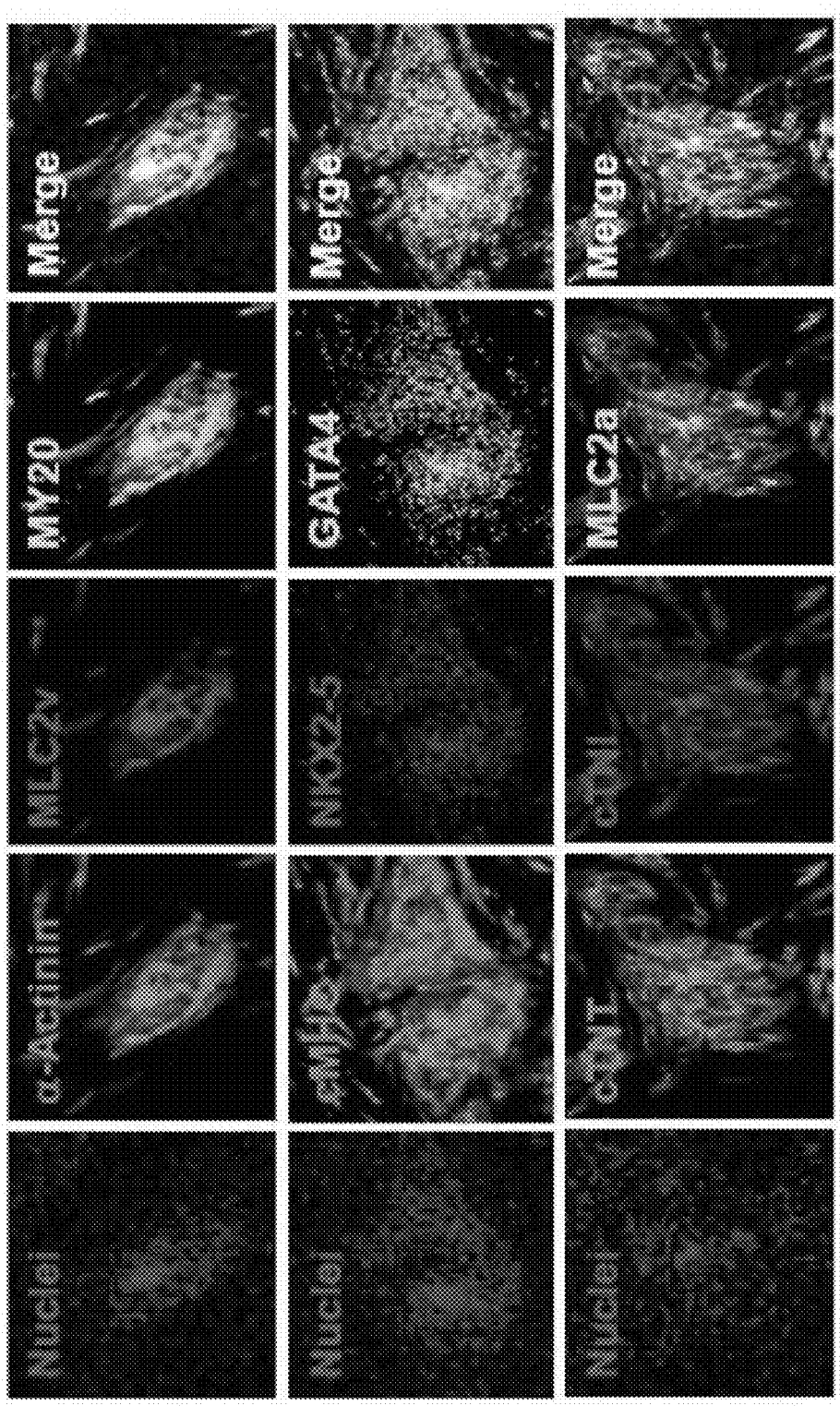

As shown in FIG. 4, after treatment with the compositions and methods described herein, the human fibroblast CRL-2097 cells express the following major cardiac markers: α-Actinin, MLC2v, MY20, cMHC, NKX2-5, GATA4, cTNT, cTNI, and MLC2a. Thus, cardiomyocyte-like cells have been reprogrammed from the human dermal fibroblast cell line CRL-2097.

EXAMPLE 5

Sarcomeric Structure and Cell-to-cell Connection of Reprogrammed Cells

This Example illustrates that cells treated with the compositions and methods described herein exhibit the sarcomeric structure and cell-to-cell connection of typical cardiomyocytes.

Naïve human fibroblast CRL-2097 cells were treated with cardiac reprogramming medium for 6 days followed by treatment with cardiac induction medium 1 for 5 days and then cardiac induction medium 2 for 19 days. At day 30, the tissues were digested into single cells or small clusters and then immunostained for the following: cardiac-specific myofilamental protein cTNT, cTNI, MLC2a, MLC2v, and α-Actinin, as well as cardiac gap junction protein Cx43.

Figure 5:
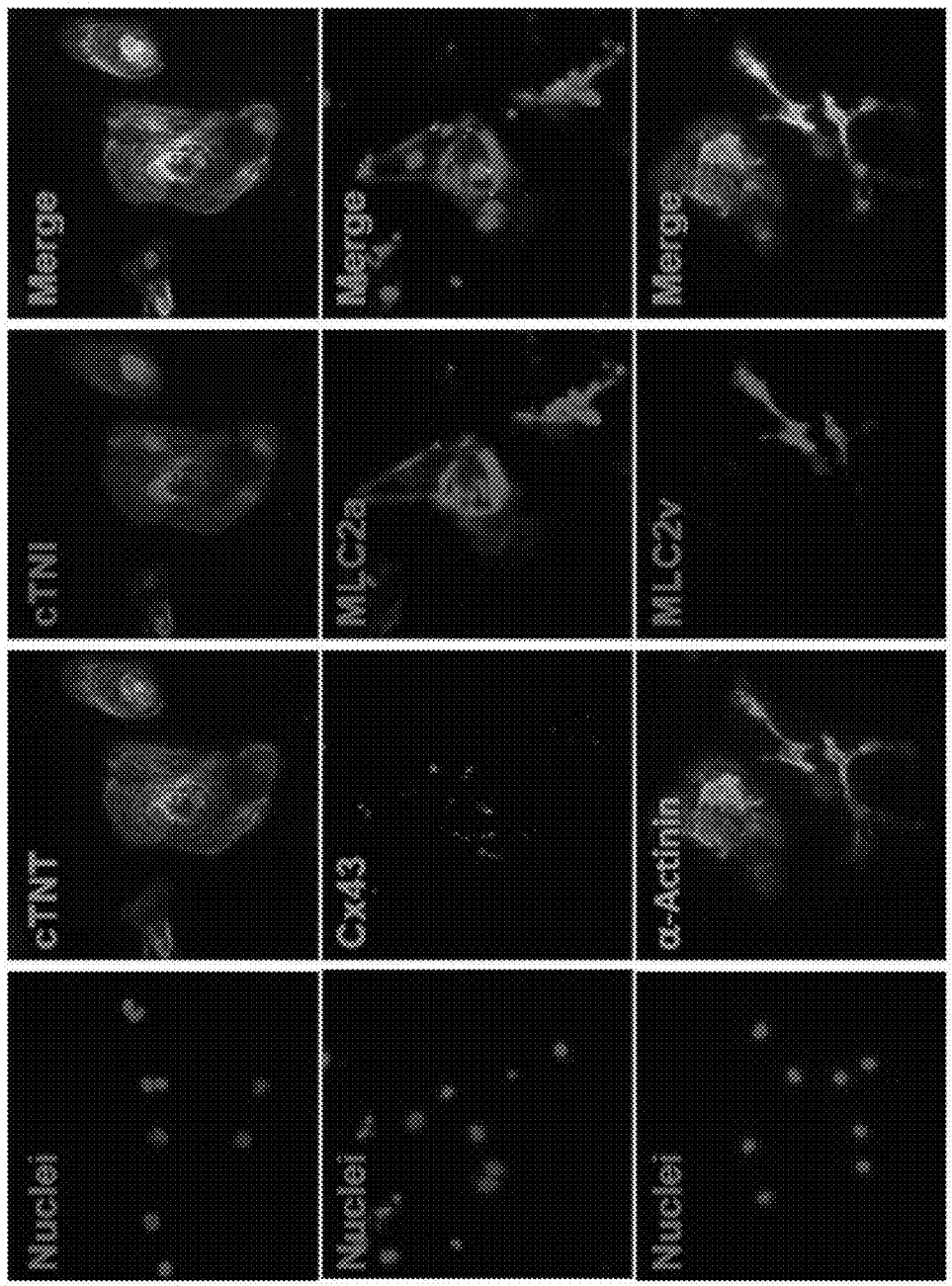
FIG. 5 illustrates that the cardiomyocyte cells reprogrammed from human dermal fibroblast cell line CRL-2097 possess a typical sarcomeric structure and cell-to-cell connections that are characteristic of cardiomyocytes.

FIG. 5 illustrates that the cardiomyocyte-like cells reprogrammed from human dermal fibroblast CRL-2097 cells possess a typical sarcomeric structure and cell-to-cell connections that are characteristic of cardiomyocytes.

EXAMPLE 6

Electrophysiological Properties of Reprogrammed Cells

This Example illustrates the electrophysiological properties of cells treated with the compositions and methods described herein.

Naïve human fibroblast CRL-2097 cells were treated with cardiac reprogramming medium for 6 days followed by treatment with cardiac induction medium 1 for 5 days and then cardiac induction medium 2 for 21-26 days.

Figure 6A:
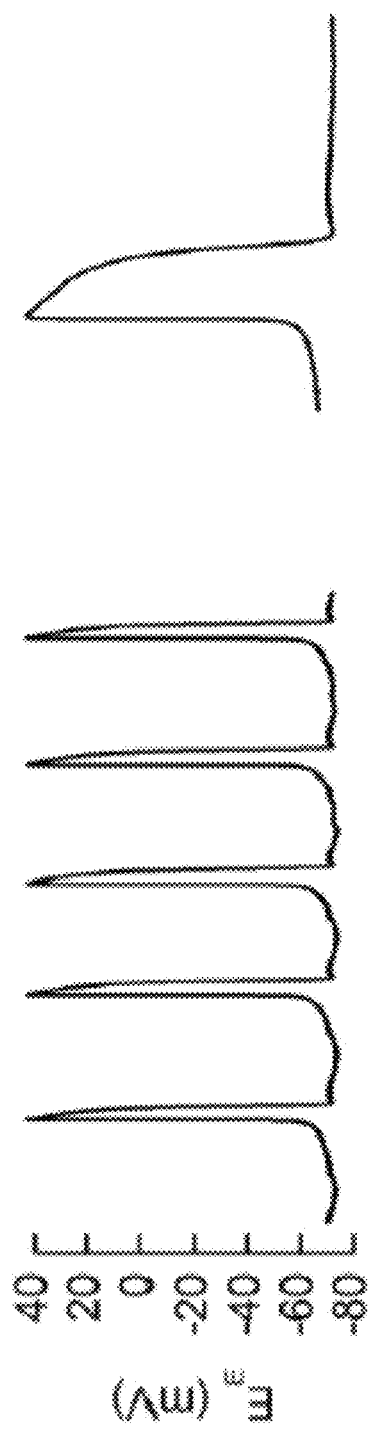
Figure 6B:
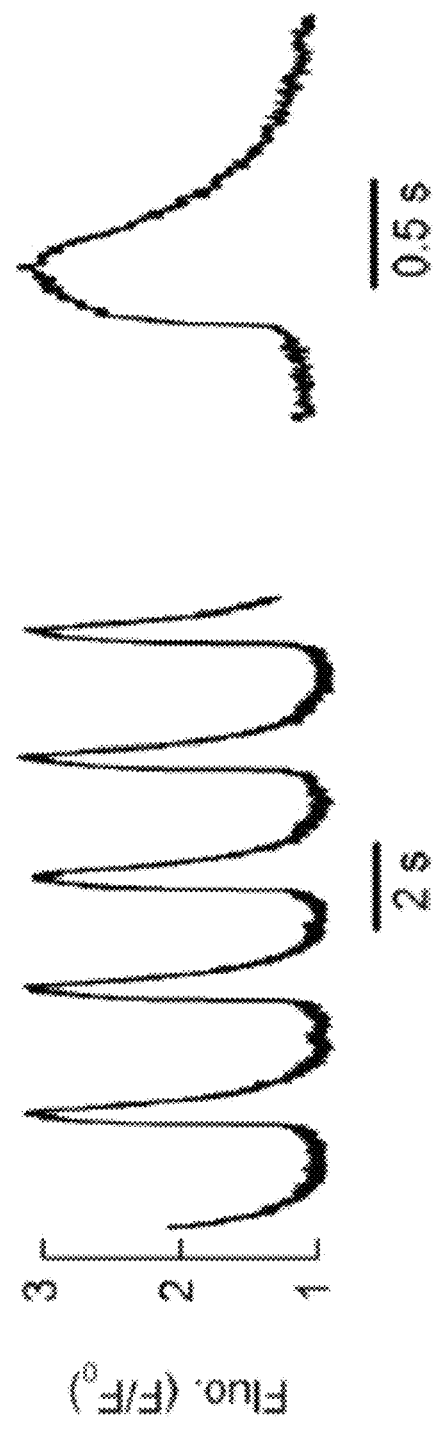

FIG. 6A shows representative action potentials recorded from a fibroblast-derived contracting cardiomyocyte at day 37. FIG. 6B shows representative $Ca^{2+}$ transients recorded from a fibroblast-derived contracting cardiomyocyte at day 37.

Table 2 summarizes the action potentials and $Ca^{2+}$ transients recorded from a fibroblast-derived contracting cardiomyocyte from day 32 to 37.

TABLE 2

Electrophysiological Properties of Reprogrammed Cells

| N | $V_{max}$ ($V \cdot s^{-1}$) | MDP (mV0 | OSP (mV) | $APD_{90}$ (ms) | Ca Transient ($F/F_0$) | Ca Transient $T_{10-90\%}$ (ms) |
|---|---|---|---|---|---|---|
| 15 | 58.8 ± 10.8 | −76.3 ± 1.1 | +37.9 ± 1.4 | 283.8 ± 32.9 | 3.4 ± 0.4 | 912.9 ± 66.8 |

When compared to the cell population generated by existing methods, the compositions and methods of the invention produce bona fide cardiomyocytes with typical functional characters of cardiac cells.

EXAMPLE 7

Responses of Reprogrammed Cells to β-Adrenergic and Muscarinic Stimulations

This Example illustrates the β-adrenergic or muscarinic responses of cardiomyocyte cells reprogrammed from fibroblasts.

Naïve human fibroblast CRL-2097 cells were treated with cardiac reprogramming medium for 6 days followed by treatment with cardiac induction medium 1 for 5 days and then cardiac induction medium 2 for 21-26 days.

Figure 7A:
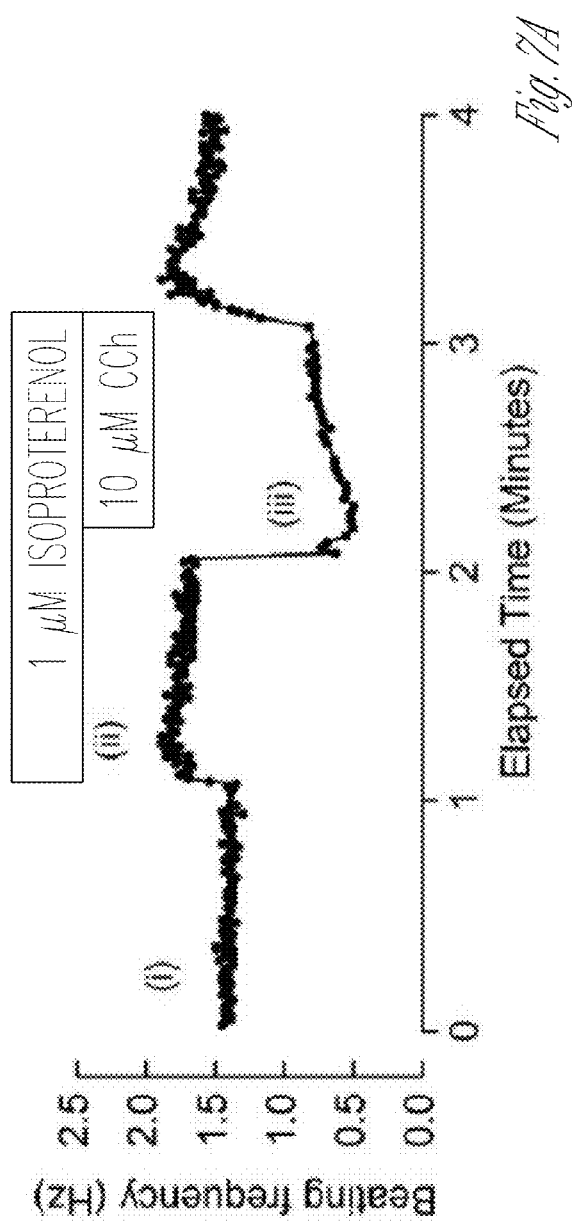
FIG. 7A-7B illustrate that cardiomyocyte cells reprogrammed from human dermal fibroblast cell line CRL-2097 possess responses to β-adrenergic and muscarinic stimulations that are characteristic of the signaling pathways exhibited by natural cardiomyocytes.

Representative beating frequencies of the reprogrammed cells are shown in FIG. 7A before (i) or after β-adrenergic stimulation by its agonist (ii, isoproterenol), or a muscarinic agonist (iii. Carbachol; CCh). As shown in FIG. 7A, isoproterenol significantly increased the beating frequency of the contracting cardiomyocytes derived from human fibroblast cells, whereas Cch had the opposite, negative effect.

Figure 7B:
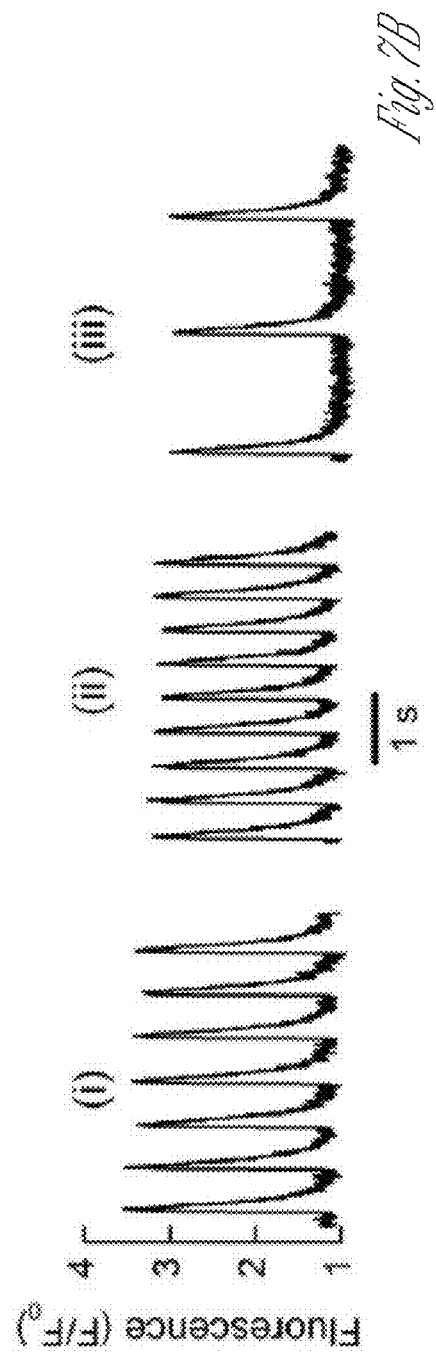

FIG. 7B shows representative $Ca^{2+}$ transients (i) of unstimulated reprogrammed cells, (ii) of β-adrenergic stimulated reprogrammed cells, and (iii) of muscarinic stimulated reprogrammed cells.

These data further confirm that the reprogrammed cells are of the cardiac lineage and demonstrate that the coupled β-adrenergic and muscarinic signaling cascades, as well as their associated intracellular signaling partners, are present and functional in the cardiomyocyte-like cells generated from human fibroblasts, e.g., human foreskin fibroblast

EXAMPLE 8

AS8351 can be Replaced by One or More Inhibitors of KDM5, a JmjC-domain-containing Histone Demethylase This Example describes experiments designed to investigate the role of AS8351, which appeared to be needed in the chemically-induced cardiac conversion process but whose role was poorly understood in a reprogramming context.

AS8351 and its functional analogues are thought to affect epigenetic modifications (Pogribny et al., 2013; Azad et al., 2013; Badal et al., 2015) by their ability to compete with α-ketoglutarate (α-KG) for chelating iron/Fe(II) in certain epigenetic enzymes, such as the JmjC-domain-containing histone demethylases (JmjC-KDMs) that require α-KG and iron as co-factors.

Figure 8A:
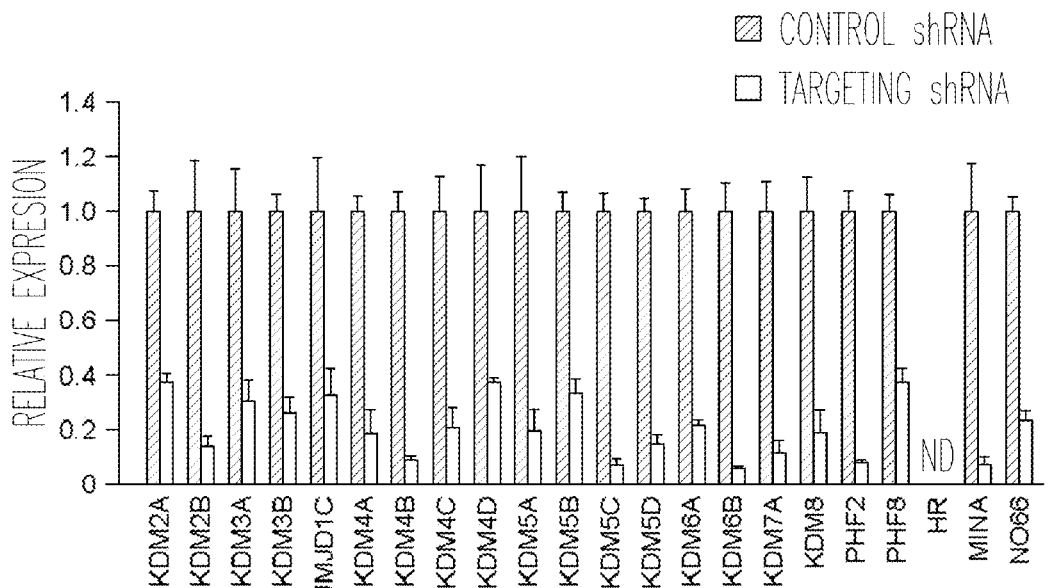
FIG. 8A-8G illustrates that AS8351 can facilitate the generation of chemically induced cardiomyocytes (ciCMs) by targeting KDM5B.

The inventors hypothesized that the effect of AS8351 on cardiac reprogramming might in part be mediated via modulation of a specific JmjC-KDM. To test this hypothesis, the inventors knocked down each of the 22 genes in the JmjC-KDM family by use of small hairpin RNAs (with >60% knockdown efficiency) (FIG. 8A) to assertion whether knock-down of any JmjC-KDMs could recapitulate AS8351's effect on cardiac reprogramming.

TABLE 3

Target sequences of shRNAs for specific gene knockdown experiments

| Gene target | shRNA No: | Sequence | SEQ ID NO: |
|---|---|---|---|
| KDM2A | 1# | TTCTGATGGACTCGGAATAAA | 1 |
| | 2# | GCTTACTCCACCGGCTGATAA | 2 |
| | 3# | ATGCCACGCTTCGCCTCATAA | 3 |
| KDM2B | 1# | CGGCCTTTACAAGAAGCATT | 4 |
| | 2# | CCTGAGGAAGAAGCGGAAATA | 5 |
| | 3# | CTGAACCACTGCAAGTCTATC | 6 |
| KDM3A | 1# | ACAACTTAGATTGGGTTTATA | 7 |
| | 2# | GCTTTGATTGTGAAGCATTTA | 8 |
| | 3# | ATGCCACGCTTCGCCTCATAA | 9 |
| KDM3B | 1# | GCGATCTTTGTAGAATTTGAT | 10 |
| | 2# | CCTCTGTGAAGCAGGTCTTTC | 11 |
| | 3# | CCCTAGTTCATCGCAACCTTT | 12 |
| JMJD1C | 1# | GGATCTGTGAGAAGCATATTT | 13 |
| | 2# | TCCACCTCCAGAGACTATAAA | 14 |
| | 3# | GCTCCTGTGATTCAATGTTAT | 15 |
| KDM4A | 1# | GCACCGAGTTTGTCTTGAAAT | 16 |
| | 2# | TTCGAGAGTTCCGCAAGATAG | 17 |
| | 3# | GACTGCTGTTTATGCTCATTA | 18 |
| KDM4B | 1# | GTGCTACTGCAATGCCCTACT | 19 |
| | 2# | ACTGAGCAACCTTTGAGATTG | 20 |
| | 3# | GTGGAAGCTGAAATGCGTGTA | 21 |
| KDM4C | 1# | CCTTGCATACATGGAGTCTAA | 22 |
| | 2# | GCAGAGAGTAATGGTGTGTTA | 23 |
| | 3# | GCCCAAGTCTTGGTATGCTAT | 24 |
| KDM4D | 1# | GGTTAGCGTAACCTGGTATAT | 25 |
| | 2# | CAGATTATCCACCCGTCAAAT | 26 |
| | 3# | CCTGGTATATGCAACTACCAT | 27 |
| KDM5A | 1# | CAACAGGTCAGACGCATTTAA | 28 |
| | 2# | CCAGACTTACAGGGACACTTA | 29 |
| | 3# | CCTTGAAAGAAGCCTTACAAA | 30 |
| KDM5B | 1# | ATCGCTTGCTTCATCGATATT | 31 |
| | 2# | CGAGATGGAATTAACAGTCTT | 32 |
| | 3# | GTGCCTGTTTACCGAACTAAT | 33 |
| KDM5C | 1# | GCCACACTTGAGGCCATAATC | 34 |
| | 2# | TCGCAGAGAAATCGGGCATTT | 35 |
| | 3# | AGTACCTGCGGTATCGGTATA | 36 |
| KDM5D | 1# | GCCACATTGGAAGCCATAATT | 37 |
| | 2# | AGTGGCACCAAAGGTCATTTG | 38 |
| | 3# | CCAGTGCTAGATCAGTCTGTT | 39 |

TABLE 3 -continued

Target sequences of shRNAs for specific gene knockdown experiments

| Gene target | shRNA No: | Sequence | SEQ ID NO: |
|---|---|---|---|
| KDM6A | 1# | CCGCGCAAATAGAAATAATTT | 40 |
| | 2# | GCACATAGACTAAGGAATAAA | 41 |
| | 3# | GATGCAAGTCTATGACCAATT | 42 |
| KDM6B | 1# | AGTCCCACTCACCTCTATTTA | 43 |
| | 2# | TCTGTACAGACCCTCGAAATC | 44 |
| | 3# | TTGAGCACAAACGGAACTATG | 45 |
| KDM7A | 1# | TATGGGATCAACAGGTATTTA | 46 |
| | 2# | TTAGACCTGGACACCTTATTA | 47 |
| | 3# | TGGATTTGATGTCCCTATTAT | 48 |
| KDM8 | 1# | GGAAGTACATCCGGCTGTATT | 49 |
| | 2# | CCTGTTCATCCCGGTGAAATA | 50 |
| | 3# | GCATCAGAAAGCCGAATGTTT | 51 |
| PHF2 | 1# | CATAGAATGTAGCGTGTAAAT | 52 |
| | 2# | TTGCTGACCAGGTCGACAAAT | 53 |
| | 3# | GAACGGGAAACTACTCCTTTA | 54 |
| PHF8 | 1# | CTGCAACTCTAGCCCTATATC | 55 |
| | 2# | ACGTTGGGAAGACGAGCAATA | 56 |
| | 3# | GCTGGCCAGTTGAGCTATAAT | 57 |
| HR | 1# | GAACGGAAGATCCAGGAGAAA | 58 |
| | 2# | GCAGNAGGAATCAACACAGAA | 59 |
| | 3# | CGGGCACAGAAAGACTTCCTT | 60 |
| MINA | 1# | GCAACGATTCAGTTTCACCAA | 61 |
| | 2# | GACCTGAAACTTACTACAGAT | 62 |
| | 3# | CAAACATGAGACCTCCCTGTT | 63 |
| NO66 | 1# | GATGCCTCTAGCCCTAAATTA | 64 |
| | 2# | ACCCTTGATCCGTGATCATTT | 65 |
| | 3# | GCCCAGTTGACAACAGAAACA | 66 |
| Control Non-targeting shRNA | | CAACAAGATGAAGAGCACCAA | 67 |

Figure 8B:
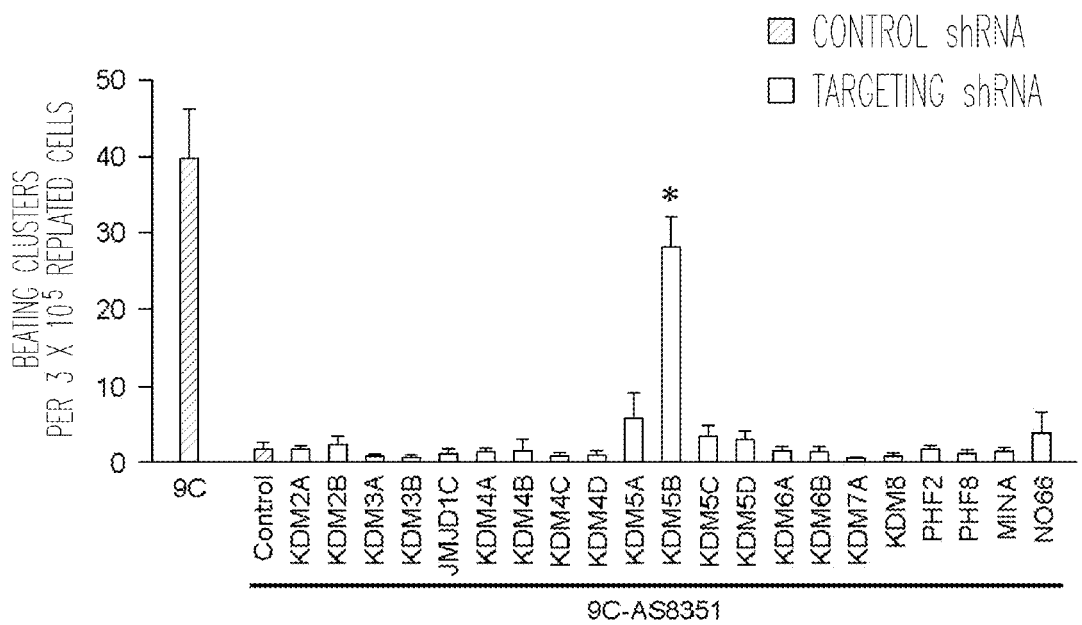
Figure 8C:
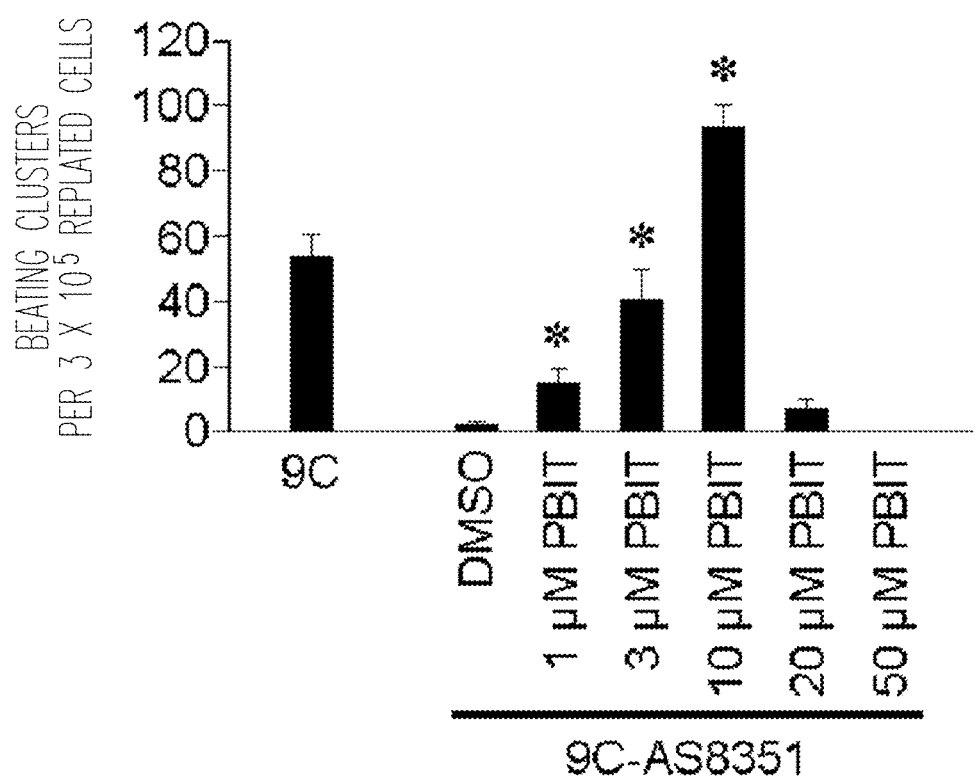
Figure 8D:
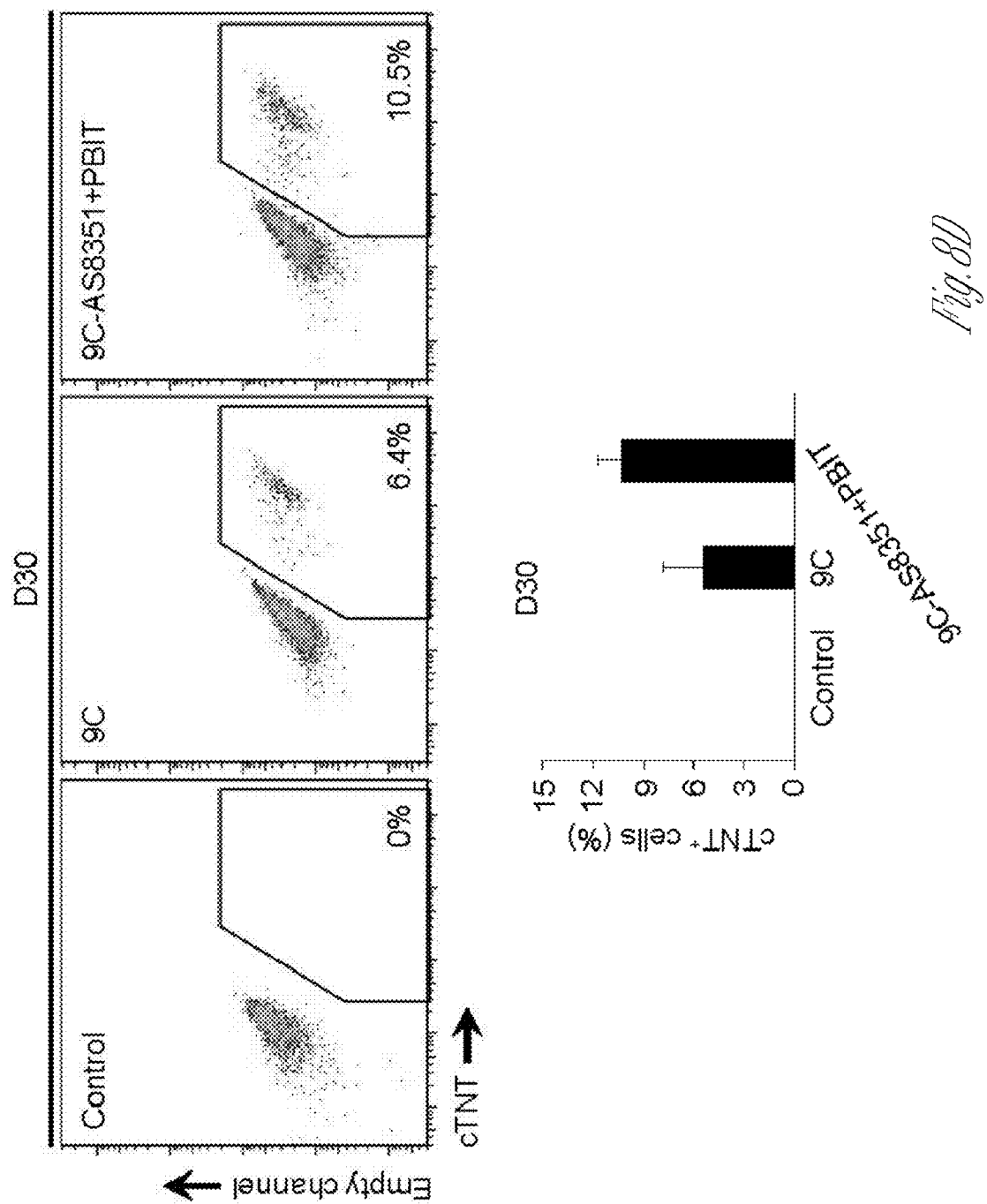

Notably, the inventors discovered that knockdown of KDM5B could effectively "phenocopy" AS8351 in generating beating clusters (FIG. 8B), suggesting that it might be a direct target of AS8351. This conclusion was further confirmed by using a KDM5B inhibitor, PBIT (Sayegh et al., 2013) (FIGS. 8C and 8D).

Figure 8E:
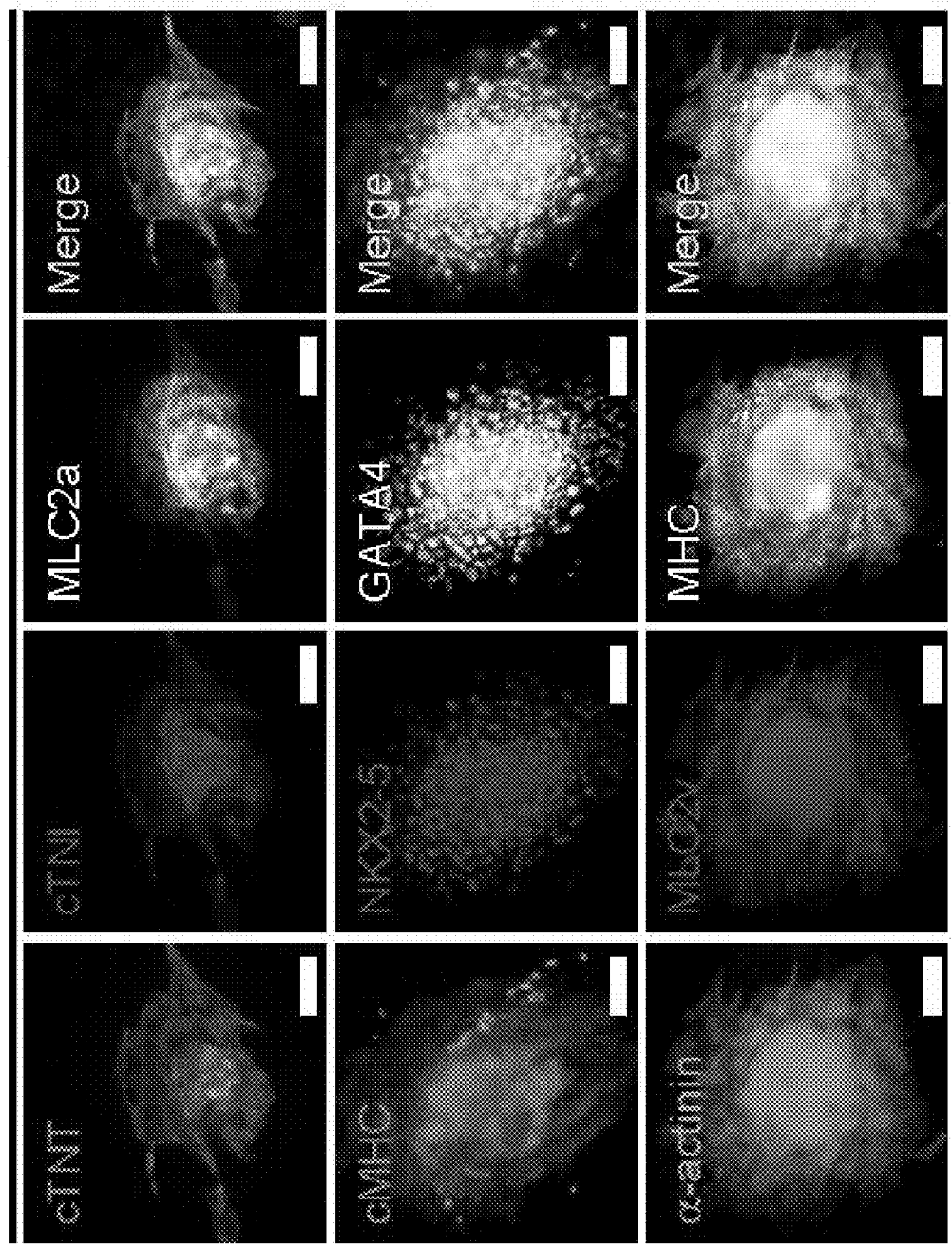
Figure 8H:
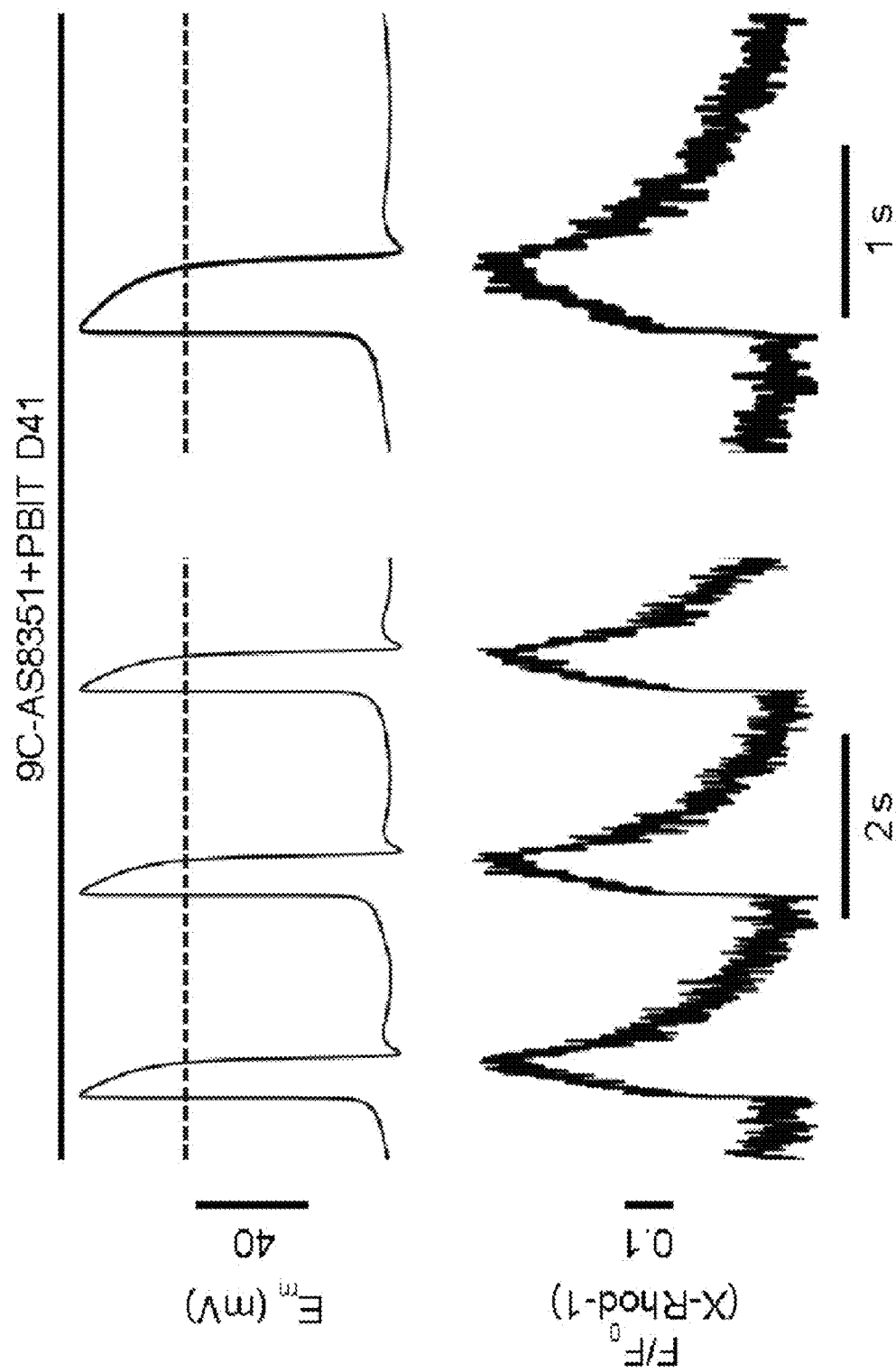

KDM5B catalyzes the demethylation of tri-, di-, and mono-methylation states of H3K4 and facilitates heterochromatin formation (Mosammaparast and Shi, 2010). The inventors have observed that one effect of the reprogramming compositions described herein is on re-opening closed chromatin structures. Hence, tests were performed to ascertain whether inhibition of KDM5B can facilitate this process and sustain active chromatin markers (i.e., H3K4 methylation) at specific genomic loci. Similar to observations when using the reprogramming process with AS8351 to generate chemically-induced cardiomyocytes, the cardiomyocytes generated by using 10 μM PBIT as a substitute for AS8351 expressed a broad panel of cardiac proteins (FIG. 8E) and exhibited CM-like electrophysiological features (FIGS. 8F and 8G).

EXAMPLE 9

Conversion of Human Adult Dermal Fibroblasts (HADFs) into Chemically Induced Cardiomyocytes Based on the success in converting human fetal and neonatal fibroblasts into fully reprogrammed cardiomyocytes, the inventors investigated whether the reprogramming compositions could be applied to reprogram HADFs.

Initially, contracting clusters were not observed from HADFs treated with reprogramming conditions, even after prolonged culture and tuning compounds' concentrations (FIGS. 9A and 9B, and some data not shown). HADFs are more senescent than fetal or neonatal fibroblasts and likely have established more stable epigenetic programs, accounting for greater refractoriness to reprogramming into pluripotency or the cardiac fate in vitro (Takahashi et al., 2007; Nam et al., 2013).

To overcome this senescent/epigenetic block, several rounds of additional screening were performed and a 7-day pretreatment with SMER28 was identified. SMER28 is a small molecule autophagy inducer (Sarkar et al., 2007). The pretreatment was done before reprogramming increased the proliferation of HADFs and enabled the generation of beating cardiac clusters. Pretreatment with sodium butyrate (NaB), a histone deacetylase inhibitor that promotes human induced pluripotent stem cell (hiPSC) reprogramming (Zhu et al., 2010), in combination with SMER28, further increased the induction efficiency of HADFs (FIG. 9A-9B).

Figure 9C:
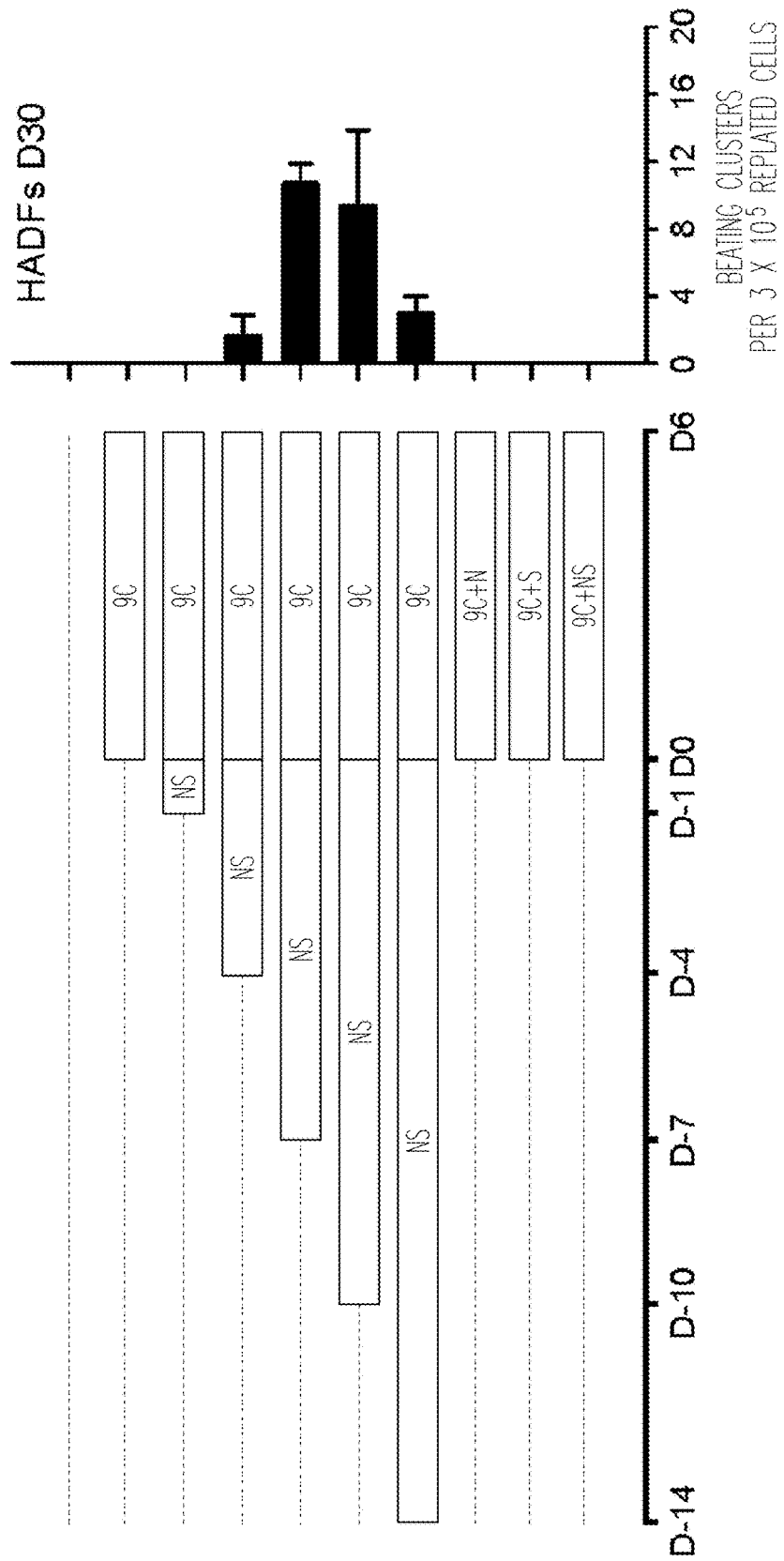
Figure 9D:
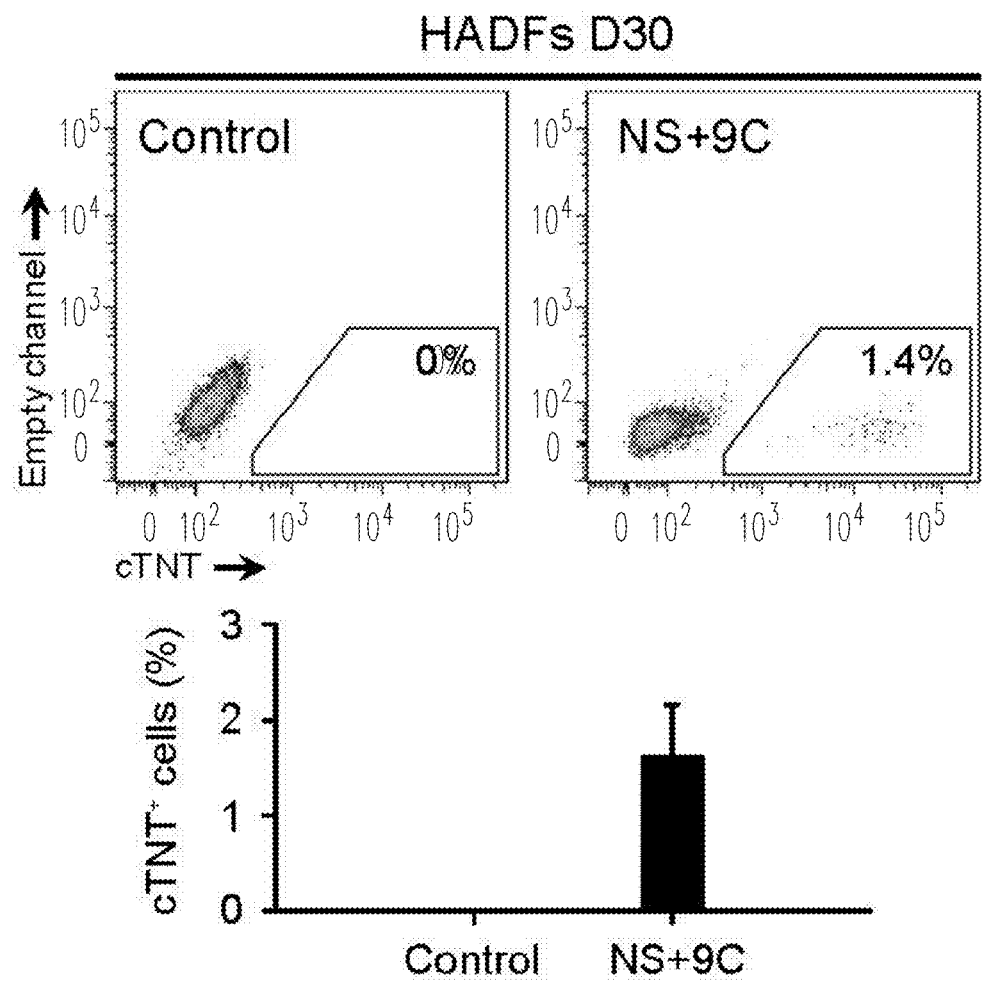
Figure 9E:
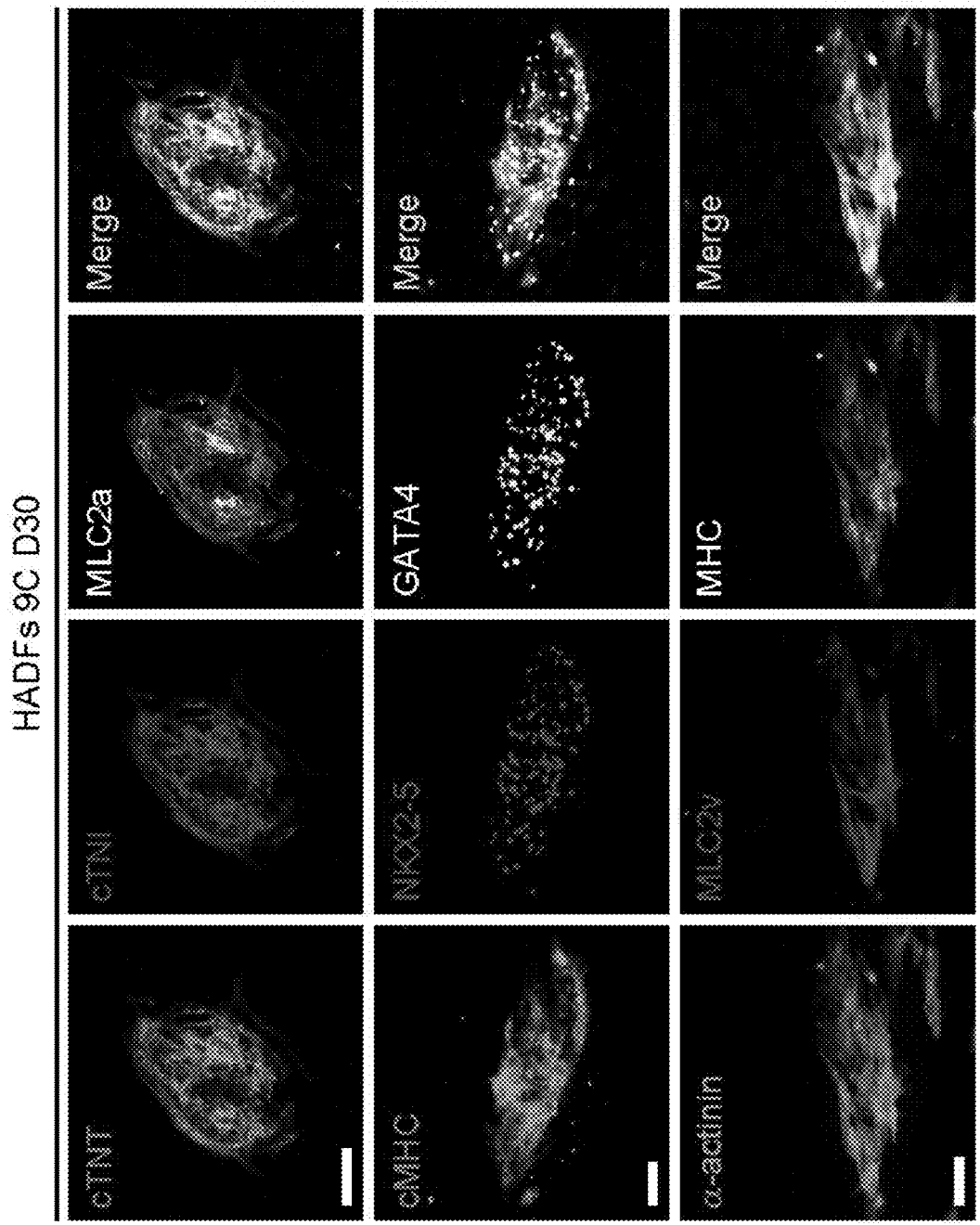
Figure 10A:
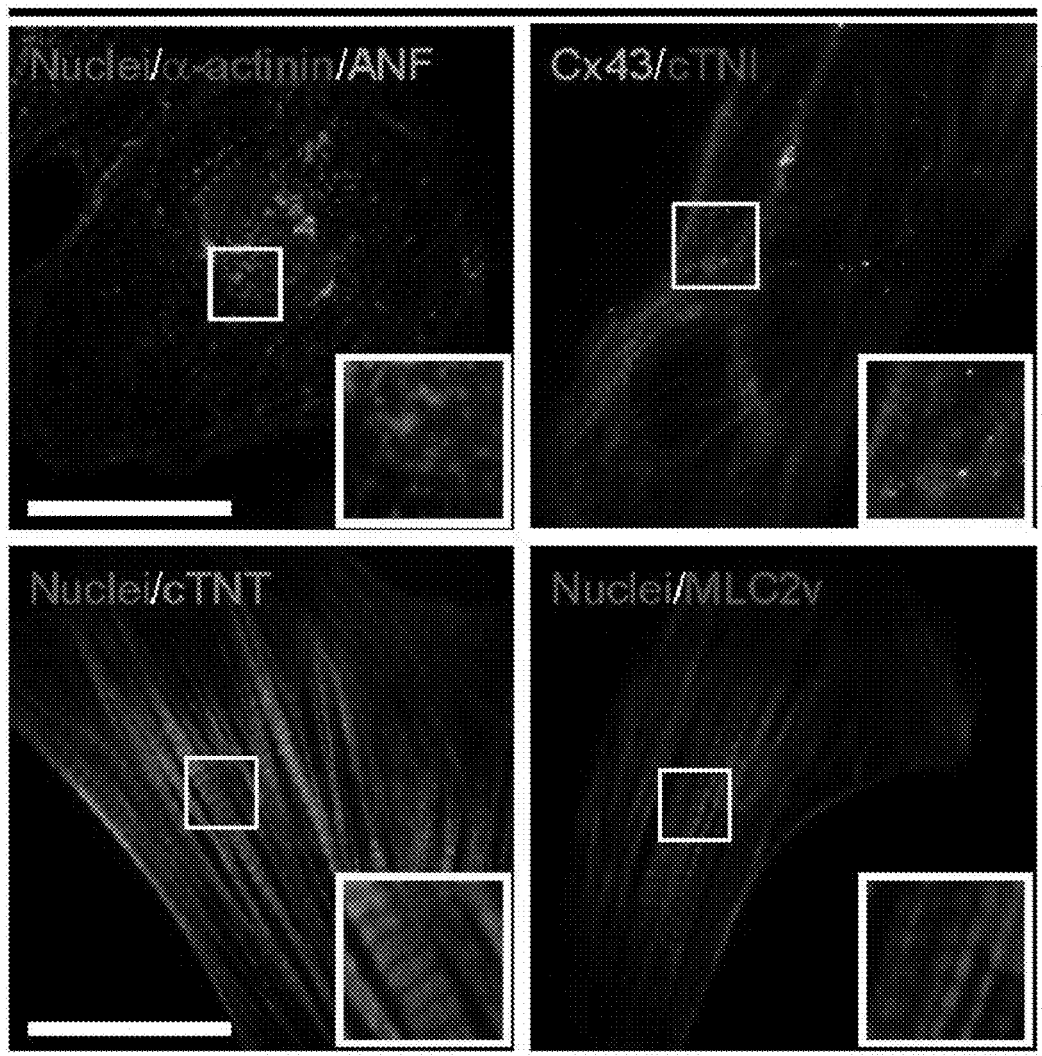
Figure 10B:
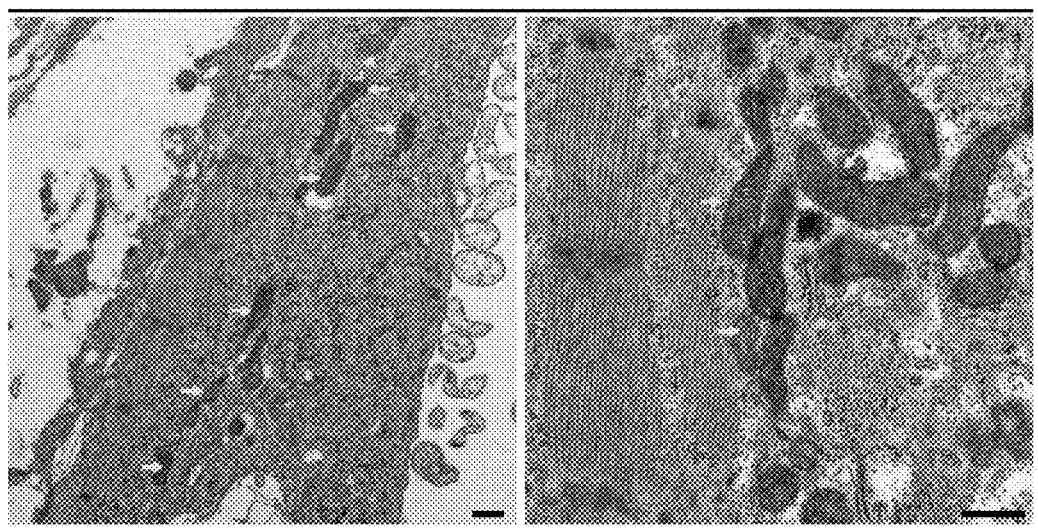
FIG. 10B shows electron microscopic images of HADF-CMs demonstrating detection of myofibrils (blue arrow) with Z-bands (red arrows) and mitochondria (yellow arrows). Scale bars, 500 nm.
Figure 10C:
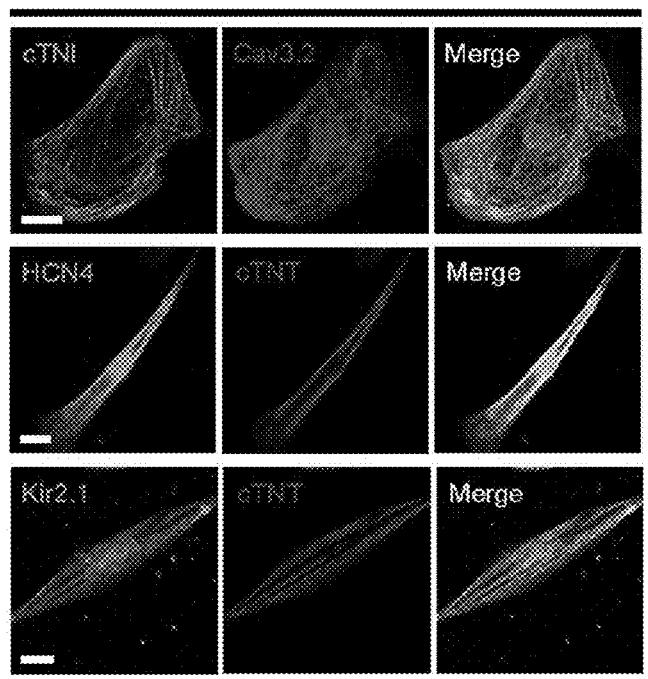
FIG. 10C illustrates expression of cardiac myofilament proteins including cTNI and cTNT, and cardiac ion channels including Cav3.2, HCN4, and Kir2.1 on HADF-CMs, as detected by immunofluorescence staining. Scale bars, 25 μm.
Figure 10D:
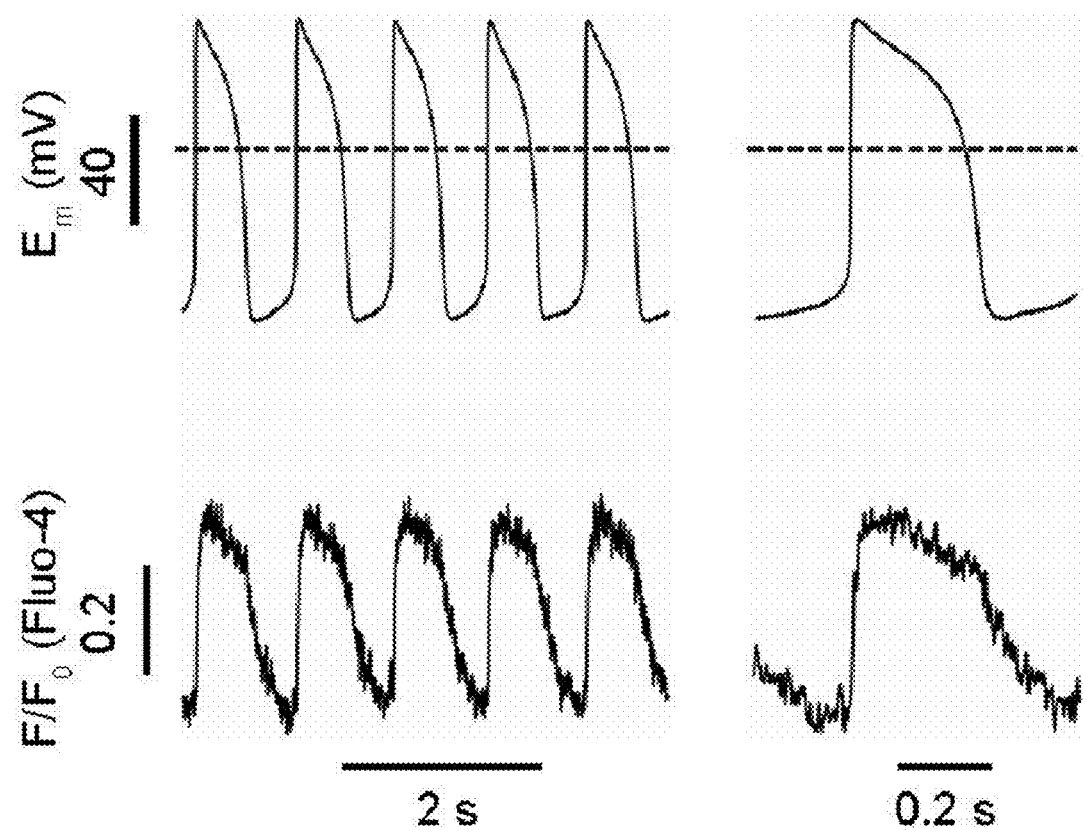
FIG. 10D shows representative traces of synchronized action potentials (APs) (upper panel) and $Ca^{2+}$ transients (lower panel) in HADF-CMs. Em, membrane potential. Dotted lines indicate 0 mV. F/F0, fluorescence relative to the baseline.
Figure 10F:
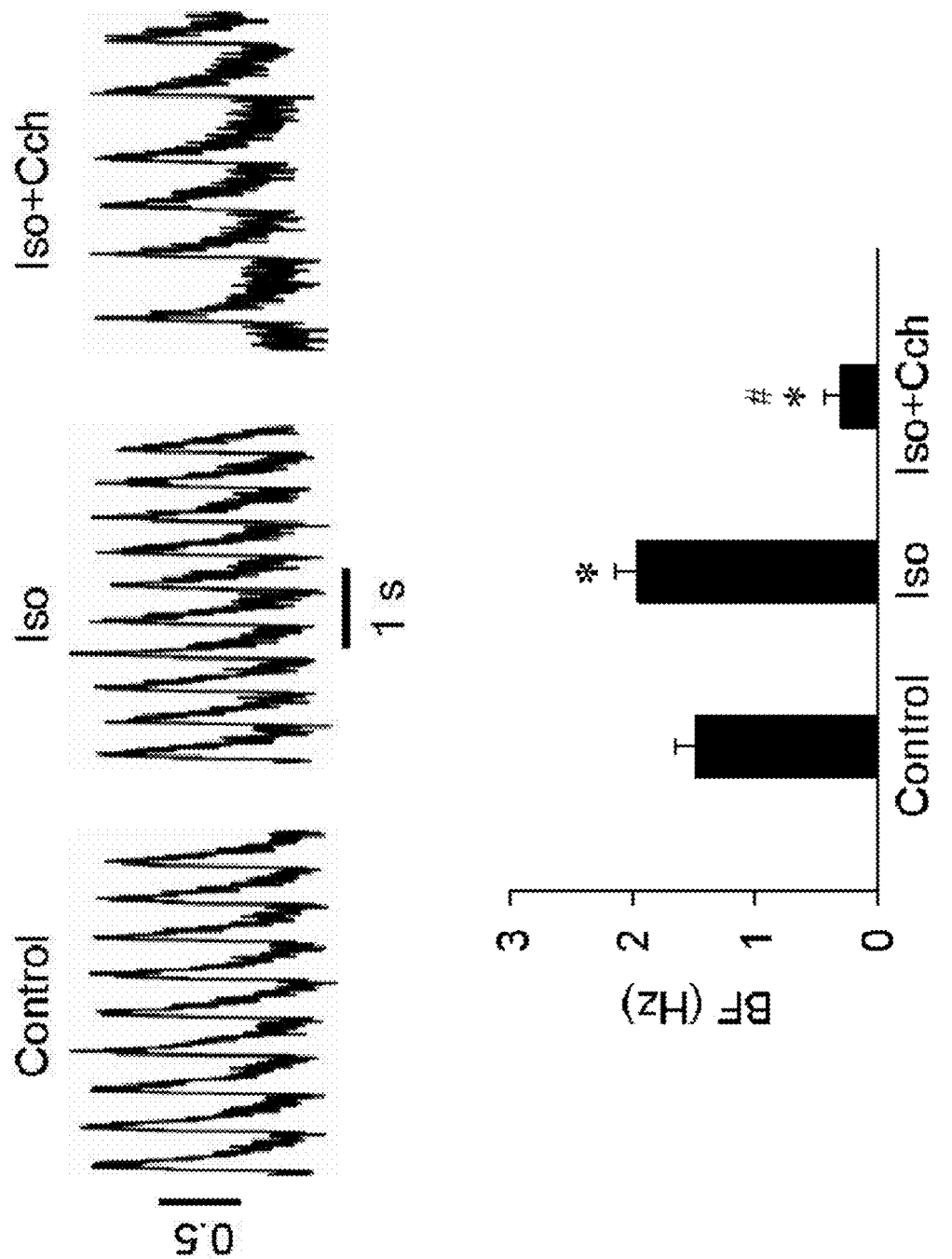
FIG. 10F illustrates the effects of isoproterenol (Iso) and carbachol (Cch) on beating rates in HADF-CMs (n=12). *P<0.05 vs. control. #P<0.05 vs. Iso.

Further characterization confirmed that pre-treatment of HADFs with the combination of NaB and SMER28 (NS) for 7 days, followed by the reprogramming conditions resulted in effective cardiac reprogramming of HADFs (FIG. 9C), albeit with lower efficiency than in human foreskin fibroblasts (HFFs) and human fetal lung fibroblasts (HLFs) (FIG. 9B-9D). Similar to the chemically induced HFF-cardiomyocytes and HLF-cardiomyocytes, chemically induced cardiomyocytes from HADFs (HADF-CMs) expressed a broad panel of cardiac proteins (FIG. 9E), displayed well-assembled sarcomeric structures (FIGS. 10A and 10B), expressed cardiac ion channels (FIG. 10C), and exhibited electrophysiological features similar to human pluripotent stem cell generated cardiomyocytes (hPSC-CMs; FIG. 10D-F). In addition, 80% ventricular-like action potentials were detected in HADF-CMs, similar to hPSC-CMs (85%) and chemically induced cardiomyocytes generated from fetal and neonatal fibroblasts. A major shift in expression from fibroblast genes to cardiomyocyte-specific genes, similar to hPSC-CMs, was also observed (FIG. 10G1-10G2). These findings demonstrate that chemically induced cardiomyocytes can also be generated from HADFs.

REFERENCES

Azad, G. K., Singh, V., Golla, U., and Tomar, R. S. (2013). Depletion of cellular iron by curcumin leads to alteration in histone acetylation and degradation of Sm11p in *Saccharomyces cerevisiae*. PLoS. One. 8, e59003.

Badal, S., Her, Y. F., and Maher, L. J., III (2015). Nonantibiotic Effects of Fluoroquinolones in Mammalian Cells. J. Biol. Chem. 290, 22287-22297.

Klose, R. J., Kallin, E. M., and Zhang, Y. (2006). JmjC-domain-containing proteins and histone demethylation. Nat. Rev. Genet. 7, 715-727.

Mosammaparast, N. and Shi, Y. (2010). Reversal of histone methylation: biochemical and molecular mechanisms of histone demethylases. Annu. Rev. Biochem. 79, 155-179.

Nam, Y. J., Song, K., Luo, X., Daniel, E., Lambeth, K., West, K., Hill, J. A., DiMaio, J. M., Baker, L. A., Bassel-Duby, R., and Olson, E. N. (2013). Reprogramming of human fibroblasts toward a cardiac fate. Proc. Natl. Acad. Sci. U.S.A 110, 5588-5593.

Pogribny, I. P., Tryndyak, V. P., Pogribna, M., Shpyleva, S., Surratt, G., Gamboa da, C. G., and Beland, F. A. (2013). Modulation of intracellular iron metabolism by iron chelation affects chromatin remodeling proteins and corresponding epigenetic modifications in breast cancer cells and increases their sensitivity to chemotherapeutic agents. Int. J. Oncol. 42, 1822-1832.

Sarkar, S., Perlstein, E. O., Imarisio, S., Pineau, S., Cordenier, A., Maglathlin, R. L., Webster, J. A., Lewis, T. A., O'Kane, C. J., Schreiber, S. L., and Rubinsztein, D. C. (2007). Small molecules enhance autophagy and reduce toxicity in Huntington's disease models. Nat. Chem. Biol. 3, 331-338.

Sayegh, J., Cao, J., Zou, M. R., Morales, A., Blair, L. P., Norcia, M., Hoyer, D., Tackett, A. J., Merkel, J. S., and Yan, Q. (2013). Identification of small molecule inhibitors of Jumonji AT-rich interactive domain 1B (JARID1B) histone demethylase by a sensitive high throughput screen. J. Biol. Chem. 288, 9408-9417.

Takahashi, K., Tanabe, K., Ohnuki, M., Narita, M., Ichisaka, T., Tomoda, K., and Yamanaka, S. (2007). Induction of pluripotent stem cells from adult human fibroblasts by defined factors. Cell 131, 861-872.

Zhu, S., Li, W., Zhou, H., Wei, W., Ambasudhan, R., Lin, T., Kim, J., Zhang, K., and Ding, S. (2010). Reprogramming of human primary somatic cells by OCT4 and chemical compounds. Cell Stem Cell 7, 651-655.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The following statements are intended to describe and summarize various embodiments of the invention according to the foregoing description in the specification.

Statements:

1. A composition comprising one or more of the following agents: a WNT agonist, a GSK3 inhibitor, a TGF-beta inhibitor, an inhibitor of extracellular signal-regulated kinase 1 (ERK1), an inhibitor of Ras GTPase-activating protein (Ras-GAP), an Oct-4 activator, a Rho-associated coiled coil forming protein serine/threonine kinase inhibitor, an iron chelator, a KDM5B inhibitor, a histone methyltransferase inhibitor, a PDGF tyrosine kinase inhibitor, or any combination thereof.

2. The composition of statement 1, containing at least two of the agents, or at least three of the agents, or at least four of the agents, or at least five of the agents, or at least six of the agents, or at least seven of the agents, or at least eight of the agents.

3. The composition of statements 1 or 2, wherein the WNT agonist is an agent that activates TCF/LEF-mediated transcription in a cell.

4. The composition of any of statements 1-3, wherein the WNT agonist binds and activates a Frizzled receptor family member.

5. The composition of any of statements 1-4, wherein the WNT agonist is one or more of a WNT family protein, an inhibitor of intracellular beta-catenin degradation, an activator of TCF/LEF, an inhibitor of GSK-3, or a combination thereof.
6. The composition of any of statements 1-5, wherein the WNT agonist is one or more of WNT-3a, a GSK-inhibitor, WNT5, WNT-6a, Norrin, or another WNT family protein.
7. The composition of any of statements 1-6, wherein the GSK3 inhibitor is one or more of CHIR99021 (6-(2-(4-(2,4-dichlorophenyl)-5-(4-methyl-1H-imidazol-2-yl)pyrimidin-2-ylamino)ethylamino)nicotinonitrile); 1-azakenpaullone (9-Bromo-7,12-dihydro-pyrido[3',2':2,3]azepino[4,5-b]indol-6(5H)-one), BIO ((2'Z,3'E)-6-Bromoindirubin-3'-oxime); AR-A014418 (N-(4-Methoxybenzyl)-N'-(5-nitro-1,3-thiazol-2-yl)urea); Indirubin-3'-monoxime; 5-Iodo-indirubin-3'-monoxime; kenpaullone (9-Bromo-7,12-dihydroindolo-[3,2-d][1]benzazepin-6(5H)-one); SB-415286 (3-[(3-Chloro-4-hydroxyphenyl)amino]-4-(2-nitro-phenyl)-1H-pyrrole-2,5-dione); SB-216763 (3-(2,4-Dichlorophenyl)-4-(1-methyl-1H-indol-3-yl)-1H-pyrrole-2,5-dione); Maybridge SEW00923SC (2-anilino-5-phenyl-1,3,4-oxadiazole); (Z)-5-(2,3-Methylenedioxyphenyl)-imidazolidine-2,4-dione; TWS119 (3-(6-(3-aminophenyl)-7H-pyrrolo[2,3-d]pyrimidin-4-yloxy)phenol); CHIR98014 (N2-(2-(4-(2,4-dichlorophenyl)-5-(1H-imidazol-1-yl)pyrimidin-2-ylamino)ethyl)-5-nitropyridine-2,6-diamine); SB415286 (3-(3-chloro-4-hydroxyphenylamino)-4-(2-nitrophenyl)-1H-pyrrole-2,5-dione); Tideglusib (2-(1-naphthalenyl)-4-(phenylmethyl)); LY2090314 (3-imidazo[1,2-a]pyridin-3-yl-4-[1,2,3,4-tetrahydro-2-(1-piperidinylcarbonyl)-pyrrolo[3,2,1-jk][1,4] benzodiazepin-7-yl]); lithium salt; or any combination thereof
8. The composition of any of statements 1-7, wherein the GSK3 inhibitor is one or more of CHIR99021, SB216763, TWS119. CHIR98014, Tideglusib (NP031112, NP-12), SB415286, LY2090314, or any combination thereof.
9. The composition of any of statements 1-8, wherein the GSK3 inhibitor is CHIR99021.
10. The composition of any of statements 1-9, wherein the TGFβ inhibitor is one or more of 4-[4-(1,3-benzodioxol-5-yl)-5-(2-pyridinyl)-1H-imidazol-2-yl]benzamide (SB 431542); 3-(6-Methyl-2-pyridinyl)-N-phenyl-4-(4-quinolinyl)-1H-pyrazole-1-carbothioamide (A83-01); 2-(3-(6-Methylpyridine-2-yl)-1H-pyrazol-4-yl)-1,5-naphthyridine (SJN 2511); 4-[4-(2,3-Dihydro-1,4-benzodioxin-6-yl)-5-(2-pyridinyl)-1H-imidazol-2-yl]benzamide (D 4476); 4-[3-(2-Pyridinyl)-1H-pyrazol-4-yl]-quinoline (LY 364947); 2-(4-(benzo[d][1,3]dioxol-5-yl)-2-tert-butyl-1H-imidazol-5-yl)-6-methylpyridine (SB505124); 6-[2-(1,1-Dimethylethyl)-5-(6-methyl-2-pyridinyl)-1H-imidazol-4-yl]quinoxaline (SB 525334); 2-(5-Chloro-2-fluorophenyl)-4-[(4-pyridyl)amino]pteridine (SD 208); 4-(6-(4-(piperazin-1-yl)phenyl)pyrazolo[1,5-a]pyrimidin-3-yl)quinoline, or any combination thereof.
11. The composition of any of statements 1-10, wherein the TGFβ inhibitor is A83-01.
12. The composition of any of statements 1-11, wherein the ERK1 and/or Ras-GAP inhibitor is one or more of SC1; Chromone; PD 98059; PD0325901; Selumetinib; ARRY-438162; PD198306; PD0325901; AZD8330; PD 184352; PD 184161; SL 327; 1,4-Diamino-2,3-dicyano-1,4-bis(2-aminophenylthio)butadiene; U0126; GW 5074; BAY 43-9006; Ro 09-2210; FR 180204; PKI-ERK-005; CAY10561; GSK 120212; RDEA119; XL518; ARRY-704; or any combination thereof.
13. The composition of any of statements 1-12, wherein the ERK1 and Ras-GAP inhibitor is SC1.
14. The composition of any of statements 1-13, wherein the OCT4 activator is OAC2, shown below:

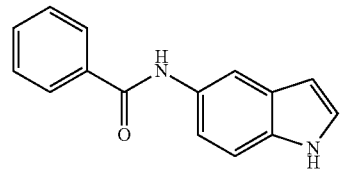 [SMILES: O=C(Nc1ccc2[nH]ccc2c1)c1ccccc1]

15. The composition of any of statements 1-14, wherein the Rho-associated coiled coil forming protein serine/threonine kinase inhibitor is one or more of Y27632 (4-[(1R)-1-aminoethyl]-N-pyridin-4-ylcyclohexane-1-carboxamide); 4-(2-pyridylcarbamoyl)piperidine; 1-benzyloxycarbonyl-4-(4-pyridylcarbamoyl)-piperidine; 1-benzoyl-4-(4-pyridylcarbamoyl)piperidine; 1-propyl-4-(4-pyridylcarbamoyl)piperidine; 1-[3-(2-(2-thienylmethyl)phenoxy)-2-hydroxypropyl]-4-(4-pyridylcarbamoyl)piperidine; 4-(4-pyridylcarbamoyl)piperidine; 1-benzyl-4-(4-pyridylcarbamoyl)-1,2,5,6-tetrahydropyridine; 3-(4-pyridylcarbamoyl)piperidine; 1-benzyl-3-(4-pyridylcarbamoyl)piperidine; 1-(2-(4-benzyloxyphenoxy)ethyl)-4-(N-(2-pyridyl)-N-benzylcarbamoyl)piperidine; 1-formyl-4-(4-pyridylcarbamoyl)piperidine; 4-(3-pyridylcarbamoyl)piperidine; 1-isopropyl-4-(4-pyridylcarbamoyl)piperidine; 1-methyl-4-(4-pyridylcarbamoyl)piperidine; 1-hexyl-4-(4-pyridylcarbamoyl)piperidine; 1-benzyl-4-(4-pyridylcarbamoyl)piperidine; 1-(2-phenylethyl)-4-(4-pyridylcarbamoyl)piperidine; 1-(2-(4-methoxyphenyl) ethyl)-4-(4-pyridylcarbamoyl)-piperidine; 1-(2-(4-methoxyphenyl)ethyl)-4-(2-pyridylcarbamoyl)-piperidine; 1-(2-(4-chlorophenyl)ethyl)-4-(4-pyridylcarbamoyl)-piperidine; 1-diphenylmethyl-4-(2-pyridylcarbamoyl)piperidine; 1-[2-(4-(5-methyl-3-oxo-2,3,4,5-tetrahydropyridazin-6-yl)phenyl)ethyl]-4-(2-pyridylcarbamoyl)piperidine; 1-(4-(4,5-dihydro-2-furyl)phenyl)-4-(4-pyridylcarbamoyl)piperidine; 1-(2-nitrophenyl)-4-(4-pyridylcarbamoyl)piperidine; 1-(2-aminophenyl)-4-(4-pyridylcarbamoyl)piperidine; 1-nicotinoyl-4-(4-pyridylcarbamoyl)piperidine; 1-isonicotinoyl-4-(4-pyridylcarbamoyl)piperidine; 1-(3,4,5-trimethoxybenzoyl)-4-(4-pyridylcarbamoyl)-piperidine; 1-acetyl-4-(4-pyridylcarbamoyl)piperidine; 1-(3-(4-fluorobenzoyl)propyl)-4-(4-pyridylcarbamoyl)-piperidine; 1-(3-(4-fluorobenzoyl)propyl)-4-(2-pyridylcarbamoyl)-piperidine; 1-(1-(4-hydroxybenzoyl)ethyl)-4-(2-pyridylcarbamoyl)-piperidine; 1-(1-(4-benzyloxybenzoyl)ethyl)-4-(2-pyridylcarbamoyl)-piperidine; 1-(2-(4-hydroxyphenoxy)ethyl)-4-(2-pyridylcarbamoyl)-piperidine; 1-(4-(4-fluorophenyl)-4-hydroxybutyl)-4-(4-pyridylcarbamoyl)piperidine; 1-(1-methyl-2-(4-hydroxyphenyl)-2-hydroxyethyl)-4-(2-pyridylcarbamoyl)piperidine; 1-cinnamyl-4-(2-pyridylcarbamoyl)piperidine; 1-(2-hydroxy-3-phenoxypropyl)-4-(2-pyridylcarbamoyl)-piperidine; 1-(2-hydroxy-3-phenoxypropyl)-4-(3-pyridylcarbamoyl)- piperidine; 1-(2-hydroxy-3-phenoxypropyl)-4-(2-pyridylcarbamoyl)-piperidine; 1-(2-phenylethyl)-4-[N-(2-pyridyl)-N-(2-(N,N-dimethylamino)ethyl) carbamoyl]piperidine; 1-benzyloxycarbonyl-4-(2-pyridylcarbamoyl)piperidine; 1-(3-chlorophenyl) carbamoyl-4-(4-pyridylcarbamoyl)-piperidine; 4-[N-(2-pyridyl)-N-(2-(N,N-dimethylamino)ethyl)-carbamoyl]-piperidine; 1-methyl-4-(4-pyridylcarbamoyl)-1,2,5,6-tetrahydropyridine; 1-nicotinoyl-3-(4-pyridylcarbamoyl)piperidine; 1-[2-(4-fluorobenzoyl)ethyl]-4-(4-pyridylcarbamoyl)-piperidine; 1-(6-chloro-2-methylimidazo[1,2-a]pyridine-3-carbonyl)-4-(4-pyridylcarbamoyl)piperidine; 1-(4-nitrobenzyl)-4-(4-pyridylcarbamoyl)piperidine; 1-hexyl-4-(4-pyridylcarbamoyl)piperidine; 1-benzyloxycarbonyl-4-(2-chloro-4-pyridylcarbamoyl)-piperidine; 4-(2-chloro-4-pyridylcarbamoyl)piperidine; 1-(2-chloronicotinoyl)-4-(4-pyridylcarbamoyl)piperidine; 3-(2-chloro-4-pyridylcarbamoyl)piperidine; 1-(4-phthalimidobutyl)-4-(4-pyridylcarbamoyl)piperidine; 1-(3,5-di-tert-butyl-4-hydroxycinnamoyl)-4-(4-pyridylcarbamoyl)piperidine; 1-carbamoylmethyl-4-(4-pyridylcarbamoyl)piperidine; 1-benzyloxycarbonyl-4-(5-nitro-2-pyridylcarbamoyl)-piperidine; 4-(5-nitro-2-pyridylcarbamoyl)piperidine; trans-4-benzyloxycarboxamidomethyl-1-(4-pyridylcarbamoyl) cyclohexane; trans-4-aminomethyl-1-(4-pyridylcarbamoyl)cyclohexane; trans-4-formamidomethyl-1-(4-pyridylcarbamoyty-cyclohexane; trans-4-dimethylaminomethyl-1-(4-pyridylcarbamoyl)-cyclohexane; N-benzylidene-trans-(4-pyridylcarbamoyl)-cyclohexylmethylamine; trans-4-benzylaminomethyl-1-(4-pyridylcarbamoyl)-cyclohexane; trans-4-isopropylaminomethyl-1-(4-pyridylcarbamoyl)-cyclohexane; trans-4-nicotinoylaminomethyl-1-(4-pyridylcarbamoyl)-cyclohexane; trans-4-cyclohexylaminomethyl-1-(4-pyridylcarbamoyl)-cyclohexane; trans-4-benzyloxycarboxamide-1-(4-pyridylcarbamoyl)-cyclohexane; trans-4-amino-1-(4-pyridylcarbamoyl) cyclohexane; trans-4-(1-aminoethyl)-1-(4-pyridylcarbamoyl)-cyclohexane; trans-4-aminomethyl-cis-2-methyl-1-(4-pyridylcarbamoyl)-cyclohexane; (+)-trans-4-(1-benzyloxycarboxamidopropyl)-1-cyclohexanecarboxylic acid; (+)-trans-4-(1-benzyloxycarboxamidopropyl)-1-(4-pyridylcarbamoyl)cyclohexane; (−)-trans-4-Q-benzyloxycarboxamidopropyl)-1-(4-pyridylcarbamoyl)cyclohexane; (+)-trans-4-(1-aminopropyl)-1-(4-pyridylcarbamoyl)-cyclohexane; (−)-trans-4-(1-aminopropyl)-1-(4-pyridylcarbamoyl)-cyclohexane; (−)-trans-4-(1-benzyloxycarboxamidoethyl)-1-(4-pyridylcarbamoyl) cyclohexane; (+)-trans-4-(1-benzyloxycarboxamidoethyl)-1-(4-pyridylcarbamoyl) cyclohexane; (+)-trans-4-(1-aminoethyl)-1-(4-pyridylcarbamoyl)-cyclohexane; (−)-trans-4-(1-aminoethyl)-1-(4-pyridylcarbamoyl)-cyclohexane; trans-4-(4-chlorobenzoyl)aminomethyl-1-(4-pyridylcarbamoyl)cyclohexane; trans-4-aminomethyl-1-(2-pyridylcarbamoyl)cyclohexane; trans-4-benzyloxycarboxamidomethyl-1-(2-pyridylcarbamoyl)cyclohexane, trans-4-methylaminomethyl-1-(4-pyridylcarbamoyl)-cyclohexane; trans-4-(N-benzyl-N-methylamino) methyl-1-(4-pyridylcarbamoyl)cyclohexane; trans-4-aminomethyl-1-(3-pyridylcarbamoyl)cyclohexane; trans-4-aminomethyl-1-[(3-hydroxy-2-pyridyl)carbamoyl]-cyclohexane; trans-4-benzyloxycarboxamidomethyl-1-(3-pyridylcarbamoytycyclohexane; trans-4-benzyloxycarboxamidomethyl-1-[(3-benzyloxy-2-pyridyl)carbamoyl]cyclohexane; trans-4-phthalimidomethyl-1-(4-pyridylcarbamoyl)-cyclohexane; trans-4-benzyloxycarboxamidomethyl-1-(3-methyl-4-pyridylcarbamoyl)cyclohexane; trans-4-aminomethyl-1-(3-methyl-4-pyridyl carbamoyl)-cyclohexane; 4-(trans-4-benzyloxycarboxamidomethylcyclohexyl-carbonyl) amino-2,6-dimethylpyridine-N-oxide; 4-(trans-4-aminomethylcyclohexylcarbonyl)amino-2,6-dimethylpyridine-N-oxide; trans-4-aminomethyl-1-(2-methyl-4-pyridylcarbamoyl)-cyclohexane; trans-4-(1-benzyloxycarboxamidoethyl)-1-(4-pyridylcarbamoyl) cyclohexane; trans-4-(1-amino-1-methylethyl)-1-(4-pyridylcarbamoyl)-cyclohexane; trans-4-(2-aminoethyl)-1-(4-pyridylcarbamoyl)cyclohexane; trans-4-(2-amino-1-methylethyl)-1-(4-pyridylcarbamoyl)-cyclohexane; trans-4-(1-aminopropyl)-1-(4-pyridylcarbamoyl)-cyclohexane; trans-4-aminomethyl-trans-1-methyl-1-(4-pyridylcarbamoyl)cyclohexane; trans-4-benzylaminomethyl-cis-2-methyl-1-(4-pyridyl-carbamoyl)cyclohexane; trans-4-(1-benzyloxycarboxamide-1-methylethyl)-1-(4-pyridylcarbamoyl)cyclohexane; trans-4-benzyloxycarboxamidomethyl-1-(N-methyl-4-pyridylcarbamoyl)cyclohexane; trans-4-(1-acetamide-1-methylethyl)-1-(4-pyridylcarbamoyl) cyclohexane; trans-N-(6-amino-4-pyrimidyl)-4-aminomethylcyclohexanecarboxamide; trans-N-(1H-pyrrolo[2,3-b]pyridin-4-yl)-4-aminomethylcyclohexane-carboxamide; (+)-trans-N-(1H-pyrrolo[2,3-b]pyridin-4-yl)-4-(1-aminoethylcyclo-hexanecarboxamide; trans-N-(1H-pyrrolo[2,3-b]pyridin-4-yl)-4-(1-amino-1-methylethyl)cyclo-hexanecarboxamide; trans-N-(1H-pyrazolo[3,4-b]pyridin-4-yl)-4-aminomethylcyclohexane-carboxamide; (+)-trans-N-(1H-pyrazolo[3,4-b]pyridin-4-yl)-4-(1-aminoethyl) cyclo-hexanecarboxamide; trans-N-(1H-pyrazolo[3,4-b]pyridin-4-yl)-4-(1-amino-1-methylethyl)cyclo-hexanecarboxamide; (+)-trans-N-(2-amino-4-pyridyl)-4-(1-aminoethyl)-cyclohexanecarboxamide trans-N-(1H-pyrazolo[3,4-d]pyrimidin-4-yl)-4-aminomethylcyclohexane-carboxamide; (+)-trans-N-(1H-pyrazolo[3,4-d]pyrimidin-4-yl)-4-(1-aminoethyl) cyclohexane carboxamide; trans-N-(1H-pyrazolo[3,4-d]pyrimidin-4-yl)-4-(1-amino-1-methylethyl) cyclohexane carboxamide; trans-N-(4-pyrimidinyl)-4-aminomethylcyclohexanecarboxamide; trans-N-(3-amino-4-pyridyl)-4-aminomethylcyclohexanecarboxamide; trans-N-(7H-imidazo[4,5-d]pyrimidin-(6-yl)-4-aminomethylcyclo-hexanecarboxamide; trans-N-(3H-1,2,3-triazolo[4,5-d]-pyrimidin-7-yl)-4-aminomethyl-cyclohexane carboxamide; trans-N-(1-benzyl-1H-pyrazolo[3,4-b]pyridin-4-yl)-4-aminomethylcyclohexane; carboxamide trans-N-(1H-5-pyrazolyl)-4-aminomethylcyclohexanecarboxamide; trans-N-(1H-pyrazolo[3,4-b]pyridin-4-yl)-4-aminomethylcyclo-hexanecarboxamide; trans-N-(4-pyridazinyl)-4-aminomethylcyclohexanecarboxamide; trans-N-(7H-pyrrolo[2,3-d]pyrimidin-4-yl)-4-aminomethylcyclo-hexanecarboxamide; trans-N-(2-amino-1-pyridyl)-4-aminomethylcyclohexanecarboxamide; trans-N-(thieno[2,3-d]pyrimidin-4-yl)-4-aminomethylcyclohexanecarboxamide; trans-N-(5-methyl-1,2,4-triazolo[1,5-a]pyrimidin-7-yl)-4-aminomethyl-cyclohexane carboxamide; trans-N-(3- cyano-5-methylpyrazolo[1,5-a]pyrimidin-7-yl)-4-aminomethyl-cyclohexanecarboxamide; trans-N-(1H-pyrazolo[3,4-b]pyridin-4-yl)-4-(1-amino-1-methylethyl)cyclohexanecarboxamide; trans-N-(2-(1-pyrrolidinyl)-4-pyridyl)-4-aminomethylcyclohexane-carboxamide; trans-N-(2,6-diamino-4-pyrimidyl)-4-aminomethylcyclohexanecarboxamide; (+)-trans-N-(7-methyl-1,8-naphthyridin-4-yl)-4-(1-aminoethyl)cyclohexanecarboxamide; trans-N-(1-benzyloxymethylpyrrolo[2,3-b]pyridin-4-yl)-4-aminomethyl-cyclohexanecarboxamide; (+)-trans-N-(1-methylpyrrolo[2,3-b]pyridin-4-yl)-4-(1-aminoethyl)cyclo-hexanecarboxamide; trans-N-benzyl-N-(2-benzylamino-4-pyridyl)-4-(1-amino-1-methylethyl)-cyclohexanecarboxamide; trans-N-(2-azide-4-pyridyl)-4-aminomethylcyclohexanecarboxamide; trans-N-(2,3-dihydro-1H-pyrrolo[2,3-b]pyridin-4-yl)-4-aminomethyl-cyclohexanecarboxamide; trans-N-(2,3-dihydro-1H-pyrrolo[2,3-b]pyridin-4-yl)-4-(1-amino-1-methylethyl)cyclohexanecarboxamide; trans-N-(2-carboxy-4-pyridyl)-4-aminomethylcyclohexanecarboxamide; (R)-(+)-trans-N-(3-bromo-1H-pyrrolo[2,3-b]pyridin-4-yl)-4-(1-aminoethyl)cyclohexanecarboxamide; trans-N-(1H-pyrrolo[2,3-b]pyridin-4-yl)-4-guanidinomethylcyclohexanecarboxamide; trans-N-(1H-pyrazolo[3,4-b]pyridin-4-yl)-4-guanidinomethyl-cyclohexanecarboxamide; trans-N-(4-pyridyl)-4-guanidinomethylcyclohexanecarboxamide; trans-N-(1-methylpyrrolo[2,3-b]pyridin-4-yl)-4-(guanidinomethyl)cyclo-hexanecarboxamide, trans-N-(1H-pyrrolo[2,3-b]pyridin-4-yl)-4-(2-imidazolin-2-yl)aminomethyl-cyclohexanecarboxamide trans-N-(1-benzyloxymethylpyrrolo[2,3-b]pyridin-4-yl)-4-guanidinomethyl-cyclohexanecarboxamide; trans-N-(2-amino-4-pyridyl)-4-guanidinomethylcyclohexanecarboxamide; trans-N-(1-benzyloxymethyl-1H-pyrrolo[2,3-b]pyridin-4-yl)-4-(2-imidazolin-2-yl)aminomethylcyclohexanecarboxamide; trans-N-(1H-pyrrolo[2,3-b]pyridin-4-yl)-4-(3-benzylguanidinomethyl)cyclo-hexanecarboxamide; trans-N-(1H-pyrrolo[2,3-b]pyridin-4-yl)-4-(3-phenylguanidinomethyl)-cyclohexanecarboxamide; trans-N-(1H-pyrrolo[2,3-b]pyridin-4-yl)-4-(3-propylguanidinomethyl)-cyclohexanecarboxamide; trans-N-(1H-pyrrolo[2,3-b]pyridin-4-yl)-4-(3-octylguanidinomethyl)-cyclohexanecarboxamide; trans-N-(1-benzyloxymethylpyrrolo[2,3-b]pyridin-4-yl)-4-(2-benzyl-3-ethylguanidinomethyl)-cyclohexanecarboxamide; trans-N-(1H-pyrrolo[2,3-b]pyridin-4-yl)-4-(imidazol-2-yl)aminomethyl-cyclohexanecarboxamide; trans-N-(1H-pyrrolo[2,3-b]pyridin-4-yl)-4-(thiazol-2-yl)aminomethyl-cyclohexane carboxamide, (R)-(+)-N-(4-pyridyl)-4-(1-aminoethyl)benzamide; N-(4-pyridyl)-4-(1-amino-1-methylethyl)benzamide; N-(4-pyridyl)-4-aminomethyl-2-benzyloxybenzamide; N-(4-pyridyl)-4-aminomethyl-2-nitrobenzamide; (R)-(−)-N-(4-pyridyl)-3-amino-4-(1-aminoethyl)benzamide; (R)-(+)-N-(4-pyridyl)-4-(1-aminoethyl)-3-chlorobenzamide; N-(4-pyridyl)-3-aminobenzamide; (R)-(+)-N-(1H-pyrrolo[2,3-b]pyridin-4-yl)-4-(1-aminoethyl)benzamide; (R)-(+)-N-(1H-pyrazolo[3,4-b]pyridin-4-yl)-4-(1-aminoethyl)benzamide; N-(1H-pyrazolo[3,4-b]pyridin-4-yl)-4-guanidino-methylbenzamide; N-(4-pyridyl)-4-guanidinomethylbenzamide; (R)-(+)-N-(4-pyridyl)-4-(1-aminoethyl)-3-fluorobenzamide; N-(4-pyridyl)-4-aminomethylbenzamide; N-(4-pyridyl)-4-aminomethyl-2-hydroxybenzamide; N-(4-pyridyl)-4-(2-aminoethyl)benzamide; N-(4-pyridyl)-4-aminomethyl-3-nitrobenzamide; N-(4-pyridyl)-3amino-4-aminomethylbenzamide; (S)-(−)-N-(4-pyridyl)-4-(1-aminoethyl)benzamide, (S)-(−)-N-(4-pyridyl)-2-(1-aminoethyl)benzamide, (R)-(+)-N-(4-pyridyl)-4-(1-aminoethyl)-2-chlorobenzamide; (R)-(+)-N-(1H-pyrrolo[2,3-b]pyridin-4-yl)-4-(1-(3-propylguanidino)ethyl)-benzamide; (R)-(−)-N-(1H-pyrrolo[2,3-b]pyridin-4-yl)-4-(1-aminoethyl)-3-azide-benzamide; (R)-(+)-N-(4-pyridyl)-4-(1-aminoethyl)-2-nitrobenzamide; (R)-(−)-N-(4-pyridyl)-4-(1-aminoethyl)-3-ethoxybenzamide; (R)-(+)-N-(3-iodo-1H-pyrrolo[2,3-b]pyridin-4-yl)-4-(1-aminoethyl)benzamide; (R)-(+)-N-(3-iodo-1H-pyrrolo[2,3-b]pyridin-4-yl)-4-(1-aminoethyl)-3-azidebenzamide; (R)-(−)-N-(4-pyridyl)-4-(1-aminoethyl)-3-hydroxy-benzamide; N-(1H-pyrazolo[3,4-b]pyridin-4-yl)-4-guanidinomethyl-3-nitrobenzamide; (R)-N-(1H-pyrazolo[3,4-b]pyridin-4-yl)-4-(1-guanidinoethyl)-3-nitrobenzamide; (R)-N-(1H-pyrazolo[3,4-b]pyridin-4-yl)-4-(1-aminoethyl)-2-nitrobenzamide; N-(1H-pyrazolo[3,4-b]pyridin-4-yl)-4-guanidinobenzamide; (R)-N-(1H-pyrazolo[3,4-b]pyridin-4-yl)-4-(1-aminoethyl)-3-nitrobenzamide; (R)-N-(1H-pyrazolo[3,4-b]pyridin-4-yl)-4-(1-guanidinoethyl)benzamide; N-(1H-pyrazolo[3,4-b]pyridin-4-yl)-4-(1-amino-2-hydroxyethyl)benzamide; N-(1H-pyrazolo[3,4-b]pyridin-4-yl)-4-aminomethyl-3-nitrobenzamide; N-(1H-pyrrolo[2,3-b]pyridin-4-yl)-4-piperidinecarboxamide; N-(1H-pyrazolo[3,4-b]pyridin-4-yl)-4-piperidinecarboxamide. N-(1H-pyrazolo[3,4-b]pyridin-4-yl)-1-aminoacetyl-4-piperidine-carboxamide; N-(1-methoxymethyl-1H-pyrazolo[3,4-b]pyridin-4-yl)-4-piperidine-carboxamide; N-(2,3-dihydro-1H-pyrrolo[2,3-b]pyridin-4-yl)-4-piperidinecarboxamide; N-(1H-pyrrolo[2,3-b]pyridin-4-yl)-1-(2-phenylethyl)-4-piperidine-carboxamide N-(1H-pyrrolo[2,3-b]pyridin-4-yl)-1-amidino-4-piperidinecarboxamide; N-(1H-pyrrolo[2,3-b]pyridin-4-yl)-1-(3-phenylpropyl)-4-piperidine-carboxamide; N-(1H-pyrrolo[2,3-b]pyridin-4-yl)-1-benzyl-4-piperidinecarboxamide; N-(1H-pyrazolo[3,4-b]pyridin-4-yl)-1-(2-phenylethyl)-4-piperidine-carboxamide; N-(1H-pyrazolo[3,4-b]pyridin-4-yl)-1-(3-phenylpropyl)-4-piperidine-carboxamide; N-(1H-pyrrolo[2,3-b]pyridin-4-yl)-4-(1-amino-1-methylethyl)benzamide; or any combination thereof.

16. The composition of any of statements 1-15, wherein the Rho-associated coiled coil forming protein serine/threonine kinase inhibitor is Y27632 (4-[(1R)-1-aminoethyl]-N-pyridin-4-ylcyclohexane-1-carboxamide).

17. The composition of any of statements 1-16, wherein the histone methyltransferase inhibitor is one or more of Bix-O 1294; Chaetocin; 3-deazaneplanocin hydrochloride; UNC 0224; UNC 0638; UNC 0646; BRD4770; or combinations thereof.

18. The composition of any of statements 1-17, wherein the histone methyltransferase inhibitor is Bix-01294.

19. The composition of any of statements 1-18, wherein the iron chelator and/or KDM5B inhibitor is AS8351, PBIT, Omecamtiv mecarbil, or a combination thereof.

20. The composition of any of statements 1-19, wherein the iron chelator and/or KDM5B inhibitor is AS8351 or PBIT.
21. The composition of any of statements 1-20, wherein the platelet-derived growth factor receptor inhibitor is one or more of SU16f; AG18; DMPQ; PD 166285; SU 6668; Sunitinib maleate; or combinations thereof.
22. The composition of any of statements 1-21, wherein the platelet-derived growth factor receptor inhibitor is SU16f
23. The composition of any of statements 1-22, wherein the platelet-derived growth factor tyrosine kinase inhibitor is one or more of JNJ-10198409; AG-370; AG-1296; Imatinib mesylate; 3-(4-Isopropylbenzylidenyl)indolin-2-one; PKC-412; RG-13022; SU11652; Tyrphostin 9; Tyrphostin 46; Tyrphostin AG 1295; or any combination thereof.
24. A composition comprising one or more of the following agents: CHIR99021 (a GSK3 inhibitor and/or WNT agonist), A83-01 (a TGF-beta inhibitor), SC1 (an inhibitor of extracellular signal-regulated kinase 1 (ERK1) and an inhibitor of Ras GTPase-activating protein (Ras-GAP)), OAC2 (an Oct-4 activator), Y27632 (a Rho-associated coiled coil forming protein serine/threonine kinase inhibitor), BIX-01294 (a histone methyltransferase inhibitor), AS8351 or PBIT (iron chelator and/or KDM5B inhibitor), SU16f (a PDGF receptor inhibitor), JNJ-10198409 (a PDGF tyrosine kinase inhibitor), or any combination thereof.
25. A composition consisting essentially of a carrier and one or more of the following agents: CHIR99021 (a GSK3 inhibitor and/or a WNT agonist), A83-01 (a TGF-beta inhibitor). SC1 (an inhibitor of extracellular signal-regulated kinase 1 (ERK1) and an inhibitor of Ras GTPase-activating protein (Ras-GAP), OAC2 (an Oct-4 activator), Y27632 (a Rho-associated coiled coil forming protein serine/threonine kinase inhibitor), BIX-01294 (a histone methyltransferase inhibitor), AS8351 or PBIT (iron chelator and/or KDM5B inhibitor), SU16f (a PDGF receptor inhibitor), JNJ-10198409 (a PDGF tyrosine kinase inhibitor, or any combination thereof.
26. The composition of any of statements 1-25, wherein the composition is a cell reprogramming composition.
27. The composition of any of statements 1-26, wherein the agent(s) or compound(s) is present in an amount sufficient to reprogram a cell into a cardiac progenitor or cardiomyocyte cell type.
28. The composition of any of statements 1-27, wherein the agent(s) or compound(s) is present in an amount sufficient to induce a cell to express GATA4, ISL1 or a combination thereof.
29. The composition of any of statements 1-28, wherein the agent(s) or compound(s) is present in an amount sufficient to induce a cell to express NKX2-5, MEF2c, or a combination thereof.
30. The composition of any of statements 1-29, wherein the agent(s) or compound(s) is present in an amount sufficient to induce a cell to express α-Actinin, MLC2v, MY20, cMHC, NKX2-5, MEF2c, GATA4, ISL1, cTNT, cTNI, MLC2a or any combination thereof.
31. A composition comprising a GSK3 inhibitor, and at least two growth factors selected from the group consisting of BMP4, Activin A and VEGF.
32. A composition consisting essentially of a carrier, a GSK3 inhibitor, BMP4, Activin A and VEGF.
33. The composition of any of statements 1-32, further comprising a physiologically acceptable excipient or carrier.
34. The composition of any of statements 1-33, further comprising a cell culture media.
35. The composition of any of statements 1-34, furthering comprising one or more cells.
36. The composition of statement 35, wherein the one or more cells are non-cardiac cells.
37. The composition of statement 35 or 36, wherein the one or more cells are differentiated cells.
38. The composition of any of statements 35-37, wherein the one or more cells are somatic cells.
39. The composition of any of statements 35-38, wherein the one or more cells are adult cells.
40. The composition of any of statements 35-39, wherein the one or more cells are multipotent, unipotent, or progenitor cells.
41. The composition of any of statements 35-40, wherein the one or more cells are newborn cord blood cells, or newborn stem cells.
42. The composition of any of statements 35-41, wherein the one or more cells are allogenic or autologous cells.
43. The composition of any of statements 1-42, further comprising a heterogeneous or homogeneous mixture of cells.
44. A cell culture media comprising the composition of any of statements 1-43.
45. A method of generating a cardiac progenitor cell or a cardiomyocyte comprising contacting a selected cell with the composition of any of statements 1-43, or the cell media of statement 44, to thereby generate a cardiac progenitor cell or a cardiomyocyte.
46. The method of statement 45, wherein the selected cell is a population of cells.
47. The method of statement 45 or 46, wherein the selected cell is a differentiated cell.
48. The method of any of statements 45-47, wherein the selected cell is a non-cardiac cell.
49. The method of any of statements 45-48, wherein the selected cell is a non-cardiac progenitor cell.
50. The method of any of statements 45-49, wherein the selected cell is a somatic cell.
51. The method of any of statements 45-50, wherein the selected cell is a heterogeneous or homogeneous mixture of cells.
52. The method of any of statements 45-51, wherein the selected cell is an adult cell.
53. The method of any of statements 45-52, wherein the selected cell is a multipotent, unipotent, or progenitor cell.
54. The method of any of statements 45-53, wherein the selected cell is a newborn cord blood cell, or a newborn stem cell.
55. The method of any of statements 45-54, wherein the selected cell is an allogenic or autologous cell.
56. The method of any of statements 45-55, wherein the selected cell is contacted with the composition or the media for a time and/or with an amount of each agent sufficient to induce the selected cell to express GATA4, ISL1 or a combination thereof.
57. The method of any of statements 45-56, wherein the selected cell is contacted with the composition or the media for a time and/or with an amount of each agent sufficient to induce the selected cell to express NKX2-5, MEF2c, or a combination thereof.

58. The method of any of statements 45-57, wherein the selected cell is contacted with the composition or the media for a time and/or with an amount of each agent sufficient to induce the selected cell to express α-Actinin, MLC2v, MY20, cMHC, NKX2-5, MEF2c, GATA4, ISL1, cTNT, cTNI, MLC2a or any combination thereof.
59. The method of any of statements 45-59, further comprising administering the cardiac progenitor cell or the cardiomyocyte to a subject.
60. The method of any of statements 45-59, further comprising administering at least about 100 of the cardiac progenitor cells or the cardiomyocytes to a subject.
61. The method of any of statements 45-60, comprising administering at least about 1000, or at least about 10,000, or at least about 100,000, or at least about 1,000.000, or at least about 10,000,000, or at least about 100,000,000 of the cardiac progenitor cells or the cardiomyocytes to a subject.
62. The method of any of statements 45-61, wherein the cardiac progenitor cell(s) or the cardiomyocyte(s) is/are allogenic or autologous cell(s).
63. The method of any of statements 45-62, wherein the cardiac progenitor cell(s) or the cardiomyocyte(s) is/are cardiac progenitor cells.
64. The method of any of statements 45-63, wherein the cardiac progenitor cell(s) or the cardiomyocyte(s) is/are mature cardiomyocyte(s).
65. The method of any of statements 45-64, wherein the subject suffers or is suspected of suffering from a heart condition or disease.
66. The method of any of statements 45-65, wherein the subject's heart is abnormally enlarged, thickened and/or stiffened.
67. The method of any of statements 45-66, wherein the subject suffers or is suspected of suffering from a heart condition or disease resulting from inflammation, a metabolic condition, toxic exposure, an infiltrative process, a fibroplastic process, a hematological condition, a genetic condition, or a combination thereof.
68. The method of any of statements 45-67, wherein the subject suffers or is suspected of suffering from congestive heart failure, myocardial infarction, cardiac ischemia, myocarditis, arrhythmia, Duchenne muscular dystrophy, Emery Dreiffuss dilated cardiomyopathy, or any combination thereof.
69. A method comprising administrating the composition of any of statements 1-43, to a subject.
70. The method of statement 69, wherein the composition contains one or more cardiac progenitor cells and/or one or more mature cardiomyocytes.
71. The method of statement 69 or 70, wherein the composition contains one or more allogenic or autologous cells.
72. The method of any of statements 69-71, wherein the composition contains one or more, or at least about 1000, cells that express GATA4, ISL1 or a combination thereof.
73. The method of any of statements 69-72, wherein the composition contains one or more, or at least about 1000, cells that express NKX2-5, MEF2c, or a combination thereof.
74. The method of any of statements 69-73, wherein the composition contains one or more, or at least about 1000, cells that express α-Actinin, MLC2v, MY20, cMHC, NKX2-5, MEF2c, GATA4, ISL1, cTNT, cTNI, MLC2a or any combination thereof.
75. The method of any of statements 69-74, wherein the composition contains at least about 1000, or at least about 10,000, or at least about 100,000, or at least about 1,000,000, or at least about 10,000,000, or at least about 100,000,000 cardiac progenitor cells and/or mature cardiomyocytes.
76. The method of any of statements 69-75, wherein the subject is in need of administration of the composition.
77. The method of any of statements 69-76, wherein the subject is in need of cardiac progenitor cells and/or one or more mature cardiomyocytes.
78. The method of any of statements 69-77, wherein the composition is administered for a time and/or with an amount of each agent sufficient to reduce the symptoms of a heart condition or disease.
79. The method of any of statements 69-78, wherein the subject's heart is abnormally enlarged, thickened and/or stiffened.
80. The method of any of statements 69-79, wherein the subject suffers or is suspected of suffering from a heart condition or disease resulting from inflammation, a metabolic condition, toxic exposure, an infiltrative process, a fibroplastic process, a hematological condition, a genetic condition, or a combination thereof.
81. The method of any of statements 69-80, wherein the subject suffers or is suspected of suffering from congestive heart failure, myocardial infarction, cardiac ischemia, myocarditis, arrhythmia, Duchenne muscular dystrophy, Emery Dreiffuss dilated cardiomyopathy, or any combination thereof.
82. A kit comprising the composition of any of statements 1-43, and instructions for using the composition.
83. The kit of statement 82, further comprising components for in vitro cell culture of a selected cell.
84. The kit of statement 82 or 83, further comprising cell culture medium, one or more sterile cell collection devices, or a supplementary factor.
85. The kit of statement 84, wherein the supplementary factor comprises at least one bone morphogenic protein, brain derived neurotrophic factor, ciliary neurotrophic factor, cytokine-induced neutrophil chemotactic factor 1, cytokine-induced neutrophil chemotactic factor 2α, cytokine-induced neutrophil chemotactic factor 2β, β endothelial cell growth factor, endothelin 1, epidermal growth factor, epithelial-derived neutrophil attractant, fibroblast growth factor, growth related protein, heparin binding epidermal growth factor, hepatocyte growth factor, insulin-like growth factor, keratinocyte growth factor, leukemia inhibitory factor, neurotrophin, placenta growth factor, platelet-derived endothelial cell growth factor, platelet derived growth factor, pre-B cell growth stimulating factor, stem cell factor, transforming growth factor, latent transforming growth factor, transforming growth factor β binding protein, vascular endothelial growth factor or any combination thereof.
86. The kit of any of statements 82-85, further comprising a population of starting cells, cardiac progenitor cells, cardiomyocytes or cardiac cells generated by contacting the cells with the composition.
87. The kit of any of statements 82-86, further comprising a diluent, a pharmaceutically acceptable carrier, a syringe, a catheter, or a device for delivery of cells or of the composition.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims.

As used herein and in the appended claims, the singular forms "a," "an," and "the" include plural reference unless the context clearly dictates otherwise. Thus, for example, a reference to "a compound," "a cell," "a nucleic acid" or "a polypeptide" includes a plurality of such compounds, cells, nucleic acids or polypeptides (for example, a solution of cells, nucleic acids or polypeptides, a suspension of cells, or a series of compound, cell, nucleic acid or polypeptide preparations), and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

What is claimed:

1. A method of generating a cardiac progenitor cell or a cardiomyocyte comprising:
    contacting at least one fibroblast or a cell derived therefrom with a cardiac induction medium comprising a GSK3 inhibitor, a BMP4 agonist, an Activin A agonist and a VEGF agonist; and
    allowing the cells to incubate in the medium;
    thereby generate at least one cardiac progenitor cell or a cardiomyocyte.

2. The method of claim 1, wherein the fibroblast is a human fibroblast.

3. The method of claim 1, wherein the fibroblast is contacted with one or more chemical agents prior to the contacting with the cardiac induction medium.

4. The method of claim 2, wherein the fibroblast is contacted with one or more agents selected from a WNT agonist, a GSK3 inhibitor, a TGF-beta inhibitor, an inhibitor of extracellular signal-regulated kinase 1 (ERK1), an inhibitor of Ras GTPase-activating protein (Ras-GAP), an Oct-4 activator, a rho-associated protein kinase, an iron chelator, a KDM5B inhibitor, a histone methyltransferase inhibitor, a PDGF tyrosine kinase inhibitor.

5. The method of claim 4, wherein the fibroblast is contacted with each agent for a time sufficient to induce the cardiac progenitor cell or cardiomyocyte to express α-Actinin, MLC2v, MY20, cMHC NKX2-5, MEF2c, GATA4, ISLL cTNL cTN1, MLC2a or any combination thereof.

6. The method of claim 1, furthering comprising administering the cardiac progenitor cell(s) or the cardiomyocyte(s) to a subject.

7. The method of claim 1, wherein the fibroblast is allogenic.

8. The method of claim 1, wherein the fibroblast is autologous.

9. The method of claim 1, wherein the fibroblast is obtained from a subject who suffers or is suspected of suffering from a heart condition or disease.

10. The method of claim 1, wherein the fibroblast is obtained from a healthy subject.

11. The method of claim 1, wherein the cardiac progenitor cell or the cardiomyocyte is allogenic.

12. The method of claim 1, wherein the cardiac progenitor cell or the cardiomyocyte is autologous.

13. A method of generating a cardiac progenitor cell or a cardiomyocyte comprising:
    contacting at least one fibroblast with a cardiac reprogramming medium comprising one or more agents selected from a WNT agonist, a GSK3 inhibitor, a TGF-beta inhibitor, an inhibitor of extracellular signal-regulated kinase 1 (ERK1), an inhibitor of Ras GTPase-activating protein (Ras-GAP), an Oct-4 activator, a rho-associated protein kinase, an iron chelator, a KDM5B inhibitor, a histone methyltransferase inhibitor, a PDGF tyrosine kinase inhibitor;
    contacting the cell with a cardiac induction medium comprising a GSK3 inhibitor, a BMP4 agonist, an Activin A agonist and a VEGF agonist;
    thereby generating at least one cardiac progenitor cell or a cardiomyocyte.

14. The method of claim 13, wherein the fibroblast is a human fibroblast.

15. The method of claim 13, wherein the fibroblast is contacted with each agent for a time sufficient to induce the cardiac progenitor cell or cardiomyocyte to express α-Actinin, MLC2v, MY20, cMHC NKX2-5, MEF2c, GATA4, ISLL cTNL cTN1, MLC2a or any combination thereof.

16. The method of claim 13, furthering comprising administering the cardiac progenitor cell or the cardiomyocyte to a subject.

17. The method of claim 10, wherein the fibroblast is allogenic.

18. The method of claim 10, wherein the fibroblast is autologous.

19. The method of claim 10, wherein the fibroblast is obtained from a subject who suffers or is suspected of suffering from a heart condition or disease.

20. The method of claim 10, wherein the fibroblast is obtained from a healthy subject.

21. The method of claim 10, wherein the cardiac progenitor cell or the cardiomyocyte is allogenic.

22. The method of claim 10 wherein the cardiac progenitor cell or the cardiomyocyte is autologous.

* * * * *

SEQUENCE LISTING

```
<160> NUMBER OF SEQ ID NOS: 67

<210> SEQ ID NO 1
<211> LENGTH: 21
<212> TYPE: DNA
<213> ORGANISM: Homo sapiens

<400> SEQUENCE: 1
ttctgatgga ctcggaataa a                                              21

<210> SEQ ID NO 2
<211> LENGTH: 21
<212> TYPE: DNA
<213> ORGANISM: Homo sapiens

<400> SEQUENCE: 2
gcttactcca ccggctgata a                                              21

<210> SEQ ID NO 3
<211> LENGTH: 21
<212> TYPE: DNA
<213> ORGANISM: Homo sapiens

<400> SEQUENCE: 3
atgccacgct tcgcctcata a                                              21

<210> SEQ ID NO 4
<211> LENGTH: 21
<212> TYPE: DNA
<213> ORGANISM: Homo sapiens

<400> SEQUENCE: 4
cggcctttac aagaagacat t                                              21

<210> SEQ ID NO 5
<211> LENGTH: 21
<212> TYPE: DNA
<213> ORGANISM: Homo sapiens
```

```
<400> SEQUENCE: 5
cctgaggaag aagcggaaat a                                              21

<210> SEQ ID NO 6
<211> LENGTH: 21
<212> TYPE: DNA
<213> ORGANISM: Homo sapiens

<400> SEQUENCE: 6
ctgaaccact gcaagtctat c                                              21

<210> SEQ ID NO 7
<211> LENGTH: 21
<212> TYPE: DNA
<213> ORGANISM: Homo sapiens

<400> SEQUENCE: 7
acaacttaga ttgggtttat a                                              21

<210> SEQ ID NO 8
<211> LENGTH: 21
<212> TYPE: DNA
<213> ORGANISM: Homo sapiens

<400> SEQUENCE: 8
gctttgattg tgaagcattt a                                              21

<210> SEQ ID NO 9
<211> LENGTH: 21
<212> TYPE: DNA
<213> ORGANISM: Homo sapiens

<400> SEQUENCE: 9
atgccacgct tcgcctcata a                                              21

<210> SEQ ID NO 10
<211> LENGTH: 21
<212> TYPE: DNA
<213> ORGANISM: Homo sapiens

<400> SEQUENCE: 10
gcgatctttg tagaatttga t                                              21

<210> SEQ ID NO 11
<211> LENGTH: 21
<212> TYPE: DNA
<213> ORGANISM: Homo sapiens

<400> SEQUENCE: 11
cctctgtgaa gcaggtcttt c                                              21

<210> SEQ ID NO 12
<211> LENGTH: 21
<212> TYPE: DNA
<213> ORGANISM: Homo sapiens

<400> SEQUENCE: 12
ccctagttca tcgcaacctt t                                              21

<210> SEQ ID NO 13
<211> LENGTH: 21
<212> TYPE: DNA
```

```
<213> ORGANISM: Homo sapiens

<400> SEQUENCE: 13
ggatctgtga gaagcatatt t                                              21

<210> SEQ ID NO 14
<211> LENGTH: 21
<212> TYPE: DNA
<213> ORGANISM: Homo sapiens

<400> SEQUENCE: 14
tccacctcca gagactataa a                                              21

<210> SEQ ID NO 15
<211> LENGTH: 21
<212> TYPE: DNA
<213> ORGANISM: Homo sapiens

<400> SEQUENCE: 15
gctcctgtga ttcaatgtta t                                              21

<210> SEQ ID NO 16
<211> LENGTH: 21
<212> TYPE: DNA
<213> ORGANISM: Homo sapiens

<400> SEQUENCE: 16
gcaccgagtt tgtcttgaaa t                                              21

<210> SEQ ID NO 17
<211> LENGTH: 21
<212> TYPE: DNA
<213> ORGANISM: Homo sapiens

<400> SEQUENCE: 17
ttcgagagtt ccgcaagata g                                              21

<210> SEQ ID NO 18
<211> LENGTH: 21
<212> TYPE: DNA
<213> ORGANISM: Homo sapiens

<400> SEQUENCE: 18
gactgctgtt tatgctcatt a                                              21

<210> SEQ ID NO 19
<211> LENGTH: 21
<212> TYPE: DNA
<213> ORGANISM: Homo sapiens

<400> SEQUENCE: 19
gtgctactgc aatgccctac t                                              21

<210> SEQ ID NO 20
<211> LENGTH: 21
<212> TYPE: DNA
<213> ORGANISM: Homo sapiens

<400> SEQUENCE: 20
actgagcaac ctttgagatt g                                              21

<210> SEQ ID NO 21
<211> LENGTH: 21
```

```
<212> TYPE: DNA
<213> ORGANISM: Homo sapiens

<400> SEQUENCE: 21
gtggaagctg aaatgcgtgt a                                              21

<210> SEQ ID NO 22
<211> LENGTH: 21
<212> TYPE: DNA
<213> ORGANISM: Homo sapiens

<400> SEQUENCE: 22
ccttgcatac atggagtcta a                                              21

<210> SEQ ID NO 23
<211> LENGTH: 21
<212> TYPE: DNA
<213> ORGANISM: Homo sapiens

<400> SEQUENCE: 23
gcagagagta atggtgtgtt a                                              21

<210> SEQ ID NO 24
<211> LENGTH: 21
<212> TYPE: DNA
<213> ORGANISM: Homo sapiens

<400> SEQUENCE: 24
gcccaagtct tggtatgcta t                                              21

<210> SEQ ID NO 25
<211> LENGTH: 21
<212> TYPE: DNA
<213> ORGANISM: Homo sapiens

<400> SEQUENCE: 25
ggttagcgta acctggtata t                                              21

<210> SEQ ID NO 26
<211> LENGTH: 21
<212> TYPE: DNA
<213> ORGANISM: Homo sapiens

<400> SEQUENCE: 26
cagattatcc acccgtcaaa t                                              21

<210> SEQ ID NO 27
<211> LENGTH: 21
<212> TYPE: DNA
<213> ORGANISM: Homo sapiens

<400> SEQUENCE: 27
cctggtatat gcaactacca t                                              21

<210> SEQ ID NO 28
<211> LENGTH: 21
<212> TYPE: DNA
<213> ORGANISM: Homo sapiens

<400> SEQUENCE: 28
caacaggtca gacgcattta a                                              21

<210> SEQ ID NO 29
```

```
<211> LENGTH: 21
<212> TYPE: DNA
<213> ORGANISM: Homo sapiens

<400> SEQUENCE: 29
ccagacttac agggacactt a                                              21

<210> SEQ ID NO 30
<211> LENGTH: 21
<212> TYPE: DNA
<213> ORGANISM: Homo sapiens

<400> SEQUENCE: 30
ccttgaaaga agccttacaa a                                              21

<210> SEQ ID NO 31
<211> LENGTH: 21
<212> TYPE: DNA
<213> ORGANISM: Homo sapiens

<400> SEQUENCE: 31
atcgcttgct tcatcgatat t                                              21

<210> SEQ ID NO 32
<211> LENGTH: 21
<212> TYPE: DNA
<213> ORGANISM: Homo sapiens

<400> SEQUENCE: 32
cgagatggaa ttaacagtct t                                              21

<210> SEQ ID NO 33
<211> LENGTH: 21
<212> TYPE: DNA
<213> ORGANISM: Homo sapiens

<400> SEQUENCE: 33
gtgcctgttt accgaactaa t                                              21

<210> SEQ ID NO 34
<211> LENGTH: 21
<212> TYPE: DNA
<213> ORGANISM: Homo sapiens

<400> SEQUENCE: 34
gccacacttg aggccataat c                                              21

<210> SEQ ID NO 35
<211> LENGTH: 21
<212> TYPE: DNA
<213> ORGANISM: Homo sapiens

<400> SEQUENCE: 35
tcgcagagaa atcgggcatt t                                              21

<210> SEQ ID NO 36
<211> LENGTH: 21
<212> TYPE: DNA
<213> ORGANISM: Homo sapiens

<400> SEQUENCE: 36
agtacctgcg gtatcggtat a                                              21
```

```
<210> SEQ ID NO 37
<211> LENGTH: 21
<212> TYPE: DNA
<213> ORGANISM: Homo sapiens

<400> SEQUENCE: 37
gccacattgg aagccataat t                                             21

<210> SEQ ID NO 38
<211> LENGTH: 21
<212> TYPE: DNA
<213> ORGANISM: Homo sapiens

<400> SEQUENCE: 38
agtggcacca aaggtcattt g                                             21

<210> SEQ ID NO 39
<211> LENGTH: 21
<212> TYPE: DNA
<213> ORGANISM: Homo sapiens

<400> SEQUENCE: 39
ccagtgctag atcagtctgt t                                             21

<210> SEQ ID NO 40
<211> LENGTH: 21
<212> TYPE: DNA
<213> ORGANISM: Homo sapiens

<400> SEQUENCE: 40
ccgcgcaaat agaataatt t                                              21

<210> SEQ ID NO 41
<211> LENGTH: 21
<212> TYPE: DNA
<213> ORGANISM: Homo sapiens

<400> SEQUENCE: 41
gcacatagac taaggaataa a                                             21

<210> SEQ ID NO 42
<211> LENGTH: 21
<212> TYPE: DNA
<213> ORGANISM: Homo sapiens

<400> SEQUENCE: 42
gatgcaagtc tatgaccaat t                                             21

<210> SEQ ID NO 43
<211> LENGTH: 21
<212> TYPE: DNA
<213> ORGANISM: Homo sapiens

<400> SEQUENCE: 43
agtcccactc acctctattt a                                             21

<210> SEQ ID NO 44
<211> LENGTH: 21
<212> TYPE: DNA
<213> ORGANISM: Homo sapiens

<400> SEQUENCE: 44
tctgtacaga ccctcgaaat c                                             21
```

<210> SEQ ID NO 45
<211> LENGTH: 21
<212> TYPE: DNA
<213> ORGANISM: Homo sapiens

<400> SEQUENCE: 45
ttgagcacaa acggaactat g                                              21

<210> SEQ ID NO 46
<211> LENGTH: 21
<212> TYPE: DNA
<213> ORGANISM: Homo sapiens

<400> SEQUENCE: 46
tatgggatca acaggtattt a                                              21

<210> SEQ ID NO 47
<211> LENGTH: 21
<212> TYPE: DNA
<213> ORGANISM: Homo sapiens

<400> SEQUENCE: 47
ttagacctgg acaccttatt a                                              21

<210> SEQ ID NO 48
<211> LENGTH: 21
<212> TYPE: DNA
<213> ORGANISM: Homo sapiens

<400> SEQUENCE: 48
tggatttgat gtccctatta t                                              21

<210> SEQ ID NO 49
<211> LENGTH: 21
<212> TYPE: DNA
<213> ORGANISM: Homo sapiens

<400> SEQUENCE: 49
ggaagtacat ccggctgtat t                                              21

<210> SEQ ID NO 50
<211> LENGTH: 21
<212> TYPE: DNA
<213> ORGANISM: Homo sapiens

<400> SEQUENCE: 50
cctgttcatc ccggtgaaat a                                              21

<210> SEQ ID NO 51
<211> LENGTH: 21
<212> TYPE: DNA
<213> ORGANISM: Homo sapiens

<400> SEQUENCE: 51
gcatcagaaa gccgaatgtt t                                              21

<210> SEQ ID NO 52
<211> LENGTH: 21
<212> TYPE: DNA
<213> ORGANISM: Homo sapiens

<400> SEQUENCE: 52
catagaatgt agcgtgtaaa t                                              21

<210> SEQ ID NO 53
<211> LENGTH: 21
<212> TYPE: DNA
<213> ORGANISM: Homo sapiens

<400> SEQUENCE: 53
ttgctgacca ggtcgacaaa t                                              21

<210> SEQ ID NO 54
<211> LENGTH: 21
<212> TYPE: DNA
<213> ORGANISM: Homo sapiens

<400> SEQUENCE: 54
gaacgggaaa ctactccttt a                                              21

<210> SEQ ID NO 55
<211> LENGTH: 21
<212> TYPE: DNA
<213> ORGANISM: Homo sapiens

<400> SEQUENCE: 55
ctgcaactct agccctatat c                                              21

<210> SEQ ID NO 56
<211> LENGTH: 21
<212> TYPE: DNA
<213> ORGANISM: Homo sapiens

<400> SEQUENCE: 56
acgttgggaa gacgagcaat a                                              21

<210> SEQ ID NO 57
<211> LENGTH: 21
<212> TYPE: DNA
<213> ORGANISM: Homo sapiens

<400> SEQUENCE: 57
gctggccagt tgagctataa t                                              21

<210> SEQ ID NO 58
<211> LENGTH: 21
<212> TYPE: DNA
<213> ORGANISM: Homo sapiens

<400> SEQUENCE: 58
gaacggaaga tccaggagaa a                                              21

<210> SEQ ID NO 59
<211> LENGTH: 21
<212> TYPE: DNA
<213> ORGANISM: Homo sapiens

<400> SEQUENCE: 59
gcagaaggaa tcaacacaga a                                              21

<210> SEQ ID NO 60
<211> LENGTH: 21
<212> TYPE: DNA
<213> ORGANISM: Homo sapiens

<400> SEQUENCE: 60

-continued cgggcacaga aagacttcct t    21

<210> SEQ ID NO 61
<211> LENGTH: 21
<212> TYPE: DNA
<213> ORGANISM: Homo sapiens

<400> SEQUENCE: 61
gcaacgattc agtttcacca a    21

<210> SEQ ID NO 62
<211> LENGTH: 21
<212> TYPE: DNA
<213> ORGANISM: Homo sapiens

<400> SEQUENCE: 62
gacctgaaac ttactacaga t    21

<210> SEQ ID NO 63
<211> LENGTH: 21
<212> TYPE: DNA
<213> ORGANISM: Homo sapiens

<400> SEQUENCE: 63
caaacatgag acctccctgt t    21

<210> SEQ ID NO 64
<211> LENGTH: 21
<212> TYPE: DNA
<213> ORGANISM: Homo sapiens

<400> SEQUENCE: 64
gatgcctcta gccctaaatt a    21

<210> SEQ ID NO 65
<211> LENGTH: 21
<212> TYPE: DNA
<213> ORGANISM: Homo sapiens

<400> SEQUENCE: 65
acccttgatc cgtgatcatt t    21

<210> SEQ ID NO 66
<211> LENGTH: 21
<212> TYPE: DNA
<213> ORGANISM: Homo sapiens

<400> SEQUENCE: 66
gcccagttga caacagaaac a    21

<210> SEQ ID NO 67
<211> LENGTH: 21
<212> TYPE: DNA
<213> ORGANISM: Homo sapiens

<400> SEQUENCE: 67
caacaagatg aagagcacca a    21